US007504364B2

(12) United States Patent
Carlson

(10) Patent No.: US 7,504,364 B2
(45) Date of Patent: *Mar. 17, 2009

(54) METHODS OF MAKING ARRAYS AND ARTIFICIAL RECEPTORS

(75) Inventor: Robert E Carlson, Minnetonka, MN (US)

(73) Assignee: Receptors LLC, Chaska, MN (US)

( * ) Notice: Subject to any disclaimer, the term of this patent is extended or adjusted under 35 U.S.C. 154(b) by 184 days.

This patent is subject to a terminal disclaimer.

(21) Appl. No.: 10/244,727

(22) Filed: Sep. 16, 2002

(65) Prior Publication Data

US 2003/0203405 A1 Oct. 30, 2003

Related U.S. Application Data

(60) Provisional application No. 60/400,605, filed on Aug. 2, 2002, provisional application No. 60/375,655, filed on Apr. 26, 2002, provisional application No. 60/362,600, filed on Mar. 8, 2002, provisional application No. 60/360,980, filed on Mar. 1, 2002.

(51) Int. Cl.
C40B 50/00 (2006.01)
(52) U.S. Cl. .............................. 506/30; 506/23; 506/13; 435/5
(58) Field of Classification Search .................. None
See application file for complete search history.

(56) References Cited

U.S. PATENT DOCUMENTS

| 5,159,656 | A |   | 10/1992 | Goldstein |
| 5,225,374 | A |   | 7/1993 | Fare et al. |
| 5,281,539 | A |   | 1/1994 | Schramm |
| 5,324,633 | A |   | 6/1994 | Fodor et al. |
| 5,340,474 | A |   | 8/1994 | Kauvar |
| 5,453,533 | A |   | 9/1995 | Luo et al. |
| 5,475,100 | A |   | 12/1995 | Hashino et al. |
| 5,677,196 | A |   | 10/1997 | Herron et al. |
| 5,690,894 | A |   | 11/1997 | Pinkel et al. |
| 5,770,380 | A |   | 6/1998 | Hamilton et al. |
| 5,804,563 | A |   | 9/1998 | Still et al. |
| 5,925,529 | A |   | 7/1999 | Coughlin et al. |
| 5,942,393 | A |   | 8/1999 | Nobori et al. |
| 5,990,163 | A | * | 11/1999 | Evans et al. .................. 514/549 |
| 5,998,594 | A |   | 12/1999 | Goodman et al. |
| 6,030,782 | A |   | 2/2000 | Anderson et al. |
| 6,061,636 | A |   | 5/2000 | Horlbeck |
| 6,066,448 | A |   | 5/2000 | Wohlstadter et al. |
| 6,083,758 | A |   | 7/2000 | Imperiali et al. |
| 6,083,763 | A | * | 7/2000 | Balch ......................... 436/518 |
| 6,096,551 | A |   | 8/2000 | Barbas et al. |
| 6,111,123 | A |   | 8/2000 | Coucouvanis et al. |
| 6,153,743 | A |   | 11/2000 | Hubbell et al. |
| 6,168,912 | B1 |   | 1/2001 | Chen |
| 6,198,912 | B1 |   | 3/2001 | Piloni |
| 6,207,369 | B1 |   | 3/2001 | Wohlstadter et al. |
| 6,261,776 | B1 |   | 7/2001 | Pirrung et al. |
| 6,287,765 | B1 |   | 9/2001 | Cubicciotti |
| 6,297,059 | B1 |   | 10/2001 | Song et al. |
| 6,316,268 | B1 |   | 11/2001 | Yang et al. |
| 6,316,616 | B1 |   | 11/2001 | Jacobsen et al. |
| 6,331,441 | B1 |   | 12/2001 | Balch et al. |
| 6,344,272 | B1 |   | 2/2002 | Oldenburg et al. |
| 6,346,413 | B1 |   | 2/2002 | Fodor et al. |
| 6,346,423 | B1 |   | 2/2002 | Schembri |
| 6,361,944 | B1 |   | 3/2002 | Mirkin et al. |
| 6,372,907 | B1 |   | 4/2002 | Lee et al. |
| 6,410,585 | B1 | * | 6/2002 | Larsen et al. ................ 514/424 |
| 6,419,881 | B1 |   | 7/2002 | Weinberg et al. |
| 6,428,811 | B1 |   | 8/2002 | West et al. |
| 6,489,093 | B1 |   | 12/2002 | Jacobsen et al. |
| 6,528,020 | B1 |   | 3/2003 | Dai et al. |
| 6,543,936 | B2 |   | 4/2003 | Feldman |
| 6,627,396 | B1 |   | 9/2003 | Swanson et al. |
| 6,645,517 | B2 |   | 11/2003 | West et al. |
| 6,649,356 | B2 |   | 11/2003 | Bryan et al. |
| 6,652,835 | B1 |   | 11/2003 | Lauffer et al. |
| 6,667,159 | B1 |   | 12/2003 | Walt et al. |
| 6,673,533 | B1 |   | 1/2004 | Wohlstadter et al. |
| 6,698,201 | B1 |   | 3/2004 | Sarkar et al. |

(Continued)

FOREIGN PATENT DOCUMENTS

DE 197 40 263 5/1998

(Continued)

OTHER PUBLICATIONS

Tsuda, M. et al., Suberedamines A and B, New Bromotyrosine Alkaloids from a Sponge Suberea Species, J. Nat. Prod. 2001, vol. 64, 980-982.*

(Continued)

Primary Examiner—Mark L. Shibuya
Assistant Examiner—Jeffrey S. Lundgren
(74) Attorney, Agent, or Firm—Merchant & Gould P.C.

(57) ABSTRACT

The present invention relates to artificial receptors and arrays or microarrays of artificial receptors or candidate artificial receptors. Each member of the array includes a plurality of building block compounds, typically immobilized in a spot on a support. The present invention also includes the building blocks, combinations of building blocks, arrays of building blocks, and receptors constructed of these building blocks together with a support. The present invention also includes methods of making and using these arrays and receptors.

30 Claims, 26 Drawing Sheets

U.S. PATENT DOCUMENTS

| | | | |
|---|---|---|---|
| 6,699,501 | B1 | 3/2004 | Neu et al. |
| 6,699,719 | B2 | 3/2004 | Nguyen et al. |
| 6,767,194 | B2 | 7/2004 | Jeon et al. |
| 6,767,706 | B2 | 7/2004 | Quake et al. |
| 6,875,620 | B1 | 4/2005 | Schembri |
| 7,018,792 | B2 | 3/2006 | Swanson et al. |
| 2002/0019015 | A1 | 2/2002 | Lahiri et al. |
| 2002/0090728 | A1 | 7/2002 | Shair et al. |
| 2002/0187197 | A1 | 12/2002 | Caruso et al. |
| 2002/0187347 | A1 | 12/2002 | Halas et al. |
| 2002/0187509 | A1 | 12/2002 | Shao et al. |
| 2003/0083235 | A1 | 5/2003 | Danishefsky et al. |
| 2003/0104360 | A1 | 6/2003 | Still et al. |
| 2003/0138853 | A1* | 7/2003 | Lahiri et al. ................. 435/7.1 |
| 2003/0143756 | A1 | 7/2003 | Fisher et al. |
| 2003/0156991 | A1 | 8/2003 | Halas et al. |
| 2003/0175517 | A1 | 9/2003 | Voigt et al. |
| 2003/0219384 | A1 | 11/2003 | Donath et al. |
| 2003/0228605 | A1 | 12/2003 | Slootstra et al. |
| 2004/0010126 | A1 | 1/2004 | Lubman et al. |
| 2004/0013721 | A1 | 1/2004 | Antipov et al. |
| 2004/0076681 | A1 | 4/2004 | Dennis et al. |
| 2004/0077102 | A1 | 4/2004 | Coute et al. |
| 2004/0102607 | A1 | 5/2004 | Danishefsky et al. |
| 2004/0137526 | A1 | 7/2004 | Hanash et al. |
| 2004/0151733 | A1 | 8/2004 | Livingston et al. |
| 2004/0185473 | A1 | 9/2004 | Cuppoletti et al. |
| 2004/0208884 | A1 | 10/2004 | Danishefsky et al. |
| 2006/0051802 | A1 | 3/2006 | Carlson |

FOREIGN PATENT DOCUMENTS

| | | |
|---|---|---|
| GB | 2 319 838 A | 6/1998 |
| WO | WO 93/25910 A1 * | 12/1993 |
| WO | WO 95/02566 | 1/1995 |
| WO | WO 98/12156 | 3/1998 |
| WO | WO 99/25384 | 5/1999 |
| WO | WO 00/13016 | 3/2000 |
| WO | WO 00/13017 | 3/2000 |
| WO | WO 00/16733 | 3/2000 |
| WO | WO 00/66790 | 11/2000 |
| WO | WO 00/79008 A2 | 12/2000 |
| WO | WO 01/01140 A1 * | 1/2001 |
| WO | WO 01/18545 A2 | 3/2001 |
| WO | WO 01/46698 A2 | 6/2001 |
| WO | WO 03/012390 A2 | 2/2003 |
| WO | WO 03/031975 A1 | 4/2003 |
| WO | WO 03/033674 A2 | 4/2003 |
| WO | WO 03/074990 A2 | 9/2003 |

OTHER PUBLICATIONS

Buchanan, J.L. et al., Practical synthesis of fully-substituted peptide thiazoles, Tetrahedron Letters 40 (1999) pp. 3985-3988.*

Reid et al., Conformationally Constrained Macrocycles That Mimic Tripeptide β-Strands in Water and Aprotic Solvents, J. Am. Chem. Soc. (May 22, 2002), vol. 124, 5673-5683.*

Angers et al., Proc. Natl. Acad. Sci. USA, (Mar. 28, 2000), vol. 97 (7), pp. 3684-3689.*

Blackwell, H. et al., "Exploiting Site—Site Interactions on Solid Support to Generate Dimeric Molecules," *Organic Letters*, vol. 3, No. 8, pp. 1185-1188 (2001).

Bluhm, L. et al., "An Alternative Procedure to Screen Mixture Combinatorial Libraries for Selectors for Chiral Chromatography," *Analytical Chemistry*, vol. 72, No. 21, pp. 5201-5205 (Nov. 1, 2000).

Borchardt, A. et al., "Synthetic Receptor Binding Elucidated with an Encoded Combinatorial Library," *J. Am. Chem. Soc.*, vol. 116, No. 1, pp. 373-374 (1994).

Boyce, R. et al., "Peptidosteroidal Receptors for Opioid Peptides, Sequence-Selective Binding Using a Synthetic Receptor Library," *J. Am. Chem. Soc.*, vol. 116, No. 17, pp. 7955-7956 (1994).

Brennan, M., "Protein Interactions: Putting on the Brakes. Antibody Mimics that Bind to Protein Surface Block Protein-Protein Interactions," *C & EN*, pp. 65-66, 69 (Jan. 22, 2001).

Breslow, R. et al., "Sequence Selective Binding of Peptides by Artificial Receptors in Aqueous Solution," *J. Am. Chem. Soc.*, vol. 120, No. 14, pp. 3536-3537 (1998).

Bunin, B. et al., "A General and Expedient Method for the Solid-Phase Synthesis of 1,4-Benzodiazepine Derivatives," *J. Am. Chem. Soc.*, vol. 114, pp. 10997-10998 (1992).

Cha, X. et al., "Molecular Recognition of Aqueous Dipeptides by Noncovalently Aligned Oligoglycine Units at the Air/Water Interface," *J. Am. Chem. Soc.*, vol. 117, No. 48, pp. 11833-11838 (1995).

Cheng, Y. et al., "Sequence-Selective Peptide Binding with a PeptidoA,B-trans-steroidal Receptor Selected from an Encoded Combinatorial Receptor Library," *J. Am. Chem. Soc.*, vol. 118, No. 7, pp. 1813-1814 (1996).

Cousins, G. et al., "Molecular Evolution: Dynamic Combinatorial Libraries, Autocatalytic Networks and the Quest for Molecular Function," *Current Opinion in Chemical Biology*, vol. 4, pp. 270-279 (2000).

Deng, Q. et al., "Retention and Separation of Adenosine and Analogues by Affinity Chromatography with an Aptamer Stationary Phaase," *Anal. Chem.*, vol. 73, No. 22, pp. 5415-5421 (Nov. 15, 2001).

Fiammengo, R. et al., "Synthetic Self-Assembled Models with Biomimetic Functions," *Current Opinion in Chemical Biology*, vol. 5, pp. 660-673 (2001).

Freemantle, M, "Amplification of the Fittest. Dynamic Combinatorial Library Strategy Leads to Discovery and Synthesis of New Compounds," *C & EN*, pp. 31-33 (Sep. 2, 2002).

Hamilton, A. et al., "Model Systems Artificial Models of Protein Function," *Current Opinion in Chemical Biology*, vol. 5, pp. 623-625 (2001).

Hamuro, Y. et al., "A Calixarene with Four Peptide Loops: An Antibody Mimic for Recognition of Protein Surfaces," *Angew. Chem. Int. Ed. Engl.*, vol. 36, No. 23, pp. 2680-2683 (1997).

Hamuro, Y. et al., "Functionalized Oligoanthranilamides: Modular and Conformationally Controlled Scaffolds," *Bioorganic & Medicinal Chemistry*, vol. 9, pp. 2355-2363 (2001).

Haupt, K. et al., "Molecularly Imprinted Polymers and Their Use in Biomimetic Sensors," *Chem. Rev.*, vol. 100, No. 7, pp. 2495-2504 (2000).

Hergenrother, P. et al., "Small-Molecule Microarrays: Covalent Attachment and Screening of Alcohol-Containing Small Molecules on Glass Slides," *J. Am. Chem. Soc.*, vol. 122, No. 32, pp. 7849-7850 (2000).

Hubbard, R. et al., "Highly Substituted *ter*-Cyclopentanes as Receptors for Lipid A," *J. Am. Chem. Soc.*, vol. 123, No. 24, pp. 5810-5811 (2001).

Huc, I. et al., "Virtual Combinatorial Libraries: Dynamic Generation of Molecular and Supramolecular Diversity by Self-Assembly," *Proc. Natl. Acad. Sci. USA*, vol. 94, pp. 2106-2110 (Mar. 1997).

"Introducing Human Cancer OligoArray™", *Sigma Genosys*, 1 page (2002).

Jain, R. et al., "Protein Surface Recognition by Synthetic Receptors Based on a Tetraphenylporphyrin Scaffold," *Organic Letters*, vol. 2, No. 12, pp. 1721-1723 (2000).

Kasher, R. et al., "Design and Synthesis of Peptides that Bind α-Bungarotoxin with High Affinity," *Chemistry & Biology*, vol. 8, pp. 147-155 (2001).

Kick, E. et al., "Structure-Based Design and Combinatorial Chemistry Yield Low Nanomolar Inhibitors of Cathepsin D," *Chemistry & Biology*, vol. 4, No. 4, pp. 297-307 (Apr. 1997).

Kodadek, T., "Development of Protein-Detecting Microarrays and Related Devices," *Trends in Biochemical Sciences*, vol. 27, No. 6, pp. 295-300 (Jun. 2002).

Lam, K. et al., "The 'One-Bead-One Compound' Combinatorial Library Method," *Chemical Reviews*, vol. 97, No. 2, pp. 411-448 (1997).

Lee, D. et al., "Pairwise Use of Complexity-Generating Reactions in Diversity-Oriented Organic Synthesis," *Organic Letters*, vol. 2, No. 5, pp. 709-712 (2000).

Lehn, J et al., "Dynamic Combinatorial Chemistry," *Science*, vol. 291, pp. 2331-2332 (Mar. 23, 2001).

Li, S. et al., "Artificial Receptor-Facilitated Solid-Phase Microextraction of Barbiturates," *Anal. Chem.*, vol. 71, No. 11, pp. 2146-2151 (Jun. 1, 1999).

MacBeath, G. et al., "Printing Small Molecules as Microarrays and Detecting Protein—Ligand Interactions en Masse," *J. Am. Chem. Soc.*, vol. 121, No. 34, pp. 7967-7968 (1999).

MacBeath, G. et al., "Printing Proteins as Microarrays for High-Throughput Function Determination," *Science*, vol. 289, pp. 1760-1763 (Sep. 8, 2000).

Maly, D. et al., "Combinatorial Target-Guided Ligand Assembly: Identification of Potent Subtype-Selective c-Src Inhibitors," *PNAS*, vol. 97, No. 6, pp. 2419-2424 (Mar. 14, 2000).

McDonald, D. et al., "Application of Free Energy Perturbation Calculations to the Enantioselective Binding of Peptides to $C_3$-Symmetric Synthetic Receptors," *J. Am. Chem. Soc.*, vol. 118, No. 8, pp. 2073-2077 (1996).

Moore, J. et al., "'Masterpiece' Copolymer Sequences by Targeted Equilibrium-Shifting," *Organic Letters*, vol. 2, No. 7, pp. 915-918 (2000).

Mosbach, K. et al., "Generation of New Enzyme Inhibitors Using Imprinted Binding Sites: The Anti-Idiotypic Approach, a Step Toward the Next Generation of Molecular Imprinting," *J. Am. Chem. Soc.*, vol. 123, No. 49, pp. 12420-12421 (2001).

Ogoshi, H. et al., "Novel Approaches to Molecular Recognition Using Porphyrins," *Current Opinion in Chemical Biology*, vol. 3, pp. 736-739 (1999).

Opatz, T. et al., "A Selectively Deprotectable Triazacyclophane Scaffold for the Construction of Artificial Receptors," *Organic Letters*, vol. 3, No. 22, pp. 3499-3502 (2001).

Oprea, T. et al., "Chemography: The Art of Navigating in Chemical Space," *J. Comb. Chem.*, vol. 3, No. 2, pp. 157-166 (2001).

Park, H. et al., "Protein Surface Recognition by Synthetic Receptors: A Route to Novel Submicromolar Inhibitors for α-Chymotrypsin," *J. Am. Chem. Soc.*, vol. 121, No. 1, pp. 8-13 (1999).

Park, H. et al., "Modulation of Protein-Protein Interactions by Synthetic Receptors: Design of Molecules that Disrupt Serine Protease-Proteinaceous Inhibitor Interaction," *PNAS*, vol. 99, No. 8, pp. 5105-5109 (Apr. 16, 2002).

Pattarawarapan, M. et al., "A Linker Scaffold to Present Dimers of Pharmacophores Prepared by Solid-Phase Syntheses," *Angew. Chem. Int. Ed.*, vol. 39, No. 23, pp. 4299-4301 (2000).

Peczuh, M. et al., "Peptide and Protein Recognition by Designed Molecules," *Chem. Rev.*, vol. 100, No. 7, pp. 2479-2494 (2000).

Pirrung, M., "Spatially Addressable Combinatorial Libraries," *Chemical Reviews*, vol. 97, No. 2, pp. 473-488 (1997).

Quaglia, M. et al., "Target Analogue Imprinted Polymers with Affinity for Folic Acid and Related Compounds," *J. Am. Chem. Soc.*, vol. 123, No. 10, pp. 2146-2154 (2001).

Ramström, O. et al., "Synthesis and Catalysis by Molecularly Imprinted Materials," *Current Opinion in Chemical Biology*, vol. 3, pp. 759-764 (1999).

Shao, Y. et al., "Sequence-Selective Receptors of Peptides, A Simple Molecular Design for Construction of Large Combinatorial Libraries of Receptors," *J. Org. Chem.*, vol. 61, No. 18, pp. 6086-6087 (1996).

Shellenberger, K. et al., "Effect of Molecular Scale Roughness of Glass Beads on Colloidal and Bacterial Deposition," *Environ. Sci. Technol.*, vol. 36, No. 2, pp. 184-189 (2002).

Shinoda, S. et al., "Ester-Armed Cyclens Having Quadruplicated Helical Geometry: Remarkably Stable and Selective Encapsulation of $Na^+$ Ion," *J. Org. Chem.*, vol. 66, No. 18, pp. 6104-6108 (2001).

Sternson, S. et al., "Split-Pool Synthesis of 1,3-Dioxanes Leading to Arrayed Stock Solutions of Single Compounds Sufficient for Multiple Phenotypic and Protein-Binding Assays," *J. Am. Chem. Soc.*, vol. 123, No. 8, pp. 1740-1747 (2001).

Wang, Y. et al., "Identification of Chiral Selectors from a 200-Member Parallel Combinatorial Library," *Anal. Chem.*, vol. 72, No. 21, pp. 5459-5465 (Nov. 1, 2000).

Way, J., "Covalent Modification as a Strategy to Block Protein-Protein Interactions with Small-Molecule Drugs," *Current Opinion in Chemical Biology*, vol. 4, pp. 40-46 (2000).

Winssinger, N. et al., "From Split-Pool Libraries to Spatially Addressable Microarrays and its Application to Functional Proteomic Profiling," *Angew. Chem. Int. Ed.*, vol. 40, No. 17, pp. 3152-3155 (2001).

Xu, R. et al., "Combinatorial Library Approach for the Identification of Synthetic Receptors Targeting Vancomycin-Resistant Bacteria," *J. Am. Chem. Soc.*, vol. 121, No. 20, pp. 4898-4899 (1999).

Yan, B. et al., "Crucial Factors Regulating Site Interactions in Resin Supports Determined by Single Bead IR," *J. Org. Chem.*, vol. 63, No. 1, pp. 55-58 (1998).

Zhu, H. et al., "Protein Arrays and Microarrays," *Current Opinion in Chemical Biology*, vol. 5, pp. 40-45 (2001).

Zhuravlev, N. et al., "Surface Coverages of Bonded-Phase Ligands on Silica: A Computational Study," *Anal. Chem.*, vol. 73. No. 16, pp. 4006-4011 (Aug. 15, 2001).

Zimmerman, S. et al., "Model Systems," *Current Opinion in Chemical Biology*, vol. 3, pp. 711-713 (1999).

Bachhawat-Sikder, K. et al., "Mixed-Element Capture Agents: A simple Strategy for the Construction of Synthetic, High-Affinity Protein Capture Ligands", *J. Am. Chem. Soc.*, 125:9550-9551 (2003).

Chambers, R. et al., "High-level generation of polyclonal antibodies by genetic immunization", *Nature Biotechnology*, 21(9):1088-1092 (Sep. 2003).

Kodadek, T., "Protein microarrays: prospects and problems", *Chemistry & Biology*, 8:105-115 (2001).

Olivos, H. et al., "Microwave-Assisted Solid-Phase Synthesis of Peptoids", *Organic Letters*, 4(23):4057-4059 (2002).

CARA presented Sep. 10, 2003.

"Various Search Reports," 73 pages (2004).

Burns, C. et al., "Components for Tethered Bilayer Membranes: Synthesis of Hydrophilically Substituted Phytanol Derivatives", *Aust. J. Chem.*, vol. 54, pp. 431-438 (2001).

Francis, M. et al., "Combinatorial Approach to the Discovery of Novel Coordination Complexes", *J. Am. Chem. Soc.*, vol. 37, No. 118, pp. 8983-8984 (1996).

Goodman, M. et al., "A Combinatorial Library Approach to Artificial Receptor Design", *J. Am. Chem. Soc.*, vol. 117, No. 46, pp. 11610-11611 (1995).

Halter, M. et al., "Engineered Lipids That Cross-Link the Inner and Outer Leaflets of Lipid Bilayers", *Langmuir*, vol. 20, No. 6, pp. 2416-2423 (2004).

Leigh, D., "Summing Up Ligand Binding Interactions", *Chemistry & Biology*, vol. 10, pp. 1143-1144 (Dec. 2003).

Malin, R. et al., "Identification of Technetium-99m Binding Peptides Using Combinatorial Cellulose-Bound Peptide Libraries", *J. Am. Chem. Soc.*, vol. 117, No. 47, pp. 118821-118822 (1995).

Sasaki, D., "Control of Membrane Structure and Organization Through Chemical Recognition", *Cell Biochemistry and Biophysics*, Vo. 39, pp. 145-161 (2003).

Song, X, "Direct, Ultrasensitive, and Selective Optical Detection of Protein Toxins Using Multivalent Interactions", *Anal. Chem.*, vol. 71, No. 11, pp. 2097-2107 (Jun. 1, 1999).

International Search Report dated May 27, 2004.

Korbel, G. et al., "A Method for Rapidly Determining the Enantiomeric Excess of Thousands of Samples", *J. Am. Chem. Soc.*, 123:361-362 (2001).

Lindsley, C. et al., "Solid-Phase Biomimetic Synthesis of Carpanone-like Molecules", *J. Am. Chem. Soc.*, 122:422-423 (2000).

Linton, B. et al., "Host-guest chemistry: combinatorial receptors", *Current Opinion in Chemical Biology*, 3:307-312 (1999).

Pickens, J. et al., "Anchor-Based Design of Improved Cholera Toxin and *E. Coli* Heat-Labile Enterotoxin Receptor Binding Antagonists that Display Multiple Binding Modes", *Chemistry & Biology*, 9:215-224 (2002).

Rodriguez, M. et al., "An Oriented Peptide Array Library (OPAL) Strategy to Study Protein-Protein Interactions", *The Journal of Biological Chemistry*, 279(10):8802-8807 (2004).

Sasaki, D. et al., "Crown Ether Functionalized Lipid Membranes: Lead Ion Recognition and Molecular Reorganization", *Langmuir*, 18:3714-3721 (2002).

Sasmai, S. et al., "Facile Purification of Rare Cucurbiturils by Affinity Chromatography", *Organic Letters*, 6(8):1225-1228,(2004).

Srinivasan, N. et al., "Combinatorial approaches to synthetic receptors", *Current Opinions in Chemical Biology*, 8:305-310 (2004).

Tomalia, D., "Birth of a New Macromolecular Architecture: Dendrimers as Quantized Building Blocks for Nanoscale Synthetic Organic Chemistry", *Aldrichimica ACTA*, 37(2): 39-57 (2004).

Alberti, P. et al., "DNA duplex-quadruplex exchange as the basis for a nanomolecular machine," *PNAS*, vol. 100, No. 4, pp. 1569-1573 (Feb. 18, 2003).

Noji, H. et al. "Direct observation of the rotation of $F_1$-ATPase," *Nature*, vol. 386, pp. 299-302 (Mar. 1997).

Yurke, B. et al., "A DNA-fuelled molecular machine made of DNA," *Nature*, vol. 406, pp. 605-608 (Aug. 10, 2000).

International Search Report dated Mar. 7, 2005.

International Search Report dated Mar. 9, 2005.

Barbaro, A. et al., "CHEMFET Devices for Biomedical and Environmental Applications", *Advanced Materials*, 4(6):402-408 (1992).

International Search Report dated Apr. 28, 2005.

International Search Report dated May 3, 2005.

DeLong, S. et al., "Covalently immobilized gradients of bFGF on hydrogel scaffolds for directed cell migration", *Biomaterials*, 26:3227-3234 (2005).

Dertinger, S. et al., "Gradients of substrate-bound laminin orient axonal specification of neurons", *PNAS*, 99(20):12542-12547 (2002).

Hypolite, C. et al., "Formation of Microscale Gradients of Protein using Heterobifunctional Photolinkers", *Bioconjugate Chem.*, 8:658-663 (1997).

Kramer, S. et al., "Preparation of Protein Gradients through the Controlled Deposition of Protein-Nanoparticle Conjugates onto Functionalized Surfaces", *J. Am. Chem. Soc.*, 126:5388-5395 (2004).

International Search Report dated Sep. 8, 2005.

Olivos, H. et al., "Quantum Dots as a Visual Aid for Screening Bead-Bound Combinatorial Libraries", Center for Biomedical inventions and the Departments of Internal Medicine and Molecular Biology, University of Texas Southwestern Medical Center, Dallas, Texas, preprint received by Sep. 2005.

Alluri, P. et al., "Isolation of Protein Ligands from Large Peptoid Libraries", J. Am. Chem. Soc. 2003, 125, 13995-14004.

International Search Report mailed Mar. 8, 2006.

Adams et al., "Oligosaccharide and Glycoprotein Microarrays as Tools in HIV Glycobiology: Glycan-Dependent gp120/Protein Interactions," *Chemistry & Biology*, vol. 11, 875-881, Jun. 2004.

Bryan et al., "Saccharide Display on Microtiter Plates," *Chemistry & Biology*, vol. 9, 713-720, Jun. 2002.

Bryan et al., "Covalent Display of Oligosaccharide Arrays in Microtiter Plates," *J. Am. Chem. Soc.* 2004, 126, 8640-8641.

Cho et al., "Pin-Printed Chemical Sensor Arrays for Simultaneous Multianalyte Quantification," *Anal. Chem.* 2002, 74, 1462-1466.

Collins et al., "Cell Surface Biology Mediated by Low Affinity Multivalent Protein-Glycan Interactions," *Current Opinion in Chemical Biology*, 2004,8:617-625.

Disney et al., "Aminoglycoside Microarrays to Study Antibiotic Resistance," *Angrew. Chem. Int. Ed.* 2004, 43, 1591-1594.

Disney et al., "Aminoglycisde Microarrays to Explore Interactions of Antibiotics with RNAs and Proteins," *Chem. Eur J.*, 2004, 10, 3308-3314.

Disney et al., "The Use of Carbohydrate Microarrays to Study Carbohydrate-Cell Interactions and to Detect Pathogens," *Chemistry & Biology*, vol. 11, 1701-1707, Dec. 2004.

Fukui et al., "Oligosaccharide Microarrays for High-Throughput Detection and Specificity Assignmetns of Carbohydrate-Protein Interactions," *Nature Biotechnology*, Oct. 2002, vol. 20, 1011-1017.

Houseman et al., "Carbohydrate Arrays for the Evaluation of Protein Binding and Enzymatic Modification," *Chemistry & Biology*, vol. 9, 443-454, Apr. 2002.

Kuruvilla et al., "Dissecting Glucose Signalling with Diversity-Oriented Synthesis and Small-Molecule Microarrays," *Nature*, vol. 416, Apr. 2002, 653-657.

Mahal, "Catching Bacteria with Sugar," *Chemistry & Biology*, vol. 11, Dec. 2004.

Mellet et al., "Carbohydrate Microarrays," *ChemBioChem*, 2002, 3, 819-822.

Michael et al., "Randomly Ordered Addressable High-Density Optical Sensor Arrays," *Anal. Chem.*, 1998, 70, 1242-1248.

Ni et al., "Synthesis of Maleimide-Activated Carbohydrates as Chemoselective Tags for Site-Specific Glycosylation of Peptides and Proteins," *Bioconjugate Chem.*, 2003, 14, 232-238.

Nimrichter et al., "Intact Cell Adhesion to Glycan Microarrays," *Glycobiology*, vol. 14, No. 2, pp. 197-203, 2004.

Ratner et al., "Probing Protein-Carbohydrate Interactions with Microarrays of Synthetic Oligosaccharides," *ChemBioChem*, 2004, 5, 379-383.

Aguilar, Z. et al., "Self-Contained Microelectrochemical Immunoassay for Small Volumes Using Mouse IgG as a Model System," *Anal. Chem.*, vol. 74, No. 14, pp. 3321-3329 (Jul. 15, 2002).

Ainsworth, S., "Nanotech IP: As nanometer-scale materials start making money, intellectual property issues are heating up," *Chemical & Engineering News*, vol. 82, No. 15, pp. 17-22 (Apr. 12, 2004).

Albert, K. et al., "Cross-Reactive Chemical Sensor Arrays," *Chemical Reviews*, vol. 100, No. 7, opp. 2595-2626 (2000).

Aziz, H., "Route to Carbon Nanotube Solubilization and Applications," *Dept. of Chem., Duke University, for Chem 100*, pp. 1-15, Submitted Nov. 25, 2003.

Bakker, E., "Electrochemical Sensors," *Anal. Chem.*, vol. 76, No. 12, pp. 3285-3298 (Jun. 15, 2004).

Ball, P., "Yarn spun from nanotubes," *Nature*, http://www.nature.com/nsu/040308/040308-10.html, (Mar. 12, 2004).

Basabe-Desmonts, L. et al., "A Simple Approach to Sensor Discovery and Fabrication on Self-Assembled Monolayers on Glass," *J. Am. Chem. Soc.*, vol. 126, No. 23, pp. 7293-7299 (2004).

Caswell, K. et al., "Preferential End-to-End Assembly of Gold Nanorods by Biotin-Streptavidin Connectors," *J. Am. Chem. Soc.*, vol. 125, No. 46, pp. 13914-13915 (2003).

Chen, J. et al., "Biased Combinatorial Libraries: Novel Ligands for the SH3 Domain of Phosphatidylinositol 3-Kinase," *J. Am. Chem. Soc.*, vol. 115, No. 26, pp. 12591-12592 (1993).

International Search Report dated Feb. 9, 2006.

International Search Report mailed Mar. 14, 2006.

Dai, Z. et al., "Reagentless Amperometric Immunosensors Based on Direct Electrochemistry of Horseradish Peroxidase for Determination of Carcinoma Antigen-125," *Anal. Chem.*, vol. 75, No. 20, pp. 5429-5434 (Oct. 15, 2003).

Developing Nano, http://www.nanosysinc.com/technology.html, pp. 1-12 (May 3, 2004).

Diamond, D., "Internet-Scale Sensing," *Analytical Chemistry*, vol. 76, No. 15, pp. 279A-286A (Aug. 1, 2004).

Ellman, J. et al., "Combinatorial thinking in chemistry and biology," *Proc. Natl. Acad. Sci. USA*, vol. 94, pp. 2779-2782 (Apr. 1997).

Feder, B., "Bashful vs. Brash in the New Field of Nanotech," *The New York Times*, 5 pages, http://www.nytimes.com/2004/03/15/technology/15nano.html?ei=1&en=873c8a6f53eb2287&ex=1080357865&adxnnl..., (Mar. 15, 2004).

Furlan, R. et al., "A New Cyclic Pseudopeptide Receptor for $Li^+$ from a Dynamic Combinatorial Library," *J. Am. Chem. Soc.*, vol. 123, No. 36, pp. 8876-8877 (2001).

Grabar, K. et al., "Two-Dimensional Arrays of Colloidal Gold Particles: A Flexible Approach to Macroscopic Metal Surfaces", *Langmuir*, 12:2353-2361 (1996).

Grant, S. et al., "Labeless and reversible immunosensor assay based upon an electrochemical current-transient protocol," *Analytica Chimica Acta*, vol. 495, pp. 21-32 (2003).

Grennan, K. et al., "Atrazine analysis using an amperometric immunosensor based on single-chain antibody fragments and regeneration-free multi-calibrant measurement," *Analytica Chimica Acta*, vol. 500, pp. 287-298 (2003).

Gwynne, P. et al., "Proteomics 3: Probing Proteins' Structures," *Drug Discovery and Biotechnology Trends*, pp. 689-699 (Jul. 30, 2004).

Jacoby, M., "Chiral Catalysis at Surfaces," *C & EN*, pp. 37-41 (Mar. 15, 2004).

Kimura, M. et al., "Construction of Regulated Nanospace around a Porphyrin Core," *J. Am. Chem. Soc.*, vol. 123, No. 24, pp. 5636-5642 (2001).

Kojima, K. et al., "Electrochemical Protein Chip with Arrayed Immunosensors with Antibodies Immobilized in a Plasma-Polymerized Film," *Anal. Chem.*, vol. 75, No. 5, pp. 1116-1122 (Mar. 1, 2003).

Lavigne, J. et al., "Sensing a Paradigm Shift in the Field of Molecular Recognition: From Selective to Differential Receptors," *Angew. Chem. Int. Ed.*, vol. 40, pp. 3118-3130 (2001).

Lindsley, C. et al., "Solid-Phase Biomimetic Synthesis of Carpanone-like Molecules," *J. Am. Chem. Soc.*, vol. 122, No. 2, pp. 422-423 (2000).

Morgenthaler, S. et al., "Surfaces with a Hydrophobicity Gradient: Possible Applications in Biological Testing", European Cells and Materials, 6(1):69 (2001).

Naffin, J. et al., "Immobilized Peptides as High-Affinity Capture Agents for Self-Associating Proteins", Chemistry & Biology, 10:251-259 (2003).

Ruardy, T. et al., "Preparation and characterization of chemical gradient surfaces and their application for the study of cellular interaction phenomena", Surface Science Reports, 29:1-30 (1997).

Sadik, O. et al., "Differential Impedance Spectroscopy for Monitoring Protein Immobilization and Antibody-Antigen Reactions," *Anal. Chem.*, vol. 74, No. 13, pp. 3142-3150 (Jul. 1, 2002).

Wolfbeis, O., "Fiber-Optic Chemical Sensors and Biosensors," *Anal. Chem.*, vol. 76, No. 12, pp. 3269-3283 (Jun. 15, 2004).

Worsley, K. et al., "Long-Range Periodicity in Carbon Nanotube Sidewall Functionalization," *Nano Letters*, vol. 4, No. 8, pp. 1541-1546 (2004).

Wu, Z. et al., "Transparent, Conductive Carbon Nanotube Films," *Science*, vol. 305, pp. 1273-1276 (Aug. 27, 2004).

Zhang, Z. et al., "Self-Assembly of Patchy Particles," *Nano Letters*, vol. 4, No. 8, pp. 1407-1413 (2004).

U.S. Appl. No. 10/703,876 Office Action Nov. 15, 2007.

U.S. Appl. No. 10/727,059 Office Action Nov. 15, 2007.

Non-proprietary Summary dated Nov. 29, 2001 that may have been sent to the Department of Defense and the National Institutes of Health.

U.S. Appl. No. 10/934,193 Office Action May 16, 2008.

U.S. Appl. No. 10/934,977 Office Action Apr. 8, 2008.

U.S. Appl. No. 11/004,593 Office Action Apr. 14, 2008.

U.S. Appl. No. 11/217,384 Office Action Apr. 29, 2008.

U.S. Appl. No. 11/219,515 Office Action Apr. 30, 2008.

European Search Report, Application No. 03709250.9 dated May 7, 2007.

Iorio et al., "Highly Sequence Selective Nonmacrocyclic Two-armed Receptors for Peptides," Bioorganic & Medicinal Chemistry Letters, Oxford, GB, vol. 9, No. 15, Aug. 2, 1999, pp. 2145-2150.

Iiorio et al., "Sequence-Selective Peptide Detection by Small Synthetic Chemosensors Selected from an Encoded Combinatorial Chemosensor Library," Bioorganic & Medicinal Chemistry Letters, Oxford, GB, vol. 11, No. 13, Jul. 9, 2001, pp. 1635-1638.

Nestler et al., "Combinatorial Libraries: Studies in Molecular Recognition," Combinatorial Chemistry and High Throughput Screening, Hilversum, NL, vol. 1, No. 3, Oct. 1998, pp. 113-126.

Still, "Discovery of Sequence-selective Peptide Binding by Synthetic Receptors Using Encoded Combinatorial Libraries," Accounts of Chemical Research, ACS, Washington, DC, US, vol. 29, 1996, pp. 155-163.

U.S. Appl. No. 10/244,727 Office Action (Jan. 25, 2006).
U.S. Appl. No. 10/244,727 Office Action (Feb. 8, 2006).
U.S. Appl. No. 10/244,727 Office Action (Feb. 12, 2007).
U.S. Appl. No. 10/244,727 Office Action (May. 17, 2007).
U.S. Appl. No. 10/244,727 Office Action (May 17, 2007).
U.S. Appl. No. 10/244,727 Office Action (Aug. 10, 2005).
U.S. Appl. No. 10/244,727 Office Action (Aug. 11, 2006).
U.S. Appl. No. 10/244,727 Office Action (Dec. 29, 2006).
U.S. Appl. No. 10/703,660 Office Action (Mar. 8, 2007).
U.S. Appl. No. 10/703,660 Office Action (Jun. 22, 2006).
U.S. Appl. No. 10/703,779 Office Action (Mar. 12, 2007).
U.S. Appl. No. 10/703,779 Office Action (Jun. 29, 2006).
U.S. Appl. No. 10/703,876 Office Action (Mar. 2, 2007).
U.S. Appl. No. 10/703,876 Office Action (Jun. 29, 2006).
U.S. Appl. No. 10/706,505 Office Action (Feb. 15, 2007).
U.S. Appl. No. 10/706,505 Office Action (Jun. 29, 2006).
U.S. Appl. No. 10/706,573 Office Action (Jan. 31, 2007).
U.S. Appl. No. 10/706,573 Office Action (Jun. 30, 2006).
U.S. Appl. No. 10/727,059 Office Action (Oct. 5, 2006).
U.S. Appl. No. 10/813,568 Office Action (Feb. 15, 2007).
U.S. Appl. No. 10/813,568 Office Action (Oct. 5, 2006).
U.S. Appl. No. 10/813,612 Office Action (Feb. 15, 2007).
U.S. Appl. No. 10/813,612 Office Action (Oct. 6, 2006).
U.S. Appl. No. 10/813,568 Office Action Jul. 27, 2007.
U.S. Appl. No. 10/813,612 Office Action Aug. 7, 2007.
U.S. Appl. No. 10/934,193 Office Action Jul. 27, 2007.
U.S. Appl. No. 10/934,865 Office Action Aug. 2, 2007.
U.S. Appl. No. 10/706,573 Office Action Oct. 18, 2007.
U.S. Appl. No. 10/706,573 Office Action Jul. 28, 2008.

* cited by examiner

2D TOP VIEW

2D SIDE VIEW

3D FRONT VIEW

6 POSITIONAL ISOMERS OF 4 BUILDING BLOCKS AT
VERTICES OF A QUADRILATERAL

POSITIONAL ISOMERS ON A SCAFFOLD

ISOMER "1"　　　　ISOMER "2"　　　　ISOMER "3"

PARTIAL 2D SIDE VIEW

RECEPTOR SITE

SUPPORT ARRAY

3D FRONT VIEW

Heterogeneous A/B Illustrated

Heterogeneous A/A Illustrated

Formula H1:

Formula H2:

Formula H3:

Formula H4:

Formula H5:

Formula H6:

US 7,504,364 B2

METHODS OF MAKING ARRAYS AND ARTIFICIAL RECEPTORS

CROSS REFERENCE TO RELATED APPLICATIONS

This application claims priority to U.S. Provisional Patent Application Ser. Nos. 60/360,980 filed Mar. 1, 2002; 60/362,600, filed Mar. 8, 2002; 60/375,655, filed Apr. 26, 2002; and 60/400,605, filed Aug. 2, 2002.

INTRODUCTION

The present invention relates to artificial receptors, to methods and compositions for making them, and to methods using them. A receptor provides a binding site for and binds a ligand. For example, at an elementary level, receptors are often visualized having a binding site represented as a lock or site into which a key or ligand fits. The binding site is lined with, for example, hydrophobic or functional groups that provide favorable interactions with the ligand.

The present invention provides compositions and methods for developing molecules that provide favorable interactions with a selected ligand. The present compositions and methods generate a wide variety of molecular structures, one or more of which interacts favorably with the selected ligand. Heterogeneous and immobilized combinations of building block molecules form the variety of molecular structures. For example, combinations of 2, 3, 4, or 5 distinct building block molecules immobilized near one another on a support provide molecular structures that serve as candidate and working artificial receptors. FIG. 1 schematically illustrates an embodiment employing 4 distinct building blocks in a spot on a microarray to make a ligand binding site. This Figure illustrates a group of 4 building blocks at the corners of a square forming a unit cell. A group of four building blocks can be envisioned as the vertices on any quadrilateral. FIG. 1 illustrates that spots or regions of building blocks can be envisioned as multiple unit cells, in this illustration square unit cells. Groups of unit cells of four building blocks in the shape of other quadrilaterals can also be formed on a support.

Each immobilized building block molecule can provide one or more "arms" extending from a "framework" and each can include groups that interact with a ligand or with portions of another immobilized building block. FIG. 2 illustrates that combinations of four building blocks, each including a framework with two arms (called "recognition elements"), provides a molecular configuration of building blocks that form a site for binding a ligand. Such a site formed by building blocks such as those exemplified below can bind a small molecule, such as a drug, metabolite, pollutant, or the like, and/or can bind a larger ligand such as a macromolecule or microbe.

BACKGROUND

The preparation of artificial receptors that bind ligands like proteins, peptides, carbohydrates, microbes, pollutants, pharmaceuticals, and the like with high sensitivity and specificity is an active area of research. None of the conventional approaches has been particularly successful; achieving only modest sensitivity and specificity mainly due to low binding affinity.

Antibodies, enzymes, and natural receptors generally have binding constants in the $10^8$-$10^{12}$ range, which results in both nanomolar sensitivity and targeted specificity. By contrast, conventional artificial receptors typically have binding constants of about $10^3$ to $10^5$, with the predictable result of millimolar sensitivity and limited specificity.

Several conventional approaches are being pursued in attempts to achieve highly sensitive and specific artificial receptors. These approaches include, for example, affinity isolation, molecular imprinting, and rational and/or combinatorial design and synthesis of synthetic or semi-synthetic receptors.

Such rational or combinatorial approaches have been limited by the relatively small number of receptors which are evaluated and/or by their reliance on a design strategy which focuses on only one building block, the homogeneous design strategy. Common combinatorial approaches form microarrays that include 10,000 or 100,000 distinct spots on a standard microscope slide. However, such conventional methods for combinatorial synthesis provide a single molecule per spot. Employing a single building block in each spot provides only a single possible receptor per spot. Synthesis of thousands of building blocks would be required to make thousands of possible receptors.

Further, these conventional approaches are hampered by the currently limited understanding of the principals which lead to efficient binding and the large number of possible structures for receptors, which makes such an approach problematic.

There remains a need for methods and materials for making artificial receptors that combines the efficiency of targeted synthesis, the spatial resolution of microarrays, and the exponential power of combinatorial display.

SUMMARY

The present invention relates to artificial receptors, arrays or microarrays of artificial receptors or candidate artificial receptors, and methods of making them. Each member of the array includes a plurality of building block compounds, typically immobilized in a spot on a support. The present invention also includes the building blocks, combinations of building blocks, arrays of building blocks, and receptors constructed of these building blocks together with a support. The present invention also includes methods of using these arrays and receptors.

The present invention includes and employs combinations of small, selected groups of building blocks in a combinatorial microarray display format to provide candidate artificial receptors. In an embodiment, the present invention employs up to about 4 building blocks, to make a candidate artificial receptor. Combinations of these building blocks can be positioned on a substrate in configurations suitable for binding ligands such as proteins, peptides, carbohydrates, pollutants, pharmaceuticals, chemical warfare agents, microbes, and the like.

The present artificial receptors can be prepared by methods including both focused combinatorial synthesis and targeted screening arrays. The present compositions and methods can combine the advantages of receptor focused synthesis and high throughput evaluation to rapidly identify and produce practical, target specific artificial receptors.

In an embodiment, the present invention includes a method of making a heterogeneous building block array. This method includes forming a plurality of spots on a solid support, the spots including a plurality of building blocks, and coupling a plurality of building blocks to the solid support in the spots.

In an embodiment, the present invention includes a method of using an artificial receptor. This method includes contacting a heterogeneous building block array with a test ligand, detecting binding of a test ligand to one or more spots in the array, and selecting one or more of the binding spots as the artificial receptor. The artificial receptor can be a lead or working artificial receptor. The method can also include testing a plurality of building block arrays.

In an embodiment, the present invention includes a composition including a support with a portion of the support comprising a plurality of building blocks. The building blocks are coupled to the support. The composition can include or be an artificial receptor, a heterogeneous building block array, or a composition including a surface and a region on the surface.

In an embodiment, the present invention includes an artificial receptor including a plurality of building blocks coupled to a support.

In an embodiment, the present invention includes a heterogeneous building block array. This array includes a support and a plurality of spots on the support. The spots include a plurality of building blocks. The building blocks are coupled to the support.

In an embodiment, the present invention includes a composition including a surface and a region on the surface. This region includes a plurality of building blocks, the building blocks being coupled to the support.

In an embodiment, the present invention includes a composition of matter including a plurality of building blocks.

In an embodiment, the building blocks include framework, linker, first recognition element, and second recognition element or have a formula linker-framework-(first recognition element)(second recognition element). The framework can be an amino acid. The building block can have the formula:

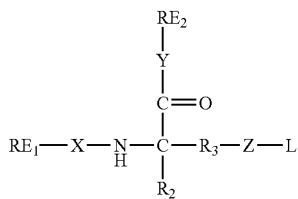

in which: X, Y, Z, $R_2$, $R_3$, $RE_1$, $RE_2$ and L are described hereinbelow.

DETAILED DESCRIPTION

Definitions

Figure 1:
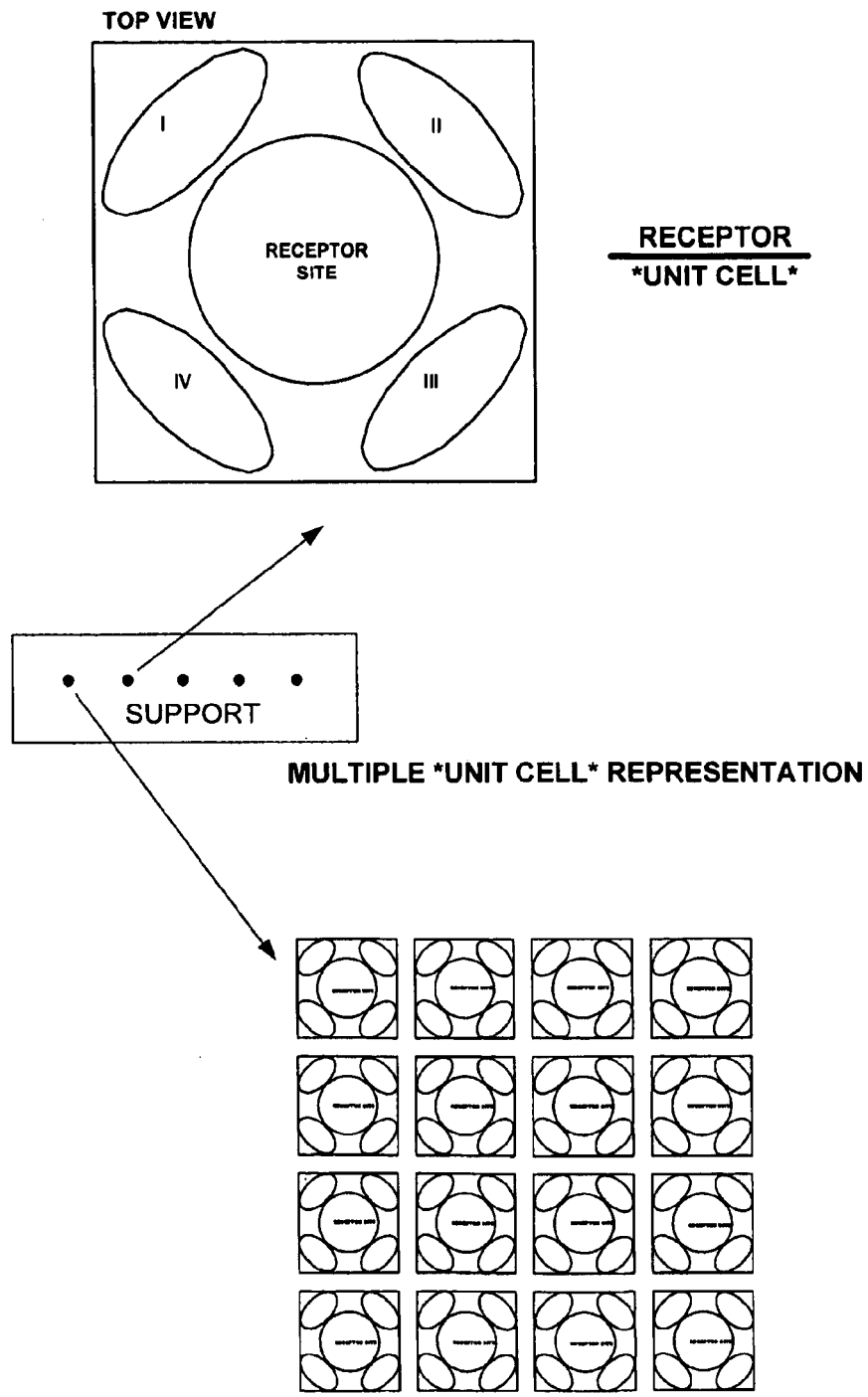
FIG. 1 schematically illustrates two dimensional representations of an embodiment of a receptor according to the present invention that employs 4 different building blocks to make a ligand binding site.
Figure 2:
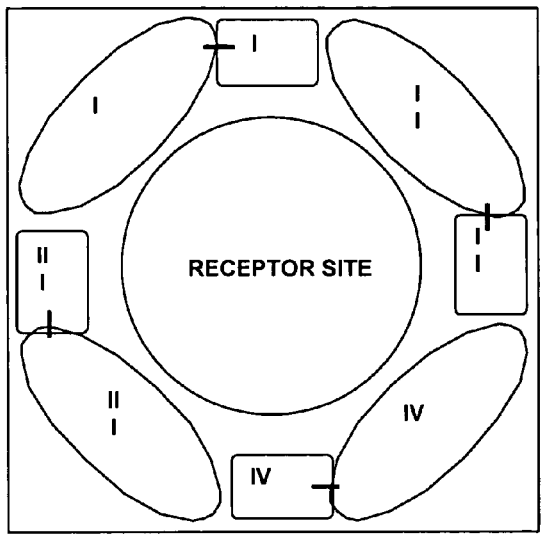
FIG. 2 schematically illustrates two and three dimensional representations of an embodiment of a molecular configuration of 4 building blocks, each building block including a recognition element, a framework, and a linker coupled to a support (immobilization/anchor).
Figure 2:
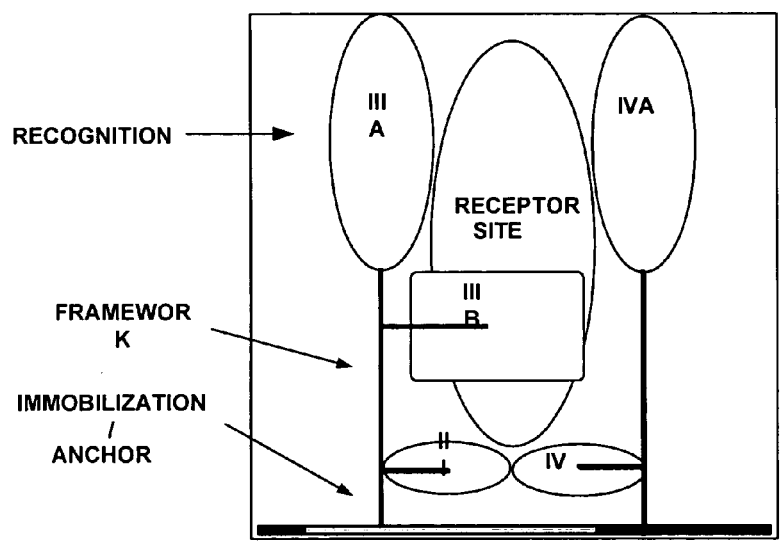
Figure 2:
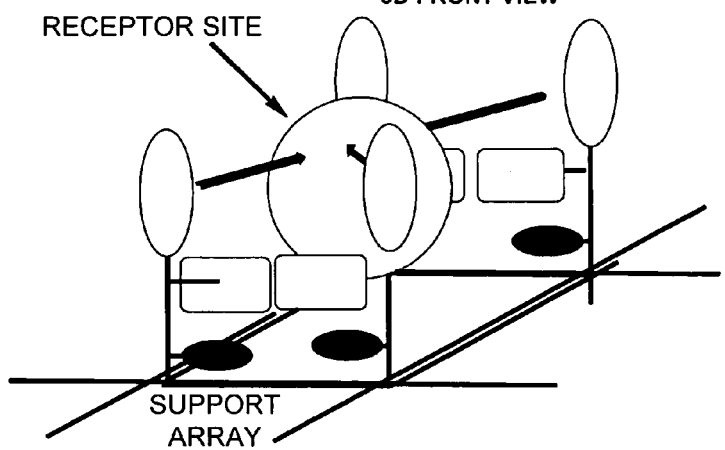

A combination of building blocks immobilized on, for example, a support can be a candidate artificial receptor, a lead artificial receptor, or a working artificial receptor. That is, a heterogeneous building block spot on a slide or a plurality of building blocks coated on a tube or well can be a candidate artificial receptor, a lead artificial receptor, or a working artificial receptor. A candidate artificial receptor can become a lead artificial receptor, which can become a working artificial receptor.

As used herein the phrase "candidate artificial receptor" refers to an immobilized combination of building blocks that can be tested to determine whether or not a particular test ligand binds to that combination. In an embodiment, the candidate artificial receptor can be a heterogeneous building block spot on a slide or a plurality of building blocks coated on a tube or well.

As used herein the phrase "lead artificial receptor" refers to an immobilized combination of building blocks that binds a test ligand at a predetermined concentration of test ligand, for example at 10, 1, 0.1, or 0.01 µg/ml, or at 1, 0.1, or 0.01 ng/ml. In an embodiment, the lead artificial receptor can be a heterogeneous building block spot on a slide or a plurality of building blocks coated on a tube or well.

As used herein the phrase "working artificial receptor" refers to a combination of building blocks that binds a test ligand with a selectivity and/or sensitivity effective for categorizing or identifying the test ligand. That is, binding to that combination of building blocks describes the test ligand as belonging to a category of test ligands or as being a particular test ligand. A working artificial receptor can, typically, bind the ligand at a concentration of, for example, 100, 10, 1, 0.1, 0.01, or 0.001 ng/ml. In an embodiment, the working artificial receptor can be a heterogeneous building block spot on a slide or a plurality of building blocks coated on a tube, well, slide, or other support or on a scaffold.

As used herein the phrase "working artificial receptor complex" refers to a plurality of artificial receptors, each a combination of building blocks, that binds a test ligand with a pattern of selectivity and/or sensitivity effective for categorizing or identifying the test ligand. That is, binding to the several receptors of the complex describes the test ligand as belonging to a category of test ligands or as being a particular test ligand. The individual receptors in the complex can each bind the ligand at different concentrations or with different affinities. Typically, the individual receptors in the complex each bind the ligand at concentrations of 100, 10, 1, 0.1, 0.01 or 0.001 ng/ml. In an embodiment, the working artificial receptor complex can be a plurality of heterogeneous building block spots or regions on a slide; a plurality of wells, each coated with a different combination of building blocks; or a plurality of tubes, each coated with a different combination of building blocks.

As used herein, the term "building block" refers to a molecular component of an artificial receptor including portions that can be envisioned as or that include one or more linkers, one or more frameworks, and one or more recognition elements. In an embodiment, the building block includes a linker, a framework, and one or more recognition elements. The building block interacts with the ligand.

As used herein, the term "linker" refers to a portion of or functional group on a building block that can be employed to or that does couple the building block to a support, for example, through a covalent link or electrostatic interactions.

As used herein, the term "framework" refers to a portion of a building block including the linker or to which the linker is coupled and to which one or more recognition elements are coupled.

As used herein, the term "recognition element" refers to a portion of a building block coupled to the framework but not covalently coupled to the support. Although not limiting to the present invention, the recognition element typically provides or forms one or more groups, surfaces, or spaces for interacting with the ligand.

As used herein, the phrase "plurality of building blocks" refers to two or more building blocks of different structure in a mixture, in a kit, or on a support or scaffold. Each building block has a particular structure, and use of building blocks in the plural, or of a plurality of building blocks, refers to more than one of these particular structures. Building blocks or plurality of building blocks does not refer to a plurality of molecules each having the same structure.

As used herein, the phrase "combination of building blocks" refers to a plurality of building blocks that together are in a spot, region, or a candidate, lead, or working artificial receptor. A combination of building blocks can be a subset of a set of building blocks. For example, a combination of building blocks can be one of the possible combinations of 2, 3, 4, 5, or 6 building blocks from a set of N (e.g., N=10-200) building blocks.

As used herein, the phrases "homogenous immobilized building block" and "homogenous immobilized building blocks" refer to a support or spot having immobilized on or within it only a single building block.

As used herein, the phrase "activated building block" refers to a building block activated to make it ready to form a covalent bond to a functional group, for example, on a support. A building block including a carboxyl group can be converted to a building block including an activated ester group, which is an activated building block. An activated building block including an activated ester group can react, for example, with an amine to form a covalent bond.

As used herein, the term "immobilized" used with respect to building blocks coupled to a support refers to building blocks being stably oriented on the support so that they do not migrate on the support. Building blocks can be immobilized by covalent coupling, by ionic interactions, or by electrostatic interactions, such as ion pairing.

As used herein a "region" of a support, tube, well, or surface refers to a contiguous portion of the support, tube, well, or surface. Building blocks coupled to a region typically refers to building blocks in proximity to one another in that region.

As used herein, a "bulky" group on a molecule is larger than a moiety including 7 or 8 carbon atoms.

As used herein, a "small" group on a molecule is hydrogen, methyl, or another group smaller than a moiety including 4 carbon atoms.

As used herein, the term "lawn" refers to a layer, spot, or region of functional groups on a support, typically, at a density sufficient to place coupled building blocks in proximity to one another.

The term "alkyl" refers to saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has 30 or fewer carbon atoms in its backbone (e.g., $C_1$-$C_{12}$ for straight chain, $C_1$-$C_6$ for branched chain). Likewise, cycloalkyls typically have from 3-10 carbon atoms in their ring structure, and preferably have 5, 6 or 7 carbons in the ring structure.

The term "alkyl" as used herein refers to both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an ester, a formyl, or a ketone), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aryl alkyl, or an aromatic or heteroaromatic moiety. The moieties substituted on the hydrocarbon chain can themselves be substituted, if appropriate. For example, the substituents of a substituted alkyl can include substituted and unsubstituted forms of the groups listed above.

The phrase "aryl alkyl", as used herein, refers to an alkyl group substituted with an aryl group (e.g., an aromatic or heteroaromatic group).

The terms "alkenyl" and "alkynyl" refer to unsaturated aliphatic groups analogous in length and optional substitution to the alkyls groups described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with such substituents such as those described above for alkyl groups. The term "aryl" also includes polycyclic ring systems having two or more cyclic rings in which two or more carbons are common to two adjoining rings (the rings are "fused rings") wherein at least one of the rings is aromatic, e.g., the other cyclic ring(s) can be cycloalkyls, cycloalkenyls, cycloalkynyls, aryls and/or heterocyclyls.

The terms "heterocyclyl" or "heterocyclic group" refer to 3- to 12-membered ring structures, more preferably 3- to 7-membered rings, whose ring structures include one to four heteroatoms. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents such as those described for alkyl groups.

The term "heteroatom" as used herein means an atom of any element other than carbon or hydrogen, such as nitrogen, oxygen, sulfur and phosphorous.

Methods of Making and Using an Artificial Receptor

Making the Artificial Receptors

The present invention relates to a method of making an artificial receptor or a candidate artificial receptor. In an embodiment, this method includes preparing a spot or region on a support, the spot or region including a plurality of building blocks immobilized on the support. The method can include forming a plurality of spots on a solid support, each spot including a plurality of building blocks, and coupling a plurality of building blocks to the solid support in each spot. In an embodiment, an array of such spots is referred to as a heterogeneous building block array.

The building blocks can be activated to react with a functional group on the support. Coupling can occur spontaneously after forming the spot of the building block or activated building block. The method can include mixing a plurality of activated building blocks and employing the mixture in forming the spot(s). Alternatively, the method can include spotting individual activated building blocks on the support.

Forming a spot on a support can be accomplished by methods and apparatus such as pin spotters (sometimes referred to as printers), which can, for example, spot 10,000 to more than 100,000 spots on a microscope slide. Other spotters include piezoelectric spotters (similar to ink jets) and electromagnetic spotters that can also spot, for example, 10,000 to more than 100,000 spots on a microscope slide. Conventional mixing valves or manifolds can be employed to mix the activated building blocks before spotting. These valves or manifolds can be under control of conventional microprocessor based controllers for selecting building blocks and amounts of reagents.

Such spotting yields a microarray of spots of heterogeneous combinations of building blocks, each of which can be a candidate artificial receptor. Each spot in a microarray includes a statistically significant number of each building block. For example, although not limiting to the present invention, it is believed that each micro spot of a size sufficiently small that 100,000 fit on a microscope slide can include approximately 320 million clusters of 4 building blocks.

In an embodiment, the present method includes making a receptor surface. Making a receptor surface can include forming a region on a solid support, the region including a plurality of building blocks, and coupling the plurality of building blocks to the solid support in the region. The method can include mixing a plurality of activated building blocks and employing the mixture in forming the region or regions. Alternatively, the method can include applying individual activated building blocks in a region on the support. Forming a region on a support can be accomplished, for example, by soaking a portion of the support with the building block solution.

In an embodiment, a tube or well coated with a support matrix can be filled with activated building block (e.g., a solution containing activated building block), which couples to the support matrix. For example, the support can be a glass tube or well coated with a plurality of building blocks. The surface of the glass tube or well can be coated with a coating to which the plurality of building blocks become covalently bound. The resulting coating including building blocks can be referred to as including heterogeneous building blocks.

Preferably, the method produces a surface or coating with a density of building blocks sufficient to provide interactions of more than one building block with a ligand. That is, the building blocks can be in proximity to one another. Proximity of different building blocks can be detected by determining different (preferably greater) binding of a test ligand to a surface including a plurality of building blocks compared to a surface or surfaces including only one of the building blocks.

The method can apply or spot building blocks onto a support in combinations of 2, 3, 4, or more building blocks. For an embodiment employing a bulky tube or well, a manageable set of building blocks preferably provides fewer than several hundred or several thousand combinations of building blocks. For example, in this context, a set of 4, 5, or 6 building blocks provides a manageable number of combinations of 2, 3, or 4 building blocks. In an embodiment, the method can be employed to produce a plurality of tubes each tube having immobilized on its surface a heterogeneous combination of building blocks.

In an embodiment, the present method can be employed to produce a solid support having on its surface a plurality of regions or spots, each region or spot including a plurality of building blocks. For example, the method can include spotting a glass slide with a plurality of spots, each spot including a plurality of building blocks. Such a spot can be referred to as including heterogeneous building blocks.

Each spot can include a density of building blocks sufficient to provide interactions of more than one building block with a ligand. Such interactions can be determined as described above for regions. The method typically includes spotting the building blocks so that each spot is separated from the others. A plurality of spots of building blocks is referred to herein as an array of spots.

In an embodiment, the method spots building blocks in combinations of 2, 3, 4, or more. The method can form up to 100,000 or more spots on a glass slide. Therefore, in this embodiment of the method, a manageable set of building blocks can provide several million combinations of building blocks. For example, in this context, a set of 81 building blocks provides a manageable number of (1.66 million) combinations of 4 building blocks. For convenience in limiting the number of slides employed in the method, in this embodiment a set includes up to 200 building blocks, preferably 50-100, preferably about 80 (e.g., 81) building blocks.

In an embodiment, the method includes forming an array of heterogeneous spots made from combinations of a subset of the total building blocks and/or smaller groups of the building blocks in each spot. That is, the method forms spots including only, for example, 2 or 3 building blocks, rather than 4 or 5. For example, the method can form spots from combinations of a full set of building blocks (e.g. 81 of a set of 81) in groups of 2 and/or 3. For example, the method can form spots from combinations of a subset of the building blocks (e.g., 25 of the set of 81) in groups of 4 or 5. For example, the method can form spots from combinations of a subset of the building blocks (e.g., 25 of the set of 81) in groups of 2 or 3. The method can include forming additional arrays incorporating building blocks, lead artificial receptors, or structurally similar building blocks.

In an embodiment, the method includes forming an array including one or more spots that function as controls for validating or evaluating binding to artificial receptors of the present invention. In an embodiment, the method includes forming one or more regions, tubes, or wells that function as controls for validating or evaluating binding to artificial receptors of the present invention. Such a control spot, region, tube, or well can include no building block, only a single building block, only functionalized lawn, or combinations thereof.

The method can couple building blocks to supports using known methods for activating compounds of the types employed as building blocks and for coupling them to supports. Covalent coupling can produce artificial receptors sufficiently durable to be used repeatedly over a period of months. The method can employ building blocks including activated esters and couple them to supports including amine functional groups. The method can include activating a carboxyl group on a building block by derivatizing to form the activated ester. By way of further example, the method can couple building blocks including amine functional groups to supports including carboxyl groups. Pairs of functional groups that can be employed on building blocks and supports according to the method include nucleophile/electrophile pairs, such as amine and carboxyl (or activated carboxyl), thiol and maleimide, alcohol and carboxyl (or activated carboxyl), mixtures thereof, and the like.

The support can include any functional group suitable for forming a covalent bond with a building block. The support or the building block can include a functional group such as alcohol, phenol, thiol, amine, carbonyl, or like group. The support or the building block can include a carboxyl, alcohol, phenol, thiol, amine, carbonyl, maleimide, or like group that can react with or be activated to react with the support or the building block. The support can include one or more of these groups. A plurality of building blocks can include a plurality of these groups.

The support or the building block can include a good leaving group bonded to, for example, an alkyl or aryl group. The leaving group being "good" enough to be displaced by the alcohol, phenol, thiol, amine, carbonyl, or like group on the support or the building block. Such a support or the building block can include a moiety represented by the formula: R—X, in which X is a leaving group such as halogen (e.g., —Cl, —Br, or —I), tosylate, mesylate, triflate, and R is alkyl, substituted alkyl, cycloalkyl, heterocyclic, substituted heterocyclic, aryl alkyl, aryl, heteroaryl, or heteroaryl alkyl. The support can include one or more of these groups. A plurality of building blocks can include a plurality of these groups.

The method can employ any of the variety of known supports employed in combinatorial or synthetic chemistry (e.g., a microscope slide, a bead, a resin, a gel, or the like). Suitable supports include functionalized glass, such as a functionalized slide or tube, glass microscope slide, glass plate, glass coverslip, glass beads, microporous glass beads, microporous polymer beads (e.g. those sold under the tradename Stratospheres™), silica gel supports, and the like.

The support typically includes a support matrix of a compound or mixture of compounds having functional groups suitable for coupling to a building block. The support matrix can be, for example, a coating on a microscope slide or functionalizing groups on a bead, gel, or resin. Known support matrices are commercially available and/or include linkers with functional groups that are coupled beads, gels, or resins. The support matrix functional groups can be pendant from the support in groups of one (e.g., as a lawn of amines, a lawn of another functional group, or a lawn of a mixture of functional groups) or in groups of, for example, 2, 3, 4, 5, 6, or 7. The groups of a plurality of functional groups pendant from the support can be visualized as or can be scaffold molecules pendant from the support.

Figure 3A:
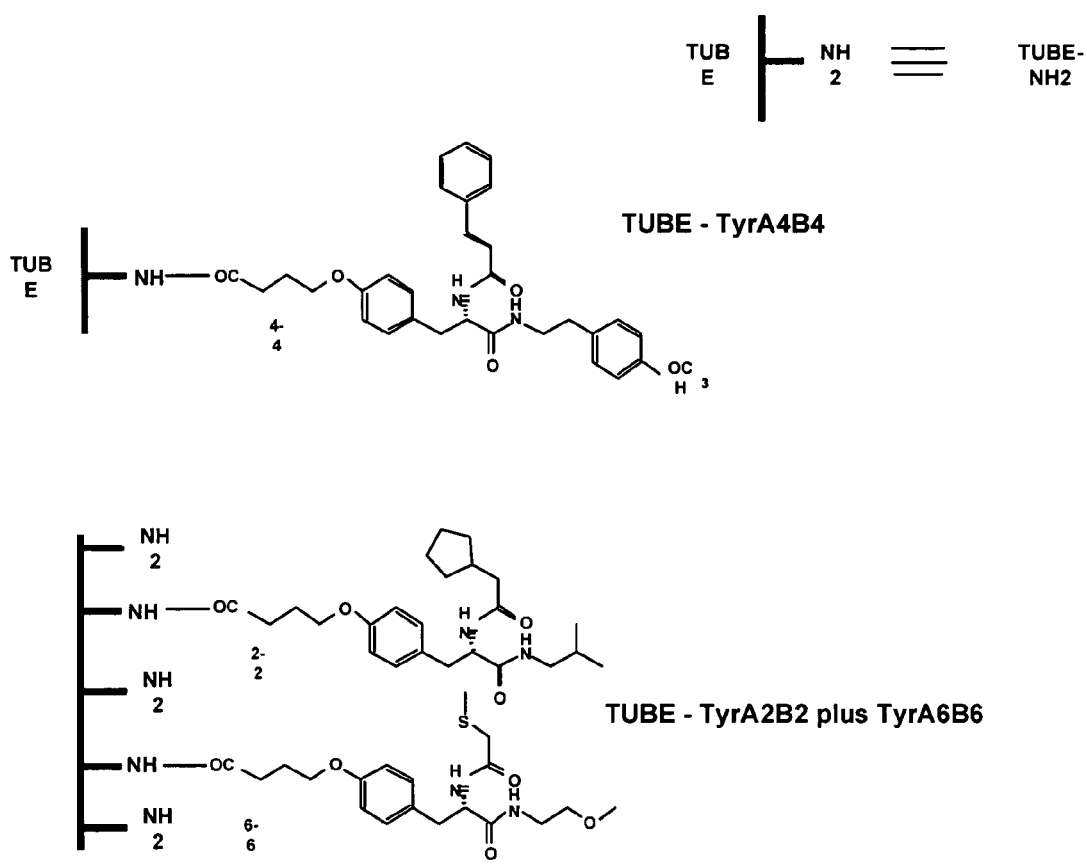
FIG. 3A schematically illustrates representative structures of the support floor and building blocks according to the present invention on a surface of a support.
Figure 3B:
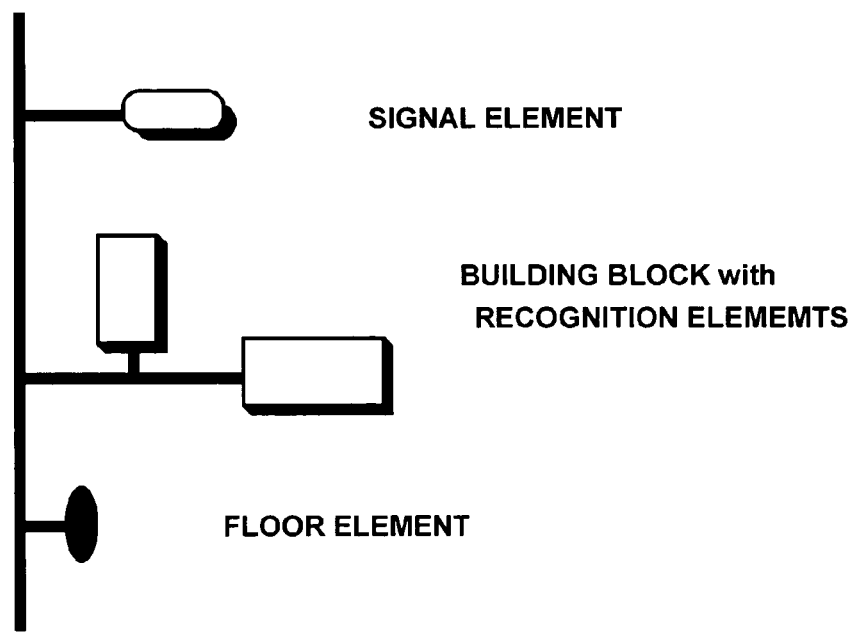
FIG. 3B schematically illustrates a support coupled to a signal element, a building block, and a modified floor element.
Figure 4:
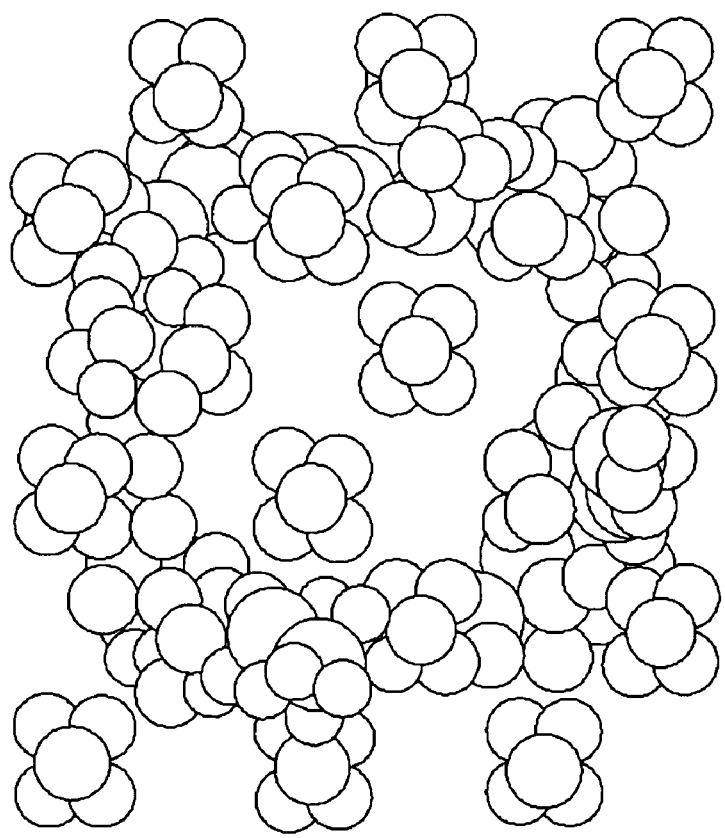
FIG. 4 schematically illustrates representative space filing structures of a candidate artificial receptor according to the present invention including both an amine floor and a four building block receptor.

The surface of the support can be visualized as including a floor and the building blocks (FIGS. 3A, 3B, and 4). As illustrated in FIG. 3A, addition of building blocks to an amine lawn can proceed through reaction of the amines to form building block amides with some of the amines remaining on the floor of the support or candidate artificial receptor. Thus, the floor can be considered a feature of the candidate artificial receptor. The floor or modified floor can interact with the ligand as part of the artificial receptor. The nucleophilic or electrophilic groups on the floor can be left unreacted in the artificial receptor, or they can be modified. The floor can be modified with a small group that alters the recognition properties of the floor (FIG. 3B). The floor can be modified with a signal element that produces a detectable signal when a test ligand is bound to the receptor (FIG. 3B). For example, the signal element can be a fluorescent molecule that is quenched by binding to the artificial receptor. For example, the signal element can be a molecule that fluoresces only when binding occurs. The floor can be modified with a plurality of floor modifiers. For example, the floor can be modified with both a signal element and a small group that alters the recognition properties of the floor.

In an embodiment, the candidate artificial receptor can include building blocks and unmodified amines of the floor. Such a candidate artificial receptor has an amine/ammonium floor. In an embodiment, the candidate artificial receptor can include building blocks and modified amines of the floor. For example, the floor amines can be modified by the simplest amide modification of the amines to form the acetamide (e.g., by reacting with acetic anhydride or acetyl chloride). Alternatively, the floor amines can be modified by reaction with succinic anhydride, benzoyl chloride, and the like.

A lawn or other coating of functional groups can be derivatized with a maximum density of building blocks by exposing the lawn to several equivalents of activated building blocks. Typically, 10 or more equivalents is sufficient for an adequate density of building blocks on the support to observe building-block-dependent binding of a ligand. An amine modified glass surface can be functionalized with building blocks, for example, by reaction with activated carboxyl derivatives to form an amide link to the lawn.

For example, a building block linker carboxyl group can be activated by reacting the building block with carbodiimide in the presence of sulfo N-hydroxysuccinimide in aqueous dimethylformamide. The activated building block can be reacted directly with an amine on a glass support (hereinafter amino glass). FIG. 3A illustrates that derivatization of only a portion of the amine groups on the support can be effective for producing candidate artificial receptors. Although not limiting to the present invention, it is believed that the amine load on the glass is in excess of that required for candidate artificial receptor preparation. Preparations of surfaces including combinations of building blocks can be accomplished by, for example, premixing of activated building blocks prior to addition to the amino tube or the sequential mixing of the coupling solutions in the tubes.

Figure 5:
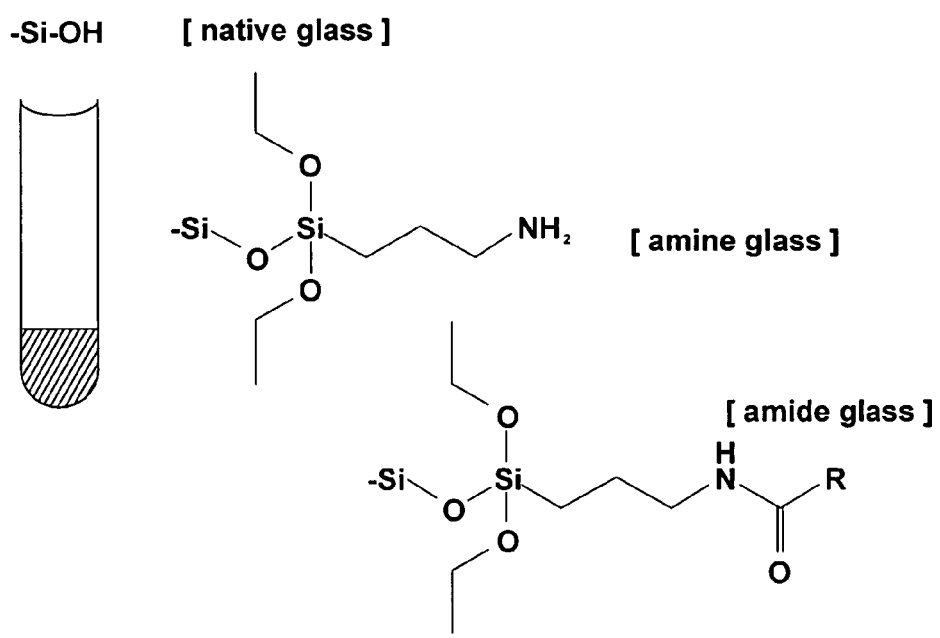
FIG. 5 schematically illustrates a glass support including pendant amine or amide structures.

A commercially available glass support can be prepared for coupling building blocks by adding a support matrix to the surface of the support. The support matrix provides functional groups for coupling to the building block. Suitable support matrices include silanating agents. For example a glass tube (e.g., a 12×75 mm borosilicate glass tube from VWR) can be coated to form a lawn of amines by reaction of the glass with a silanating agent such as 3-aminopropyltriethoxysilane. Building blocks including an activated ester can be bound to this coating by reaction of the building block activated ester with the amine glass to form the amide bound building block. Starting with a commercially available slide, an amino functionalized slide from Coming, building blocks including an activated ester can be spotted on and covalently bound to the slide in a micro array by this same reaction. Such derivatization is illustrated in FIG. 5.

Using The Artificial Receptors

Figure 6:
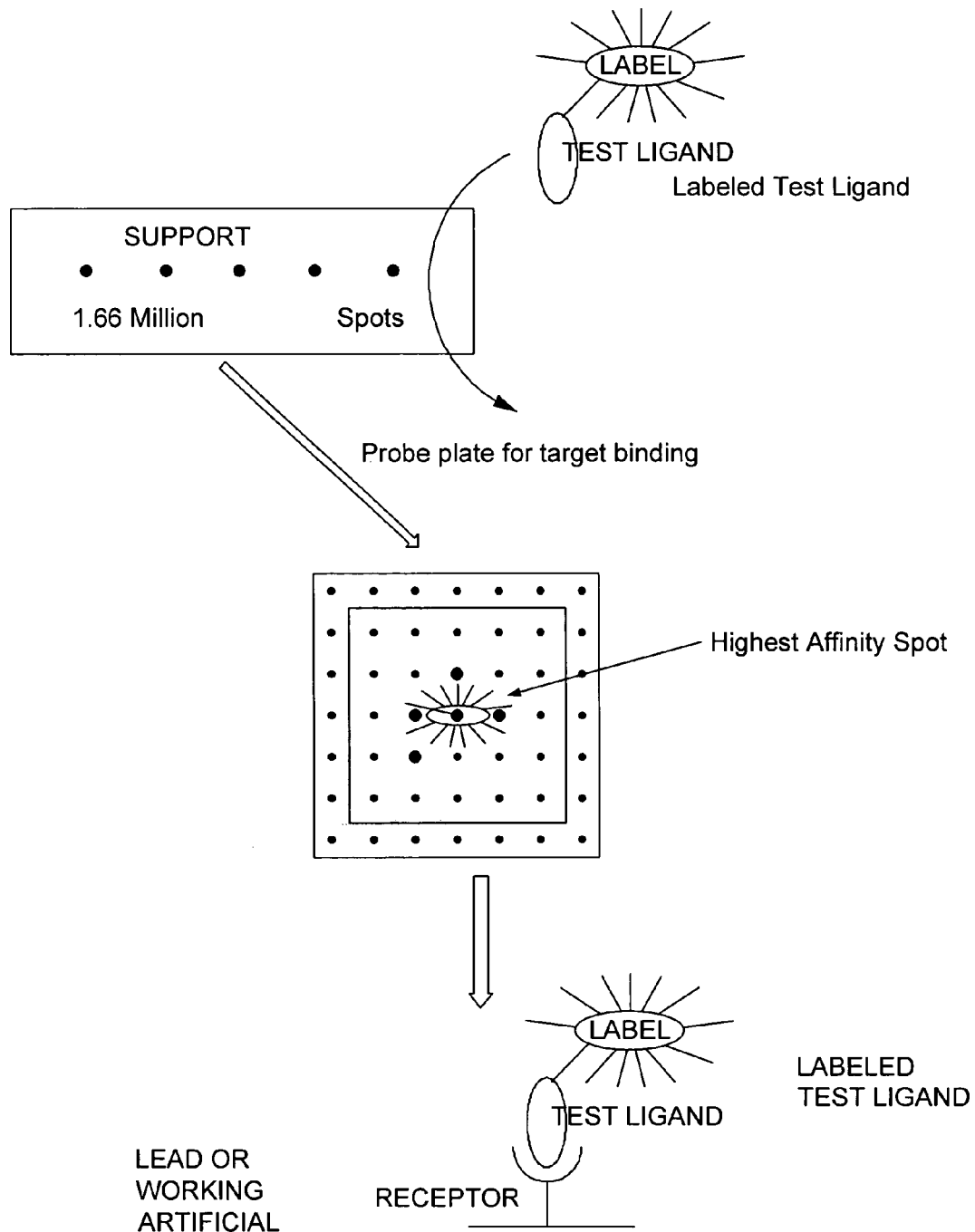
FIG. 6 schematically illustrates identification of a lead artificial receptor from among candidate artificial receptors.

The present invention includes a method of using artificial receptors. The present invention includes a method of screening candidate artificial receptors to find lead artificial receptors that bind a particular test ligand. Detecting test ligand bound to a candidate artificial receptor can be accomplished using known methods for detecting binding to arrays on a slide or to coated tubes or wells. Typically, the method employs test ligand labeled with a detectable label, such as a fluorophore or an enzyme that produces a detectable product. Alternatively, the method can employ an antibody (or other binding agent) specific for the test ligand and including a detectable label. One or more of the spots that are labeled by the test ligand or that are more or most intensely labeled with the test ligand are selected as lead artificial receptors. The degree of labeling can be evaluated by evaluating the signal strength from the label. Typically, the amount of signal is directly proportional to the amount of label and binding. The test ligand can be a pure compound, a mixture, or a "dirty" mixture containing a natural product or pollutant. Such dirty mixtures can be tissue homogenate, biological fluid, soil sample, water sample, or the like. FIG. 6 provides a schematic illustration of an embodiment of this process.

According to the present method, screening candidate artificial receptors against a test ligand can yield one or more lead artificial receptors. One or more lead artificial receptors can be a working artificial receptor. That is, the one or more lead artificial receptors can be useful for detecting the ligand of interest as is. The method can then employ the one or more artificial receptors as a working artificial receptor for monitoring or detecting the test ligand. Alternatively, the one or more lead artificial receptors can be employed in the method for developing a working artificial receptor. For example, the one or more lead artificial receptors can provide structural or other information useful for designing or screening for an improved lead artificial receptor or a working artificial receptor. Such designing or screening can include making and testing additional candidate artificial receptors including combinations of a subset of building blocks, a different set of building blocks, or a different number of building blocks.

In certain embodiments, the method of the present invention can employ a smaller number of spots formed by combinations of a subset of the total building blocks and/or smaller groups of the building blocks. For example, the present method can employ an array including the number of spots formed by combinations of 81 building blocks in groups of 2 and/or 3. Then a smaller number of building blocks indicated by test compound binding, for example 36 building blocks, can be tested in a microarray with spots including larger groups, for example 4, of the building blocks. Each set of microarrays can employ a different support matrix, lawn, or functionalized lawn. Such methods are schematically illustrated in FIG. 7.

Figure 7:
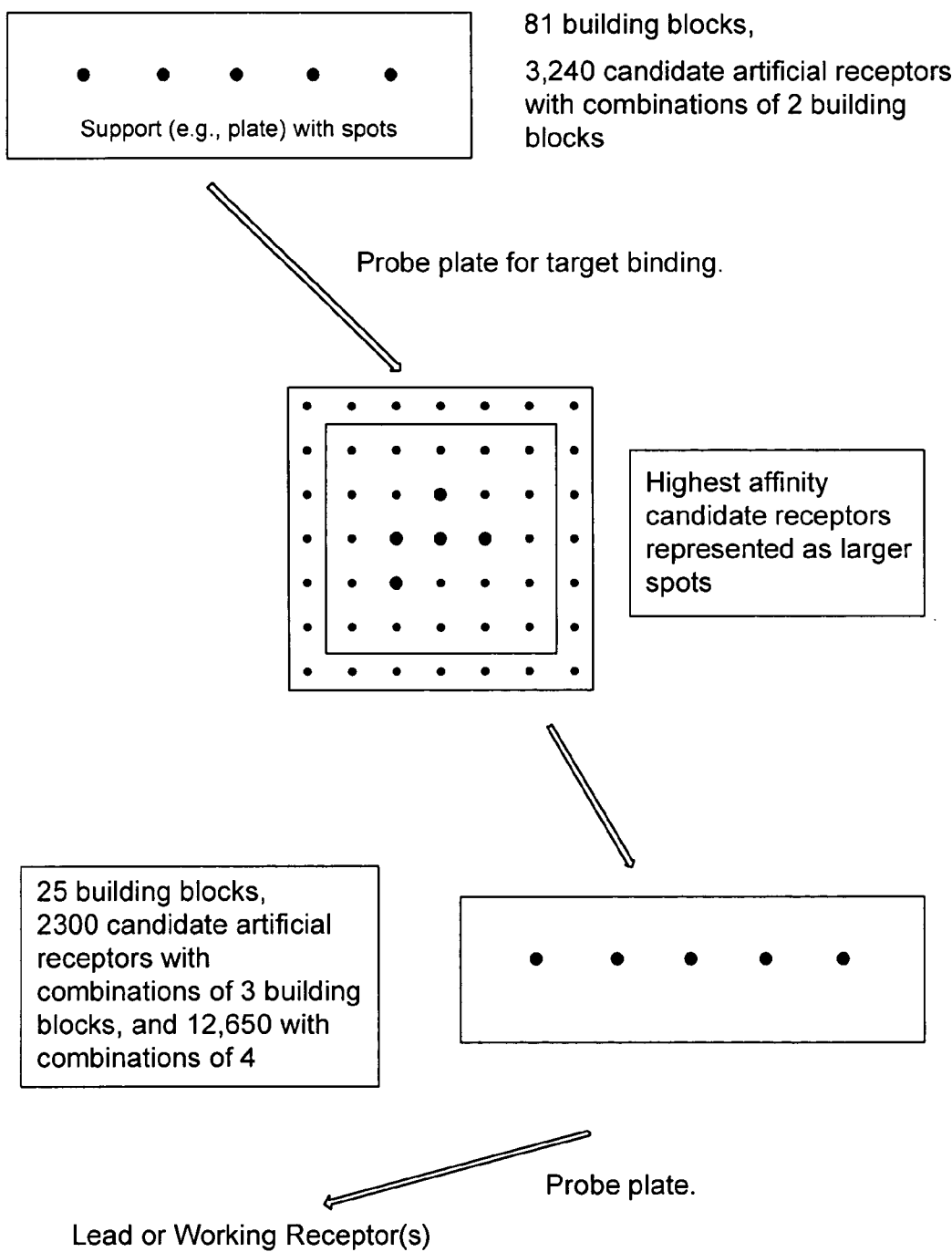
FIG. 7 schematically illustrates employing successive subsets of the available building blocks to develop a lead or working artificial receptor.

For example, FIG. 7 illustrates that a single slide with the 3,240 combinations of 2 building blocks that can be produced from a set of 81 building blocks can be used to define a subset of the building blocks. This subset of, e.g., 25, building blocks (which can be derived from a 5×5 matrix of the results employing combinations of 2 building blocks), can be used to produce an additional 2,300 combinations of 3 building blocks and/or 12,650 combinations of 4 building blocks. These combinations from the subset can be screened to define the optimum receptor configuration. The method can also include using combinations of building blocks in different ratios in spots.

On a macro scale, an artificial receptor presented spot or region including a plurality of building blocks has the plurality of building blocks distributed randomly throughout the spot or region. On a molecular scale, the distribution may not be random and even. For example, any selected group of only 2-10 building blocks may include a greater number of a particular building block or a particular arrangement of building blocks with respect to one another. A spot or region with a random distribution makes a useful artificial receptor according to the present invention. Particular assortments of building blocks found in a random distribution can also make useful artificial receptors.

Figure 8:
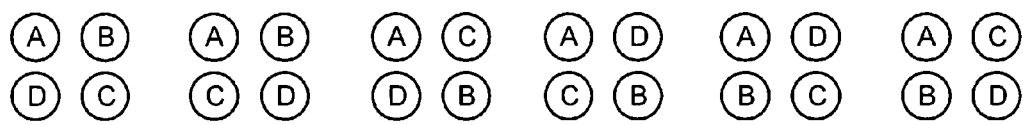
FIG. 8 schematically illustrates positional isomers of combinations of 4 building blocks (A, B, C, and D) at vertices of a quadrilateral, and such isomers on a scaffold. The representations of the positional isomers on a scaffold include building blocks A, B, C, and D and a sphere representing a ligand of interest.
Figure 8:
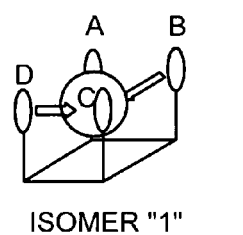
Figure 8:
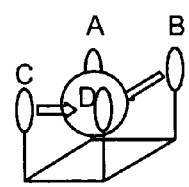
Figure 8:
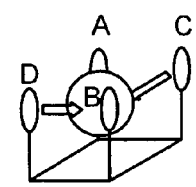

An artificial receptor can include a particular assortment of a combination of 2, 3, 4, or more building blocks. Such an assortment can be visualized as occupying positions on the surface of a support. A combination of 2, 3, 4, or more building blocks can have each of the different building blocks in distinct positions relative to one another. For example, building block 1 can be adjacent to any of building blocks 2, 3, or 4. This can be illustrated by considering the building blocks at the vertices of a polygon. For example, FIG. 8 illustrates positional isomers of 4 different building blocks at the vertices of a quadrilateral.

In an embodiment of the method, a candidate artificial receptor can be optimized to a preferred lead or working artificial receptor by making one or more of the positional isomers and determining its ability to bind the test ligand of interest. Advantageously, the positional isomers can be made on a scaffold (FIG. 8). Scaffold positional isomer artificial receptors can be made, for example, on a scaffold with multiple functional groups that can be protected and deprotected by orthogonal chemistries. The scaffold positional isomer lead artificial receptors can be evaluated by any of a variety of methods suitable for evaluating binding of ligands to scaffold receptors. For example, the scaffold lead artificial receptors can be chromatographed against immobilized test ligand.

In an embodiment, the method of using an artificial receptor includes contacting a first heterogeneous molecular array with a test ligand. The array can include a support and a plurality of spots of building blocks attached to the support. In the array, each spot of building blocks can include a plurality of building blocks with each building block being coupled to the support. The method includes detecting binding of a test ligand to one or more spots; and selecting one or more of the binding spots as the artificial receptor.

In this embodiment, the building blocks in the array can define a first set of building blocks, and the plurality of building blocks in each binding spot defines one or more selected binding combinations of building blocks. The first set of building blocks can include or be a subset of a larger set of building blocks. In an embodiment, the spots of building blocks can include 2, 3, or 4 building blocks. The first set can be immobilized using a first support matrix, a first lawn, or a first functionalized lawn.

In the method, the artificial receptor can include or be one or more lead artificial receptors. In the method, the artificial receptors can include or be one or more working artificial receptors.

This embodiment of the method can also include determining the combinations of building blocks in the one or more binding spots. These combinations can be used as the basis for developing one or more developed combinations of building blocks distinct from those in the one or more selected combinations of building blocks. This embodiment continues with contacting the test ligand with a second heterogeneous molecular array comprising a plurality of spots, each spot comprising a developed combination of building blocks; detecting binding of a test ligand to one or more spots of the second heterogeneous molecular array; and selecting one or more of the spots of the second heterogeneous molecular array as the artificial receptor. The second set can be immobilized using a second support matrix, a second lawn, or a second functionalized lawn different from those used with the first set.

In this embodiment, the building blocks in the second heterogeneous molecular array define a second set of building blocks. The first set of building blocks can include or be a subset of a larger set of building blocks and/or the second subset of building blocks can include or define a subset of the larger set of building blocks. Advantageously, the first subset is not equivalent to the second subset. In an embodiment, the spots of the second heterogeneous molecular array can include 3, 4, or 5 building blocks, and/or the spots of the second heterogeneous molecular array can include more building blocks than the binding spots.

The artificial receptor can include or be a lead artificial receptor. The artificial receptor can include or be one or more working artificial receptors. The method can also include varying the structure of the lead artificial receptor to increase binding speed or binding affinity of the test ligand.

In an embodiment, the method includes identifying the plurality of building blocks making up the artificial receptor. The identified plurality of building blocks can then be coupled to a scaffold molecule to make a scaffold artificial receptor. This scaffold artificial receptor can be evaluated for binding of the test ligand. In an embodiment, coupling the identified plurality of building blocks to the scaffold can include making a plurality of positional isomers of the building blocks on the scaffold. Evaluating the scaffold artificial receptor can then include comparing the plurality of the scaffold positional isomer artificial receptors. In this embodiment, one or more of the scaffold positional isomer artificial receptors can be selected as one or more lead or working artificial receptors.

In an embodiment, the method includes screening a test ligand against an array including one or more spots that function as controls for validating or evaluating binding to artificial receptors of the present invention. In an embodiment, the method includes screening a test ligand against one or more regions, tubes, or wells that function as controls for validating or evaluating binding to artificial receptors of the present invention. Such a control spot, region, tube, or well can include no building block, only a single building block, only functionalized lawn, or combinations thereof.

Embodiments of Artificial Receptors

A candidate artificial receptor, a lead artificial receptor, or a working artificial receptor includes combination of building blocks immobilized on, for example, a support. An individual artificial receptor can be a heterogeneous building block spot on a slide or a plurality of building blocks coated on a tube or well.

An array of candidate artificial receptors can be a commercial product sold to parties interested in using the candidate artificial receptors as implements in developing receptors for test ligands of interest. In an embodiment, a useful array of candidate artificial receptors includes a plurality of glass slides, the glass slides including spots of all combinations of members of a set of building blocks, each combination including a predetermined number of building blocks. In an embodiment, a useful group of candidate artificial receptors includes a plurality of tubes or wells, each with a coating of a plurality of immobilized building blocks.

One or more lead artificial receptors can be developed from a plurality of candidate artificial receptors. In an embodiment, a lead artificial receptor includes a combination of building blocks and binds detectable quantities of test ligand upon exposure to, for example, several picomoles of test ligand at a concentration of 1, 0.1, or 0.01 µg/ml, or at 1, 0.1, or 0.01 ng/ml test ligand; at a concentration of 0.01 µg/ml, or at 1, 0.1, or 0.01 ng/ml test ligand; or a concentration of 1, 0.1, or 0.01 ng/ml test ligand.

Artificial receptors, particularly candidate or lead artificial receptors, can be in the form of an array of artificial receptors. Such an array can include, for example, 1.66 million spots, each spot including one combination of 4 building blocks from a set of 81 building blocks. Each spot is a candidate artificial receptor and a combination of building blocks. The array can also be constructed to include lead artificial receptors. For example, the array of artificial receptors can include combinations of fewer building blocks and/or a subset of the building blocks.

In an embodiment, an array of candidate artificial receptors includes building blocks of general Formula 2 (shown hereinbelow), with $RE_1$ being B1, B2, B3, B4, B5, B6, B7, B8, or B9 (shown hereinbelow) and with $RE_2$ being A1, A2, A3, A4, A5, A6, A7, A8, or A9 (shown hereinbelow). Preferably the framework is tyrosine.

One or more working artificial receptors can be developed from one or more lead artificial receptors. In an embodiment, a working artificial receptor includes a combination of building blocks and binds categorizing or identifying quantities of test ligand upon exposure to, for example, several picomoles of test ligand at a concentration of 100, 10, 1, 0.1, 0.01, or 0.001 ng/ml test ligand; at a concentration of 10, 1, 0.1, 0.01, or 0.001 ng/ml test ligand; or a concentration of 1, 0.1, 0.01, or 0.001 ng/ml test ligand.

In an embodiment, the artificial receptor of the invention includes a plurality of building blocks coupled to a support. In an embodiment, the plurality of building blocks can include or be building blocks of Formula 2 (shown below). In an embodiment, the plurality of building blocks can include or be building blocks of formula TyrA2B2 and/or TyrA4B4 (shown below; the abbreviation for the building block including a linker, a tyrosine framework, and recognition elements AxBy is TyrAxBy). In an embodiment, the plurality of building blocks can include or be building blocks of formula TyrA4B2 and/or TyrA4B4 (shown below). In an embodiment, the plurality of building blocks can include or be building blocks of formula TyrA2B2, TyrA4B2, TyrA4B4, and/or TyrA6B6 (shown below).

In an embodiment, a candidate artificial receptor can include combinations of building blocks of formula TyrA2B2, TyrA4B4, or TyrA6B6. In an embodiment, a candidate artificial receptor can include combinations of building blocks of formula TyrA2B2, TyrA4B4, TyrA6B6, TyrA4B2, or TyrA4B6. In an embodiment, a candidate artificial receptor can include combinations of building blocks of formula TyrA2B2, TyrA2B4, TyrA4B2, TyrA4B4, TyrA4B6, TyrA6B4, TyrA6B6, TyrA6B8, TyrA8B6, or TyrA8B8.

Working Receptor Systems

In an embodiment, a working artificial receptor or working artificial receptor complex can be incorporated into a system or device for detecting a ligand of interest. Binding of a ligand of interest to a working artificial receptor or complex can produce a detectable signal, for example, through mechanisms and properties such as scattering, absorbing or emitting light, producing or quenching fluorescence or luminescence, producing or quenching an electrical signal, and the like. Spectroscopic detection methods include use of labels or enzymes to produce light for detection by optical sensors or optical sensor arrays. The light can be ultraviolet, visible, or infrared light, which can be produced and/or detected through fluorescence, fluorescence polarization, chemiluminescence, bioluminescence, or chemibioluminescence. Systems and methods for detecting electrical conduction, and changes in electrical conduction, include ellipsometry, surface plasmon resonance, capacitance, conductometry, surface acoustic wave, quartz crystal microbalance, love-wave, infrared evanescent wave, enzyme labels with electrochemical detection, nanowire field effect transistors, MOSFETS—metal oxide semiconductor field effect transistors, CHEMFETS—organic membrane metal oxide semiconductor field effect transistors, ICP—intrinsically conducting polymers, FRET—fluorescence resonance energy transfer.

Apparatus that can detect such binding to or signal from a working artificial receptor or complex includes UV, visible or Infrared spectrometer, fluorescence or luminescence spectrometer, surface plasmon resonance, surface acoustic wave or quartz crystal microbalance detectors, pH, voltammetry or amperometry meters, radioisotope detector, or the like.

In such an apparatus, a working artificial receptor or complex can be positioned on a light fiber to provide a detectable signal, such as an increase or decrease in transmitted light, reflected light, fluorescence, luminescence, or the like. The detectable signal can originate from, for example, a signaling moiety incorporated into the working artificial receptor or complex or a signaling moiety added to the working artificial receptor. The signal can also be intrinsic to the working artificial receptor or to the ligand of interest. The signal can come from, for example, the interaction of the ligand of interest with the working artificial receptor, the interaction of the ligand of interest with a signaling moiety which has been incorporated into the working artificial receptor, into the light fiber, onto the light fiber.

In an embodiment of the system, more than one working artificial receptor, arranged as regions or spots in an array, is on the surface of a support, such as a glass plate. The ligand or ligands of interest or a sample suspected of containing the ligand or ligands of interest (e.g., a sample containing a mixture of DNA segments or fragments, proteins or protein fragments, carbohydrates or carbohydrate fragments, or the like) is brought into contact with the working artificial receptors or array. Contact can be achieved by addition of a solution of the ligand or ligands of interest or a sample suspected of containing the ligand or ligands of interest. A detectable fluorescence signal can be produced by a signaling moiety incorporated into the working artificial receptor array or a signaling moiety which is added to the ligand or ligands of interest or the sample suspected of containing the ligand or ligands of interest. The fluorescent moieties produce a signal for each working artificial receptor in the array, which produces a pattern of signal response which is characteristic of the composition of the sample of interest.

In an embodiment of the system, more than one working artificial receptor, arranged as regions or spots in an array, is on a support, such as a glass or plastic surface. The surface can be incorporated onto the signaling surfaces of one or more surface plasmon resonance detectors. The ligands of interest or a sample suspected of containing the ligands of interest (e.g., a sample containing a mixture of DNA segments or fragments, proteins or protein fragments, carbohydrates or carbohydrate fragments, or the like) is brought into contact with the working artificial receptors or array. Contacting can be accomplished by addition of a solution of the ligands of interest or a sample suspected of containing the ligands of interest. Detectable electrical signals can be produced by binding of the ligands of interest to the working artificial receptors array on the surface of the surface plasmon resonance detectors. Such detectors produce a signal for each working artificial receptor in the array, which produces a pattern of signal response, which is characteristic of the composition of the sample of interest.

In an embodiment of the system, the working artificial receptor is on a support such as the inner surface of a test tube, microwell, capillary, microchannel, or the like. The ligand of interest or a sample suspected of containing the ligand of interest is brought into contact with the working artificial receptor or complex by addition of a solution containing the ligand of interest or a sample suspected of containing the ligand of interest. A detectable calorimetric, fluorometric, radiometric, or the like, signal is produced by a colorimetric, enzyme, fluorophore, radioisotope, metal ion, or the like, labeled compound or conjugate of the ligand of interest. This labeled moiety can be reacted with the working artificial receptor or complex in competition with the solution containing the ligand of interest or the sample suspected of containing the ligand of interest.

In an embodiment of the system, the working artificial receptor is on a support such as the surface of a surface acoustic wave or quartz crystal microbalance or surface plasmon resonance detector. The ligand of interest or a sample suspected of containing the ligand of interest can be brought into contact with the working artificial receptor or complex by exposure to a stream of air, to an aerosol, or to a solution containing the ligand of interest or a sample suspected of containing the ligand of interest. A detectable electrical signal can be produced by the interaction of the ligand of interest with the working artificial receptor or complex on the active surface of the surface acoustic wave or quartz crystal microbalance or surface plasmon resonance detector.

In an embodiment of the system, the more than one working artificial receptor, arranged as a series of discrete areas or spots or zones or the like, is on the surface of a light fiber. The ligand of interest or a sample suspected of containing the ligand of interest can be brought into contact with the working artificial receptor or complex by exposure to a stream of air, to an aerosol, or to a solution containing the ligand of interest or a sample suspected of containing the ligand of interest. A detectable calorimetric, fluorometric, or like signal can be produced by a label incorporated into the light fiber surface. The colorimetric or fluorogenic signal can be intrinsic to the ligand, or can be an inherent calorimetric or fluorogenic signal produced on binding of the ligand to the working artificial receptors.

An embodiment of the system, combines the artificial receptors with nanotechnology derived nanodevices to give the devices the ability to bind ("see"), bind and incorporate ("eat"), or modify ("use in manufacture") the target material. In an embodiment of the system, the working artificial receptor is incorporated into or on a nanodevice. The ligand of interest or a sample suspected of containing the ligand of interest can be brought into contact with the working artificial receptor nanodevice by addition of the nanodevice to an air or water or soil or biological fluid or cell or biological tissue or biological organism or the like. A detectable signal can be produced by a suitable sensor on the nanodevice and a desired action like a radio signal or chemical reaction or mechanical movement or the like is produced by the nanodevice in response to the ligand of interest.

The present artificial receptors can be part of products used in: analyzing a genome and/or proteome; pharmaceutical development; detectors for any of the test ligands; drug of abuse diagnostics or therapy; hazardous waste analysis or remediation; chemical warfare alert or intervention; disease diagnostics or therapy; cancer diagnostics or therapy; biowarfare alert or intervention; food chain contamination analysis or remediation; and the like.

More specifically, the present artificial receptors can be used in products for identification of sequence specific small molecule leads; protein isolation and identification; identification of protein to protein interactions; detecting contaminants in food or food products; clinical analysis of food contaminants; clinical analysis of prostate specific antigen; clinical and field or clinical analysis of cocaine; clinical and field or clinical analysis of other drugs of abuse; other clinical analysis systems, home test systems, or field analysis systems; monitors or alert systems for bioterrorism or chemical warfare agents; and the like.

Test Ligands

The test ligand can be any ligand for which binding to an array or surface can be detected. Test ligands include prostate specific antigen, other cancer markers, insulin, warfarin, other anti-coagulants, cocaine, other drugs-of-abuse, markers for *E. coli*, markers for *Salmonella sp.*, markers for other food-borne toxins, food-borne toxins, markers for Smallpox virus, markers for anthrax, markers for other possible bioterrorism agents, pharmaceuticals and medicines, pollutants and chemicals in hazardous waste, chemical warfare agents, markers of disease, pharmaceuticals, pollutants, biologically important cations (e.g., potassium or calcium ion), peptides, carbohydrates, enzymes, bacteria, viruses, and the like.

Building Blocks

The present invention relates to building blocks for making or forming candidate artificial receptors. Building blocks are designed, made, and selected to provide a variety of structural characteristics among a small number of compounds. A building block can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A building block can be bulky or it can be small.

A building block can be visualized as including several components, such as one or more frameworks, one or more linkers, and/or one or more recognition elements. The framework can be covalently coupled to each of the other building block components. The linker can be covalently coupled to the framework and to a support. The recognition element can be covalently coupled to the framework. In an embodiment, a building block includes a framework, a linker, and a recognition element. In an embodiment, a building block includes a framework, a linker, and two recognition elements. A building block including a framework, a linker, and one or more recognition elements can be schematically represented as:

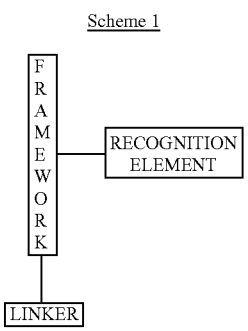

Scheme 1

Framework

The framework can be selected for functional groups that provide for coupling to the recognition moiety and for coupling to or being the linking moiety. The framework can interact with the ligand as part of the artificial receptor. Typically, the framework includes multiple reaction sites with orthogonal and reliable functional groups and with controlled stereochemistry. Suitable functional groups with orthogonal and reliable chemistries include, for example, carboxyl, amine, hydroxyl, phenol, carbonyl, and thiol groups, which can be individually protected, deprotected, and derivatized. Typically, the framework has two, three, or four functional groups with orthogonal and reliable chemistries.

A framework including three sites for orthogonal and reliable chemistries can be schematically represented as:

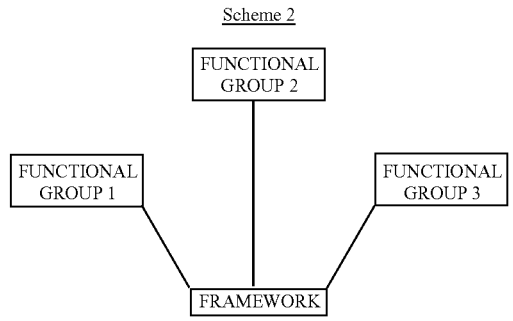

Scheme 2

The three functional groups can be independently selected, for example, from carboxyl, amine, hydroxyl, phenol, carbonyl, or thiol group. The framework can include alkyl, substituted alkyl, cycloalkyl, heterocyclic, substituted heterocyclic, aryl alkyl, aryl, heteroaryl, heteroaryl alkyl, and like moieties.

A general structure for a framework with three functional groups can be represented by Formula 1a:

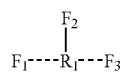

A general structure for a framework with four functional groups can be represented by Formula 1b:

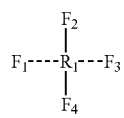

In these general structures: $R_1$ can be a 1-12, preferably 1-6, preferably 1-4 carbon alkyl, substituted alkyl, cycloalkyl, heterocyclic, substituted heterocyclic, aryl alkyl, aryl, heteroaryl, heteroaryl alkyl, or like group; and $F_1$, $F_2$, $F_3$, or $F_4$ can independently be a carboxyl, amine, hydroxyl, phenol, carbonyl, or thiol group. $F_1$, $F_2$, $F_3$, or $F_4$ can independently be a 1-12, preferably 1-6, preferably 1-4 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group. $F_3$ and/or $F_4$ can be absent.

A variety of compounds fit the schemes and formulas describing the framework including amino acids, and naturally occurring or synthetic compounds including, for example, oxygen and sulfur functional groups. The compounds can be racemic or optically active. For example, the compounds can be natural or synthetic amino acids, α-hydroxy acids, thioic acids, and the like.

Suitable molecules for use as a framework include a natural or synthetic amino acid, particularly an amino acid with a functional group (e.g., third functional group) on its side chain. Amino acids include carboxyl and amine functional groups. The side chain functional group can include, for natural amino acids, an amine (e.g., alkyl amine, heteroaryl amine), hydroxyl, phenol, carboxyl, thiol, thioether, or amidino group. Natural amino acids suitable for use as frameworks include, for example, serine, threonine, tyrosine, aspartic acid, glutamic acid, asparagine, glutamine, cysteine, lysine, arginine, histidine. Synthetic amino acids can include the naturally occurring side chain functional groups or synthetic side chain functional groups which modify or extend the natural amino acids with alkyl, substituted alkyl, cycloalkyl, heterocyclic, substituted heterocyclic, aryl alkyl, aryl, heteroaryl, heteroaryl alkyl, and like moieties as framework and with carboxyl, amine, hydroxyl, phenol, carbonyl, or thiol functional groups. Preferred synthetic amino acids include β-amino acids and homo or β analogs of natural amino acids.

Figure 9:
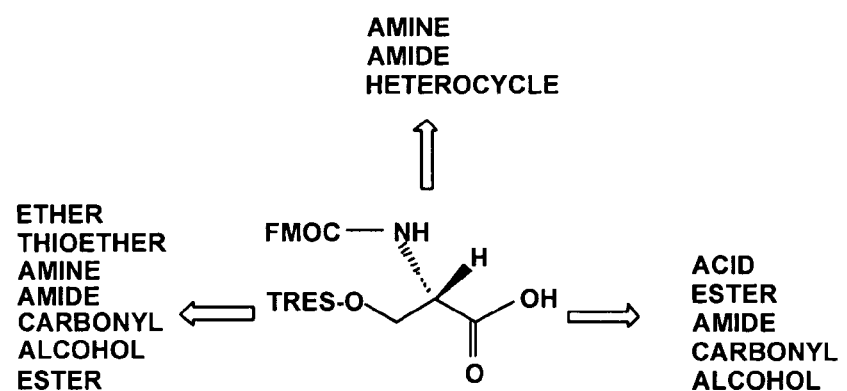
FIG. 9 schematically illustrates serine as a framework for a building block and reactions for derivatizing the building block to add recognition elements.

Preferred framework amino acids include serine, threonine, or tyrosine, preferably serine or tyrosine, preferably tyrosine. FIG. 9 illustrates serine as a framework for a building block and reactions for forming building blocks from serine, tyrosine, and other amino acids. Threonine and tyrosine typically exhibit reactivity similar to serine. Advantageously, serine, threonine, and tyrosine include: 1) multiple, orthogonal, well characterized reaction sites, 2) known methods and reactions for application as a combinatorial framework, 3) diversity of sub-structures and domains which can be incorporated through the carboxyl, α-amine, and hydroxyl functionalities, 4) compact distribution of the multiple reaction sites around a tetrahedral carbon framework, and 5) ready commercial availability of reagents for forming linkers and/or recognition elements.

Figure 10:
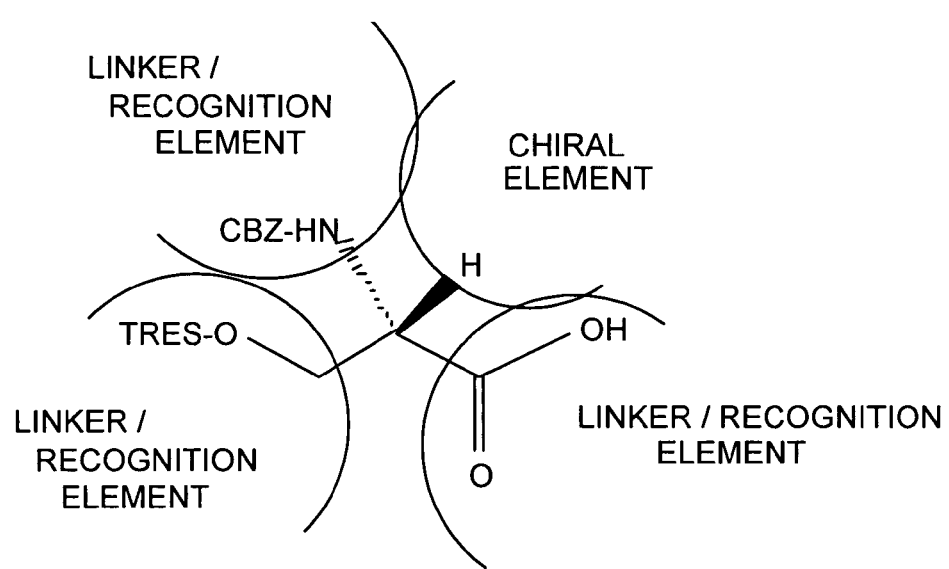
FIG. 10 schematically illustrates configurations in which recognition element(s), linker(s), and a chiral element can be coupled to a serine framework.

FIG. 10 illustrates configurations in which recognition element, linker, and a chiral element can be coupled to a tyrosine framework. Threonine and serine can form analogous configurations. The chiral element is a substituent that renders the carbon atom to which it is attached a chiral center. When one or more different recognition elements are also substituents on or coupled to the chiral center, the recognition elements can adopt two or more enantiomeric configurations. Such enantiomers can be advantageous for providing diversity among building blocks.

Although not limiting to the present invention, a framework amino acid, such as serine, threonine, or tyrosine, with a linker and two recognition elements can be visualized with one of the recognition elements in a pendant orientation and the other in an equatorial orientation, relative to the extended carbon chain of the framework.

Although not limiting to the present invention, the present building block framework can include: 1) diversity of framework reaction sites to maximize incorporation of potential receptor functionality, 2) reliable reaction and protection chemistries, 3) compact structure, 4) incorporation of diverse sub-structures, 5) a suitable platform for linker element incorporation, and/or 6) development of non-equivalent diversity domains to minimize redundancy in the receptor building blocks while maximizing the number of functional groups and sub-structures incorporated into a small library. Typically, the framework includes multiple reaction sites with compact format. Compact format is advantageous for providing a building block that fits at a suitable density on a support.

All of the naturally occurring and many synthetic amino acids are commercially available. Further, forms of these amino acids derivatized or protected to be suitable for reactions for coupling to recognition element(s) and/or linkers can be purchased or made by known methods (see, e.g., Green, T W; Wuts, P G M (1999), *Protective Groups in Organic Synthesis Third Edition*, Wiley-Interscience, New York, 779 pp.; Bodanszky, M.; Bodanszky, A. (1994), The Practice of Peptide Synthesis Second Edition, Springer-Verlag, New York, 217 pp.).

Preferred reaction schemes for preparing amino acids for reactions for forming building blocks according to the present invention include those provided in the present Examples.

Recognition Element

The recognition element can be selected to provide one or more structural characteristics to the building block. The framework can interact with the ligand as part of the artificial receptor. For example, the recognition element can provide one or more structural characteristics such as positive charge, negative charge, acid, base, electron acceptor, electron donor, hydrogen bond donor, hydrogen bond acceptor, free electron pair, π electrons, charge polarization, hydrophilicity, hydrophobicity, and the like. A recognition element can be a small group or it can be bulky.

In an embodiment the recognition element can be a 1-12, preferably 1-6, preferably 1-4 carbon alkyl, substituted alkyl, cycloalkyl, heterocyclic, substituted heterocyclic, aryl alkyl, aryl, heteroaryl, heteroaryl alkyl, or like group. The recognition element can be substituted with a group that includes or imparts positive charge, negative charge, acid, base, electron acceptor, electron donor, hydrogen bond donor, hydrogen bond acceptor, free electron pair, π electrons, charge polarization, hydrophilicity, hydrophobicity, and the like.

Recognition elements with a positive charge (e.g., at neutral pH in aqueous compositions) include amines, quaternary ammonium moieties, ferrocene, and the like. Suitable amines include alkyl amines, alkyl diamines, heteroalkyl amines, aryl amines, heteroaryl amines, aryl alkyl amines, pyridines, heterocyclic amines (saturated or unsaturated, the nitrogen in the ring or not), amidines, hydrazines, and the like. Alkyl amines generally have 1 to 12 carbons, preferably 1-8, rings can have 3-12 carbons, preferably 3-8. Suitable alkyl amines include that of formula B9. Suitable heterocyclic or alkyl heterocyclic amines include that of formula A9. Suitable pyridines include those of formulas A5 and B5. Any of the amines can be employed as a quaternary ammonium compound. Additional suitable quaternary ammonium moieties include trimethyl alkyl quaternary ammonium moieties, dimethyl ethyl alkyl quaternary ammonium moieties, dimethyl alkyl quaternary ammonium moieties, aryl alkyl quaternary ammonium moieties, pyridinium quaternary ammonium moieties, and the like.

Recognition elements with a negative charge (e.g., at neutral pH in aqueous compositions) include carboxylates, phenols substituted with strongly electron withdrawing groups (e.g., substituted tetrachlorophenols), phosphates, phosphonates, phosphinates, sulphates, sulphonates, thiocarboxylates, and hydroxamic acids. Suitable carboxylates include alkyl carboxylates, aryl carboxylates, and aryl alkyl carboxylates. Suitable phosphates include phosphate mono-, di-, and tri- esters, and phosphate mono-, di-, and tri-amides. Suitable phosphonates include phosphonate mono- and di- esters, and phosphonate mono- and di- amides (e.g., phosphonamides). Suitable phosphinates include phosphinate esters and amides.

Recognition elements with a negative charge and a positive charge (at neutral pH in aqueous compositions) include sulfoxides, betaines, and amine oxides.

Acidic recognition elements can include carboxylates, phosphates, sulphates, and phenols,. Suitable acidic carboxylates include thiocarboxylates. Suitable acidic phosphates include the phosphates listed hereinabove.

Basic recognition elements include amines. Suitable basic amines include alkyl amines, aryl amines, aryl alkyl amines, pyridines, heterocyclic amines (saturated or unsaturated, the nitrogen in the ring or not), amidines, and any additional amines listed hereinabove. Suitable alkyl amines include that of formula B9. Suitable heterocyclic or alkyl heterocyclic amines include that of formula A9. Suitable pyridines include those of formulas A5 and B5.

Recognition elements including a hydrogen bond donor include amines, amides, carboxyls, protonated phosphates, protonated phosphonates, protonated phosphinates, protonated sulphates, protonated sulphinates, alcohols, and thiols. Suitable amines include alkyl amines, aryl amines, aryl alkyl amines, pyridines, heterocyclic amines (saturated or unsaturated, the nitrogen in the ring or not), amidines, ureas, and any other amines listed hereinabove. Suitable alkyl amines include that of formula B9. Suitable heterocyclic or alkyl heterocyclic amines include that of formula A9. Suitable pyridines include those of formulas A5 and B5. Suitable protonated carboxylates, protonated phosphates include those listed hereinabove. Suitable amides include those of formulas A8 and B8. Suitable alcohols include primary alcohols, secondary alcohols, tertiary alcohols, and aromatic alcohols (e.g., phenols). Suitable alcohols include those of formulas A7 (a primary alcohol) and B7 (a secondary alcohol).

Recognition elements including a hydrogen bond acceptor or one or more free electron pairs include amines, amides, carboxylates, carboxyl groups, phosphates, phosphonates, phosphinates, sulphates, sulphonates, alcohols, ethers, thiols, and thioethers. Suitable amines include alkyl amines, aryl amines, aryl alkyl amines, pyridines, heterocyclic amines (saturated or unsaturated, the nitrogen in the ring or not), amidines, ureas, and amines as listed hereinabove. Suitable alkyl amines include that of formula B9. Suitable heterocyclic or alkyl heterocyclic amines include that of formula A9. Suitable pyridines include those of formulas A5 and B5. Suitable carboxylates include those listed hereinabove. Suitable amides include those of formulas A8 and B8. Suitable phosphates, phosphonates and phosphinates include those listed hereinabove. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include alkyl ethers, aryl alkyl ethers. Suitable alkyl ethers include that of formula A6. Suitable aryl alkyl ethers include that of formula A4. Suitable thioethers include that of formula B6.

Recognition elements including uncharged polar or hydrophilic groups include amides, alcohols, ethers, thiols, thioethers, esters, thio esters, boranes, borates, and metal complexes. Suitable amides include those of formulas A8 and B8. Suitable alcohols include primary alcohols, secondary alcohols, tertiary alcohols, aromatic alcohols, and those listed hereinabove. Suitable alcohols include those of formulas A7 (a primary alcohol) and B7 (a secondary alcohol). Suitable ethers include those listed hereinabove. Suitable ethers include that of formula A6. Suitable aryl alkyl ethers include that of formula A4.

Recognition elements including uncharged hydrophobic groups include alkyl (substituted and unsubstituted), alkene (conjugated and unconjugated), alkyne (conjugated and unconjugated), aromatic. Suitable alkyl groups include lower alkyl, substituted alkyl, cycloalkyl, aryl alkyl, and heteroaryl alkyl. Suitable lower alkyl groups include those of formulas A1, A3, and B1. Suitable aryl alkyl groups include those of formulas A3, A4, B3, and B4. Suitable alkyl cycloalkyl groups include that of formula B2. Suitable alkene groups include lower alkene and aryl alkene. Suitable aryl alkene groups include that of formula B4. Suitable aromatic groups include unsubstituted aryl, heteroaryl, substituted aryl, aryl alkyl, heteroaryl alkyl, alkyl substituted aryl, and polyaromatic hydrocarbons. Suitable aryl alkyl groups include those of formulas A3 and B4. Suitable alkyl heteroaryl groups include those of formulas A5 and B5.

Spacer recognition elements include hydrogen, methyl, ethyl, and the like. Bulky recognition elements include 7 or more carbon or hetero atoms.

Formulas A1-A9 and B1-B9 are:

 A1

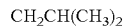 A2

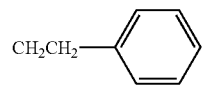 A3

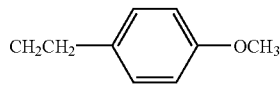 A4

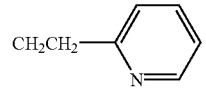 A5

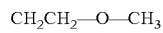 A6

 A7

 A8

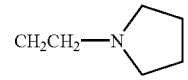 A9

 B1

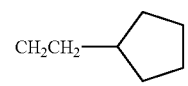 B2

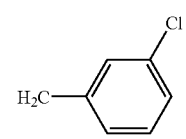 B3

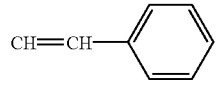 B4

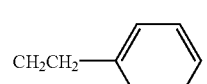 B5

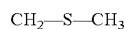 B6

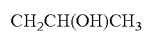 B7

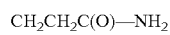 B8

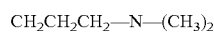 B9

These A and B recognition elements can be called derivatives of, according to a standard reference: A1, ethylamine;

A2, isobutylamine; A3, phenethylamine; A4, 4-methoxyphenethylamine; A5, 2-(2-aminoethyl)pyridine; A6, 2-methoxyethylamine; A7, ethanolamine; A8, N-acetylethylenediamine; A9, 1-(2-aminoethyl)pyrrolidine; B 1, acetic acid, B2, cyclopentylpropionic acid; B3, 3-chlorophenylacetic acid; B4, cinnamic acid; B5, 3-pyridinepropionic acid; B6, (methylthio)acetic acid; B7, 3-hydroxybutyric acid; B8, succinamic acid; and B9, 4-(dimethylamino)butyric acid.

In an embodiment, the recognition elements include one or more of the structures represented by formulas A1, A2, A3, A4, A5, A6, A7, A8, and/or A9 (the A recognition elements) and/or B1, B2, B3, B4, B5, B6, B7, B8, and/or B9 (the B recognition elements). In an embodiment, each building block includes an A recognition element and a B recognition element. In an embodiment, a group of 81 such building blocks includes each of the 81 unique combinations of an A recognition element and a B recognition element. In an embodiment, the A recognition elements are linked to a framework at a pendant position. In an embodiment, the B recognition elements are linked to a framework at an equatorial position. In an embodiment, the A recognition elements are linked to a framework at a pendant position and the B recognition elements are linked to the framework at an equatorial position.

Although not limiting to the present invention, it is believed that the A and B recognition elements represent the assortment of functional groups and geometric configurations employed by polypeptide receptors. Although not limiting to the present invention, it is believed that the A recognition elements represent six advantageous functional groups or configurations and that the addition of functional groups to several of the aryl groups increases the range of possible binding interactions. Although not limiting to the present invention, it is believed that the B recognition elements represent six advantageous functional groups, but in different configurations than employed for the A recognition elements. Although not limiting to the present invention, it is further believed that this increases the range of binding interactions and further extends the range of functional groups and configurations that is explored by molecular configurations of the building blocks.

Reagents that form many of the recognition elements are commercially available. For example, reagents for forming recognition elements A1, A2, A3, A4, A5, A6, A7, A8, A9 B1, B2, B3, B4, B5, B6, B7, B8, and B9 are commercially available.

Linkers

The linker is selected to provide a suitable covalent attachment of the building block to a support. The framework can interact with the ligand as part of the artificial receptor. The linker can also provide bulk, distance from the support, hydrophobicity, hydrophilicity, and like structural characteristics to the building block. Preferably, the linker forms a covalent bond with a functional group on the framework. Preferably, before attachment to the support the linker also includes a functional group that can be activated to react with or that will react with a functional group on the support. Preferably, once attached to the support, the linker forms a covalent bond with the support and with the framework.

The linker preferably forms or can be visualized as forming a covalent bond with an alcohol, phenol, thiol, amine, carbonyl, or like group on the framework. The linker can include a carboxyl, alcohol, phenol, thiol, amine, carbonyl, maleimide, or like group that can react with or be activated to react with the support. Between the bond to the framework and the group formed by the attachment to the support, the linker can include an alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

The linker can include a good leaving group bonded to, for example, an alkyl or aryl group. The leaving group being "good" enough to be displaced by the alcohol, phenol, thiol, amine, carbonyl, or like group on the framework. Such a linker can include a moiety represented by the formula: R—X, in which X is a leaving group such as halogen (e.g., —Cl, —Br or —I),tosylate, mesylate, triflate, and R is alkyl, substituted alkyl, cycloalkyl, heterocyclic, substituted heterocyclic, aryl alkyl, aryl, heteroaryl, heteroaryl alkyl, ethoxy or propoxy oligomer, a glycoside, or like moiety.

Preferred linker groups include those of formula: $(CH_2)_n COOH$, with n=1-16, preferably n=2-8, preferably n=2-6, preferably n=3. Reagents that form suitable linkers are commercially available and include any of a variety of reagents with orthogonal functionality.

Embodiments of Building Blocks

In an embodiment, building blocks can be represented by Formula 2:

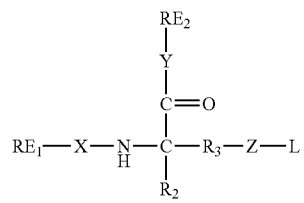

in which: $RE_1$ is recognition element 1, $RE_2$ is recognition element 2, and L is a linker. X is absent, C=O, $CH_2$, NR, $NR_2$, NH, NHCONH, SCONH, CH=N, or $OCH_2NH$. Preferably X is absent or C=O. Y is absent, NH, O, $CH_2$, or NRCO. Preferably Y is NH or O. Preferably Y is NH. Z is CH2, O, NH, S, CO, NR, $NR_2$, NHCONH, SCONH, CH=N, or $OCH_2NH$. Preferably Z is O. $R_2$ is H, $CH_3$, or another group that confers chirality on the building block and has size similar to or smaller than a methyl group. $R_3$ is $CH_2$; $CH_2$-phenyl; $CHCH_3$; $(CH_2)_n$ with n=2-3; or cyclic alkyl with 3-8 carbons, preferably 5-6 carbons, phenyl, naphthyl. Preferably $R_3$ is $CH_2$ or $CH_2$-phenyl.

$RE_1$ is B1, B2, B3, B4, B5, B6, B7, B8, B9, A1, A2, A3, A4, A5, A6, A7, A8, or A9. Preferably $RE_1$ is B1, B2, B3, B4, B5, B6, B7, B8, or B9. $RE_2$ is A1, A2, A3, A4, A5, A6, A7, A8, A9, B1, B2, B3, B4, B5, B6, B7, B8, or B9. Preferably $RE_2$ is A1, A2, A3, A4, A5, A6, A7, A8, or A9. In an embodiment, $RE_1$, can be B2, B4, or B6 and $RE_2$ can be A2, A4, or A6. In an embodiment, $RE_1$, can be B1, B3, B6, or B8 and $RE_2$ can be A2, A4, A5, or A9. In an embodiment, $RE_1$, can be B2, B4, B6, or B8 and $RE_2$ can be A2, A4, A6, or A8. In an embodiment, $RE_1$, can be B1, B2, B4, B6, or B8 and $RE_2$ can be A1, A2, A4, A6, or A8.

L is $(CH_2)_n COOH$, with n=1-16, preferably n=2-8, preferably n=4-6, preferably n=3.

Embodiments of such building blocks include:

4-{4-[(acetylamino-ethylcarbamoyl-methyl)-amino]-phenoxy}-butyric acid;

4-(4-{[(3 -cyclopentyl-propionylamino)-ethylcarbamoyl-methyl]-amino }-phenoxy)-butyric acid;

4-[4-({[2-(3-chloro-phenyl)-acetylamino]-ethylcarbamoyl-methyl}-amino)-phenoxy]-butyric acid;

4-(4-{[ethylcarbamoyl-(3-phenyl-acryloylamino)-methyl]-amino}-phenoxy)-butyric acid;
4-(4-{[ethylcarbamoyl-(3-pyridin-3-yl-propionylamino)-methyl]-amino}-phenoxy)-butyric acid;
4-(4-{[ethylcarbamoyl-(2-methylsulfanyl-acetylamino)-methyl]-amino}-phenoxy)-butyric acid;
4-(4-{[ethylcarbamoyl-(3-hydroxy-butyrylamino)-methyl]-amino}-phenoxy)-butyric acid;
4-(4-{[(3-carbamoyl-propionylamino)-ethylcarbamoyl-methyl]-amino}-phenoxy)-butyric acid;
4-(4-{[(4-dimethylamino-butyrylamino)-ethylcarbamoyl-methyl]-amino}-phenoxy)-butyric acid;
4-{4-[(acetylamino-isobutylcarbamoyl-methyl)-amino]-phenoxy}-butyric acid;
4-(4-{[(3-cyclopentyl-propionylamino)-isobutylcarbamoyl-methyl]-amino}-phenoxy)-butyric acid;
4-[4-({ [2-(3-chloro-phenyl)-acetylamino]-isobutylcarbamoyl-methyl}-amino)-phenoxy]-butyric acid;
4-(4-{[isobutylcarbamoyl-(3-phenyl-acryloylamino)-methyl]-amino}-phenoxy)-butyric acid;
4-(4-{[isobutylcarbamoyl-(3-pyridin-3-yl-propionylamino)-methyl]-amino}-phenoxy)-butyric acid;
4-(4-{[isobutylcarbamoyl-(2-methylsulfanyl-acetylamino)-methyl]-amino}-phenoxy)-butyric acid;
4-(4-{[(3-hydroxy-butyrylamino)-isobutylcarbamoyl-methyl]-amino}-phenoxy)-butyric acid;
4-(3-{[(3-carbamoyl-propionylamino)-isobutylcarbamoyl-methyl]-amino}-phenoxy)-butyric acid;
4-(4-{[(4-dimethylamino-butyrylamino)-isobutylcarbamoyl-methyl]-amino}-phenoxy)-butyric acid;
4-{4-[(acetylamino-phenethylcarbamoyl-methyl)-amino]-phenoxy}-butyric acid;
4-(4-{[(3-cyclopentyl-propionylamino)-phenethylcarbamoyl-methyl]-amino}-phenoxy)-butyric acid;
4-[4-({[2-(3-chloro-phenyl)-acetylamino]-phenethylcarbamoyl-methyl}-amino)-phenoxy]-butyric acid;
4-(4-{[phenethylcarbamoyl-(3-phenyl-acryloylamino)-methyl]-amino}-phenoxy)-butyric acid;
4-(4-{[phenethylcarbamoyl-(3-pyridin-3-yl-propionylamino)-methyl]-amino}-phenoxy)-butyric acid;
4-(4-{[(2-methylsulfanyl-acetylamino)-phenethylcarbamoyl-methyl]-amino}-phenoxy)-butyric acid;
4-(4-{[(3-hydroxy-butyrylamino)-phenethylcarbamoyl-methyl]-amino}-phenoxy)-butyric acid;
4-(4-{[(3-carbamoyl-propionylamino)-phenethylcarbamoyl-methyl]-amino}-phenoxy)-butyric acid;
4-(4-{[(4-dimethylamino-butyrylamino)-phenethylcarbamoyl-methyl]-amino}-phenoxy)-butyric acid;
4-[4-({acetylamino-[2-(4-methoxy-phenyl)-ethylcarbamoyl]-methyl}-amino)-phenoxy]-butyric acid;
4-[4-({(3-cyclopentyl-propionylamino)-[2-(4-methoxy-phenyl)-ethylcarbamoyl]-methyl}-amino)-phenoxy]-butyric acid;
4-[4-({[2-(3-chloro-phenyl)-acetylamino]-[2-(4-methoxy-phenyl)-ethylcarbamoyl]-methyl}-amino)-phenoxy]-butyric acid;
4-(4-{[[2-(4-methoxy-phenyl)-ethylcarbamoyl]-(3-phenyl-acryloylamino)-methyl]-amino}-phenoxy)-butyric acid;
4-(4-{[[2-(4-methoxy-phenyl)-ethylcarbamoyl]-(3-pyridin-3-yl-propionylamino)-methyl]-amino}-phenoxy)-butyric acid;
4-(4-{[[2-(4-methoxy-phenyl)-ethylcarbamoyl]-(2-methylsulfanyl-acetylamino)-methyl]-amino}-phenoxy)-butyric acid;
4-[4-({(3-hydroxy-butyrylamino)-[2-(4-methoxy-phenyl)-ethylcarbamoyl]-methyl}-amino)-phenoxy]-butyric acid;
4-[4-({(3-carbamoyl-propionylamino)-[2-(4-methoxy-phenyl)-ethylcarbamoyl]-methyl}-amino)-phenoxy]-butyric acid;
4-[4-({(4-dimethylamino-butyrylamino)-[2-(4-methoxy-phenyl)-ethylcarbamoyl]-methyl}-amino)-phenoxy]-butyric acid;
4-(4-{[acetylamino-(2-pyridin-2-yl-ethylcarbamoyl)-methyl]-amino}-phenoxy)-butyric acid;
4-(4-{[(3-cyclopentyl-propionylamino)-(2-pyridin-2-yl-ethylcarbamoyl)-methyl]-amino}-phenoxy)-butyric acid;
4-(4-{[[2-(3-chloro-phenyl)-acetylamino]-(2-pyridin-2-yl-ethylcarbamoyl)-methyl]-amino}-phenoxy)-butyric acid;
4-(4-{[(3-phenyl-acryloylamino)-(2-pyridin-2-yl-ethylcarbamoyl)-methyl]-amino}-phenoxy)-butyric acid;
4-(4-{[(2-pyridin-2-yl-ethylcarbamoyl)-(3-pyridin-3-yl-propionylamino)-methyl]-amino}-phenoxy)-butyric acid;
4-(4-{[(2-methylsulfanyl-acetylamino)-(2-pyridin-2-yl-ethylcarbamoyl)-methyl]-amino}-phenoxy)-butyric acid;
4-(4-{[(3-hydroxy-butyrylamino)-(2-pyridin-2-yl-ethylcarbamoyl)-methyl]-amino}-phenoxy)-butyric acid;
4-(4-{[(3-carbamoyl-propionylamino)-(2-pyridin-2-yl-ethylcarbamoyl)-methyl]-amino}-phenoxy)-butyric acid;
4-(4-{[(4-dimethylamino-butyrylamino)-(2-pyridin-2-yl-ethylcarbamoyl)-methyl]--amino}-phenoxy)-butyric acid;
4-(4-{[acetylamino-(2-methoxy-ethylcarbamoyl)-methyl]-amino}-phenoxy)-butyric acid;
4-(4-{[(3-cyclopentyl-propionylamino)-(2-methoxy-ethylcarbamoyl)-methyl]-amino}-phenoxy)-butyric acid;
4-(4-{[[2-(3-chloro-phenyl)-acetylamino]-(2-methoxy-ethylcarbamoyl)-methyl]-amino}-phenoxy)-butyric acid;
4-(4-{[(2-methoxy-ethylcarbamoyl)-(3-phenyl-acryloylamino)-methyl]-amino}-phenoxy)-butyric acid;
4-(4-{[(2-methoxy-ethylcarbamoyl)-(3-pyridin-3-yl-propionylamino)-methyl]-amino}-phenoxy)-butyric acid;
4-(4-{[(2-methoxy-ethylcarbamoyl)-(2-methylsulfanyl-acetylamino)-methyl]-amino}-phenoxy)-butyric acid;
4-(4-{[(3-hydroxy-butyrylamino)-(2-methoxy-ethylcarbamoyl)-methyl]-amino}-phenoxy)-butyric acid;
4-(3-{[(3-carbamoyl-propionylamino)-(2-methoxy-ethylcarbamoyl)-methyl]-amino}-phenoxy)-butyric acid;
4-(4-{[(4-dimethylamino-butyrylamino)-(2-methoxy-ethylcarbamoyl)-methyl]--amino}-phenoxy)-butyric acid;
4-(4-{[acetylamino-(2-hydroxy-ethylcarbamoyl)-methyl]-amino}-phenoxy)-butyric acid;
4-(4-{[(3-cyclopentyl-propionylamino)-(2-hydroxy-ethylcarbamoyl)-methyl]-amino}-phenoxy)-butyric acid;
4-(4-{[[2-(3-chloro-phenyl)-acetylamino]-(2-hydroxy-ethylcarbamoyl)-methyl]-amino}-phenoxy)-butyric acid;
4-(4-{[(2-hydroxy-ethylcarbamoyl)-(3-phenyl-acryloylamino)-methyl]-amino}-phenoxy)-butyric acid;
4-(4-{[(2-hydroxy-ethylcarbamoyl)-(3-pyridin-3-yl-propionylamino)-methyl]-amino}-phenoxy)-butyric acid;
4-(4-{[(2-hydroxy-ethylcarbamoyl)-(2-methylsulfanyl-acetylamino)-methyl]-amino}-phenoxy)-butyric acid;
4-(4-{[(3-hydroxy-butyrylamino)-(2-hydroxy-ethylcarbamoyl)-methyl]-amino}-phenoxy)-butyric acid;
4-(3-{[(3-carbamoyl-propionylamino)-(2-hydroxy-ethylcarbamoyl)-methyl]-amino}-phenoxy)-butyric acid;
4-(4-{[(4-dimethylamino-butyrylamino)-(2-hydroxy-ethylcarbamoyl)-methyl]--amino}-phenoxy)-butyric acid;
4-(4-{[acetylamino-(2-acetylamino-ethylcarbamoyl)-methyl]-amino}-phenoxy)-butyric acid;
4-(4-{[(2-acetylamino-ethylcarbamoyl)-(3-cyclopentyl-propionylamino)-methyl]-amino}-phenoxy)-butyric acid;
4-[4-({(2-acetylamino-ethylcarbamoyl)-[2-(3-chloro-phenyl)-acetylamino]-methyl}-amino)-phenoxy]-butyric acid;

4-(4-{[(2-acetylamino-ethylcarbamoyl)-(3-phenyl-acryloylamino)-methyl]-amino}-phenoxy)-butyric acid;
4-(4-{[(2-acetylamino-ethylcarbamoyl)-(3-pyridin-3-yl-propionylamino)-methyl]-amino}-phenoxy)-butyric acid;
4-(4-{[(2-acetylamino-ethylcarbamoyl)-(2-methylsulfanyl-acetylamino)-methyl]-amino}-phenoxy)-butyric acid;
4-(4-{[(2-acetylamino-ethylcarbamoyl)-(3-hydroxy-butyrylamino)-methyl]-amino}-phenoxy)-butyric acid;
4-(3-{[(2-acetylamino-ethylcarbamoyl)-(3-carbamoyl-propionylamino)-methyl]-amino}-phenoxy)-butyric acid;
4-(4-{[(2-acetylamino-ethylcarbamoyl)-(4-dimethylamino-butyrylamino)-methyl]-amino}-phenoxy)-butyric acid;
4-(4-{[acetylamino-(2-pyrrolidin-1-yl-ethylcarbamoyl)-methyl]-amino}-phenoxy)-butyric acid;
4-(4-{[(3-cyclopentyl-propionylamino)-(2-pyrrolidin-1-yl-ethylcarbamoyl)-methyl]-amino}-phenoxy)-butyric acid;
4-(4-{[[2-(3-chloro-phenyl)-acetylamino]-(2-pyrrolidin-1-yl-ethylcarbamoyl)-methyl]-amino}-phenoxy)-butyric acid;
4-(4-{[(3-phenyl-acryloylamino)-(2-pyrrolidin-1-yl-ethylcarbamoyl)-methyl]-amino}-phenoxy)-butyric acid;
4-(4-{[(3-pyridin-3-yl-propionylamino)-(2-pyrrolidin-1-yl-ethylcarbamoyl)-methyl]-amino}-phenoxy)-butyric acid;
4-(4-{[(2-methylsulfanyl-acetylamino)-(2-pyrrolidin-1-yl-ethylcarbamoyl)-methyl]-amino}-phenoxy)-butyric acid;
4-(4-{[(3-hydroxy-butyrylamino)-(2-pyrrolidin-1-yl-ethylcarbamoyl)-methyl]-amino}-phenoxy)-butyric acid;
4-(3-{[(3-carbamoyl-propionylamino)-(2-pyrrolidin-1-yl-ethylcarbamoyl)-methyl]-amino}-phenoxy)-butyric acid;
4-(4-{[(4-dimethylamino-butyrylamino)-(2-pyrrolidin-1-yl-ethylcarbamoyl)-methyl]-amino}-phenoxy)-butyric acid;

salts thereof, esters thereof, protected or blocked derivatives thereof, immobilized derivatives thereof, derivatives thereof, or mixtures thereof. The nomenclature in this paragraph is according to the program CS CHEMDRAW ULTRA®.

Building blocks of Formula 2 and including an A recognition element, a B recognition element, a linker, and a framework of a naturally occurring α-amino acid can be visualized as having the B recognition element in an equatorial configuration and the A recognition element in a pendant configuration. An embodiment of such a configuration is schematically illustrated in Scheme 3:

Scheme 3

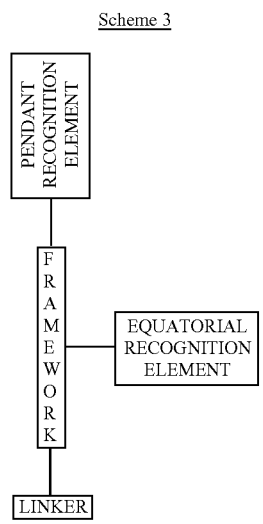

Building blocks including an A and/or a B recognition element, a linker, and an amino acid framework can be made by methods illustrated in general Scheme 4.

Scheme 4

TYROSINE FRAMEWORK

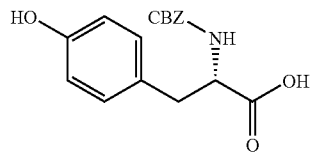

STEP #1
R—NH$_2$

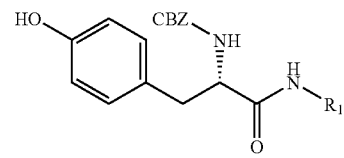

STEP #2
linker-CH$_2$X

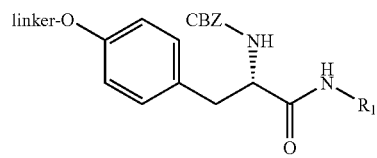

STEP #3
TFA

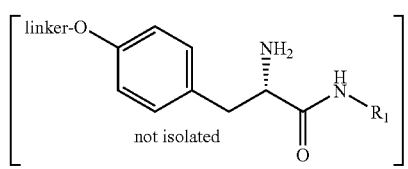

not isolated

STEP #4
R$_2$—COCl
STEP #5
hydrolysis

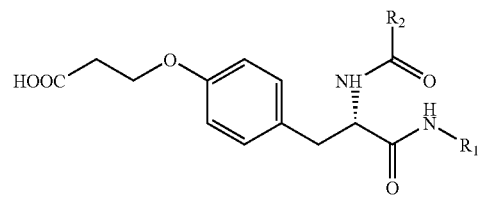

Figure 14:
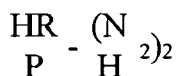
FIG. 14 schematically illustrates embodiments of HRP (Formula H1), HRP derivatives (Formulas H2 and H3), and conjugates of test ligand and HRP (Formulas H4, H5, and H6) useful in the present methods. Formula H4 represents a conjugate of HRP with a chloroaromatic compound designated 34K. Formula H5 represents a conjugate of HRP with an ethylene thiourea designated ETU. ETU includes both aryl and heterocyclic moieties. Formula H5 represents a conjugate of HRP with a polycyclic chlorodioxin derivative designated TCDD.
Figure 14:
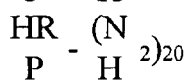
Figure 14:
Figure 14:
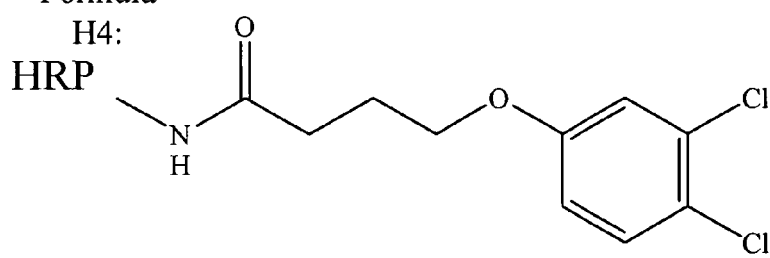
Figure 14:
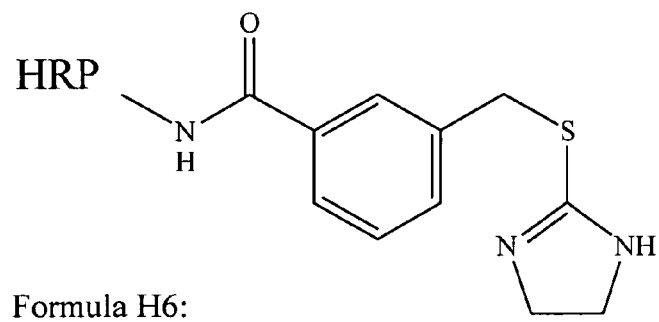
Figure 14:
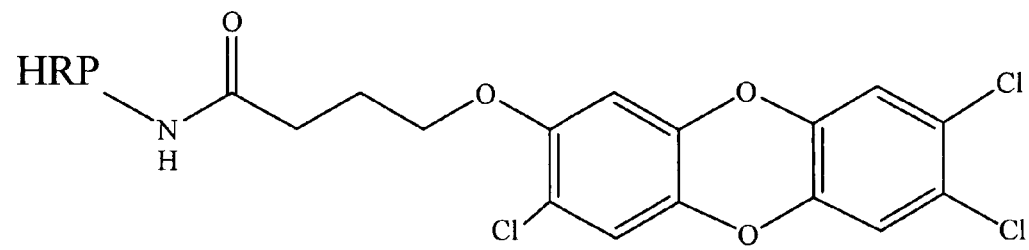

R = Receptor Functional Groups (Figure 14)

31

-continued

SERINE FRAMEWORK

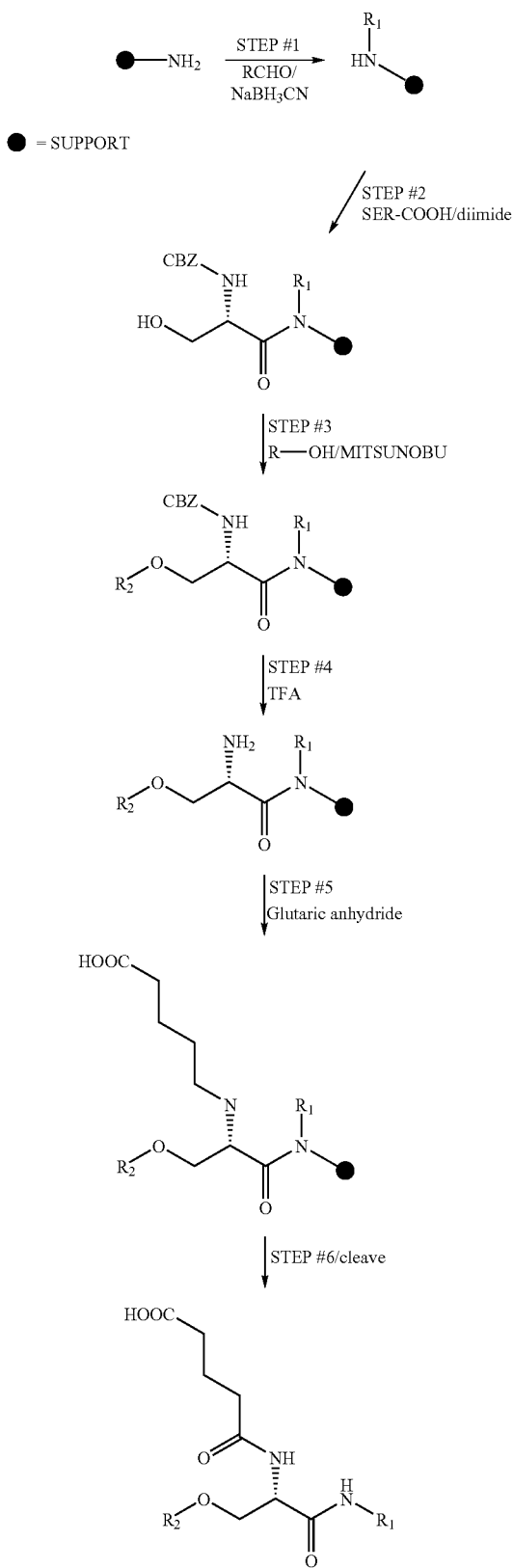

32

More on Building Blocks

Building blocks can be asymmetric. Employing asymmetry, various combinations of, for example, linker and recognition elements can produce building blocks that can be visualized to occupy 3D space in different ways. As a consequence, these different building blocks can perform binding related but otherwise distinct functions.

In an embodiment, building blocks including two recognition elements, a linker, and a framework can be visualized as having both recognition elements in spreading pendant configurations. An embodiment of such a configuration is schematically illustrated in Scheme 5:

Scheme 5

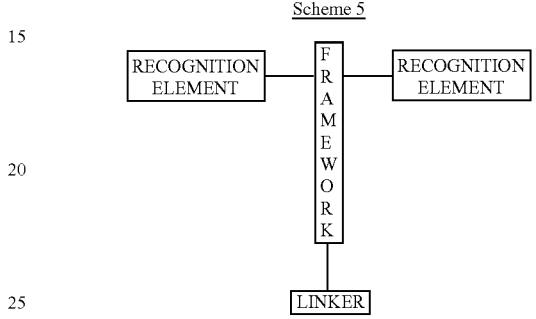

Such a configuration has a molecular footprint with substantial area in two dimensions. Such a larger footprint can be suitable, for example, for binding larger ligands that prefer or require interactions with a receptor over a larger area or that prefer or require interactions with a larger number of functional groups on the recognition element. Such larger ligands can include proteins, carbohydrates, cells, and microorganisms (e.g., bacteria and viruses).

In an embodiment, a building block can have only a single recognition element in a pendant configuration and a pendant linker distal on the framework. Such building blocks can be compact. Such a building block can interact with large molecules that include a binding region, such as a protein (e.g., enzyme or receptor) or other macromolecule. For example, such a building block can be employed to probe cavities, such as binding sites, on proteins.

Sets of Building Blocks

The present invention also relates to sets of building blocks. The sets of building blocks can include isolated building blocks, building blocks with an activated linker for coupling to a support, and/or building blocks coupled to a support. Sets of building blocks include a plurality of building blocks. The plurality of building blocks can be a component of a coating, of a spot or spots (e.g., forming candidate artificial receptor(s)), or of a kit. The plurality of building blocks can include a sufficient number of building blocks and recognition elements for exploring candidate artificial receptors or for defining receptors for a ligand. That is, the set of building blocks can include a majority (preferably at least 6) of the structural characteristics selected from positive charge, negative charge, acid, base, electron acceptor, electron donor, hydrogen bond donor, hydrogen bond acceptor, free electron pair, π electrons, charge polarization, hydrophilicity, hydrophobicity.

For a set of building blocks, the recognition elements are preferably selected to provide a variety of structural characteristics to the individual members of the set. A single building block can include recognition elements with more than one of the structural characteristics. A set of building blocks can include recognition elements with each of the structural characteristics. For example, a set of building blocks can include one or more building blocks including a positively charged recognition element, one or more building blocks including a negatively charged recognition element, one or more building blocks including an acidic recognition element, one or more building blocks including a basic recognition element, one or more building blocks including an electron donating recognition element, one or more building blocks including an electron accepting recognition element, one or more building blocks including a hydrogen bond donor recognition element, one or more building blocks including a hydrogen bond acceptor recognition element, one or more building blocks including a polar recognition element, one or more building blocks including a recognition element with free electron pair(s), one or more building blocks including a recognition element with π electrons, one or more building blocks including a hydrophilic recognition element, one or more building blocks including a hydrophobic recognition element, one or more building blocks including a small recognition element, and/or one or more building blocks including a bulky recognition element.

In an embodiment, the number and variety of recognition elements is selected to provide a set of building blocks with a manageable number of members. A manageable number of building blocks provides, typically, fewer than 10 million combinations, preferably about 2 million combinations, with each combination including, preferably, 3, 4, 5, or 6 building blocks. In an embodiment, the recognition elements provide a set of building blocks that incorporate the functional groups and configurations found in the components of natural receptors, preferably with the smallest number of building blocks.

The nine A and nine B recognition elements can be incorporated into a set of 81 (9×9) building blocks, each with one A and one B recognition element. Such building blocks can, for example, be prepared using combinatorial syntheses on a framework, such as a serine or tyrosine framework. In groups of 4, this set of 81 building blocks provides 1.66 million combinations of building blocks (Table 1), each of which can be a heterogeneous combination in a microarray on a support, substrate, or scaffold. Although not limiting to the present invention, it is believed that these groups of 4 are sufficient to incorporate the functional groups and configurations found in natural receptors and to provide sufficient candidate artificial receptors to yield one or more artificial receptors for a specified ligand.

Table 1—Calculation of the Number of Candidate Artificial Receptor Combinations

Discrete combinations calculated using the following formula for N compounds taken in groups of n (CRC Standard Math Tables and Formulas Handbook, 30th ed.):

| Number of Combinations = N!/(N-n)! n! For N = 81 | |
|---|---|
| GROUP | COMBINATIONS |
| n = 1 | 81 |
| n = 2 | 3,240 |
| n = 3 | 85,320 |
| n = 4 | 1,663,740 |

A set of building blocks can include building blocks of general Formula 2, with $RE_1$ being B1, B2, B3, B4, B5, B6, B7, B8, or B9 and with $RE_2$ being A1, A2, A3, A4, A5, A6, A7, A8, or A9. In an embodiment of the set, $RE_1$, can be B2, B4, or B6 and $RE_2$ can be A2, A4, or A6. In an embodiment of the set, $RE_1$, can be B1, B3, B6, or B8 and $RE_2$ can be A2, A4, A5, or A9. In an embodiment of the set, $RE_1$, can be B2, B4, B6, or B8 and $RE_2$ can be A2, A4, A6, or A8. In an embodiment of the set, $RE_1$, can be B1, B2, B4, B6, or B8 and $RE_2$ can be A1, A2, A4, A6, or A8. In an embodiment of the set, $RE_1$, can be B1, B2, B3, B4, B5, B6, B7, B8, or B9 and $RE_2$ can be A1, A2, A3, A4, A5, A6, A7, A8, or A9.

In an embodiment, a set of building blocks includes alkyl, aryl, and polar recognition elements, plus recognition elements that are combinations of these structural characteristics. A set of building blocks including those of general Formula 2, with $RE_1$ being B1, B2, B3, B4, B5, B6, B7, B8, or B9 and with $RE_2$ being A1, A2, A3, A4, A5, A6, A7, A8, or A9 is a set of building blocks with includes alkyl, aryl, and polar recognition elements. Table 2 illustrates an embodiment of 81 building blocks of general Formula 2 with recognition elements that span alkyl, aryl, and polar recognition elements.

TABLE 2

Embodiment of 81 Building Blocks of General Formula 2 with Recognition Elements that Span Alkyl, Aryl, and Polar Recognition Elements.

| | | | | | $RE_1$, EQUATORIAL | | | | | |
|---|---|---|---|---|---|---|---|---|---|---|
| | RE1 RE2 | B1 | B2 | B3 | B4 | B5 | B6 | B7 | B8 | B9 |
| $RE_2$ PENDANT | A1 | A1-B1 | A1-B2 | A1-B3 | A1-B4 | A1-B5 | A1-B6 | A1-B7 | A1-B8 | A1-B9 |
| | A2 | A2-B1 | A2-B2 | A2-B3 | A2-B4 | A2-B5 | A2-B6 | A2-B7 | A2-B8 | A2-B9 |
| | A3 | A3-B1 | A3-B2 | A3-B3 | A3-B4 | A3-B5 | A3-B6 | A3-B7 | A3-B8 | A3-B9 |
| | A4 | A4-B1 | A4-B2 | A4-B3 | A4-B4 | A4-B5 | A4-B6 | A4-B7 | A4-B8 | A4-B9 |
| | A5 | A5-B1 | A5-B2 | A5-B3 | A5-B4 | A5-B5 | A5-B6 | A5-B7 | A5-B8 | A5-B9 |
| | A6 | A6-B1 | A6-B2 | A6-B3 | A6-B4 | A6-B5 | A6-B6 | A6-B7 | A6-B8 | A6-B9 |
| | A7 | A7-B1 | A7-B2 | A7-B3 | A7-B4 | A7-B5 | A7-B6 | A7-B7 | A7-B8 | A7-B9 |
| | A8 | A8-B1 | A8-B2 | A8-B3 | A8-B4 | A8-B5 | A8-B6 | A8-B7 | A8-B8 | A8-B9 |
| | A9 | A9-B1 | A9-B2 | A9-B3 | A9-B4 | A9-B5 | A9-B6 | A9-B7 | A9-B8 | A9-B9 |

Embodiments of Sets of Building Blocks

The present invention includes sets of building blocks. Sets of building blocks can include 2 or more building blocks coupled to a support or scaffold. Such a support or scaffold can be referred to as including heterogeneous building blocks. As used herein, the term "support" refers to a solid support that is, typically, macroscopic. As used herein, the term scaffold refers to a molecular scale structure to which a plurality of building blocks can covalently bind. The two or more building blocks can be coupled to the support or scaffold in a molecular configuration with different building blocks in proximity to one another. Such a molecular configuration of a plurality of different building blocks provides a candidate artificial receptor.

Building Blocks on Supports

The present invention includes immobilized sets and combinations of building blocks. In an embodiment, the present invention includes a solid support having on its surface a plurality of building blocks.

For example, the support can be a glass tube or well coated with a plurality of building blocks. In an embodiment, the surface of the glass tube or well (e.g., a 96 well plate) coated with a coating to which the plurality of building blocks are covalently bound. Such a coating can be referred to as including heterogeneous building blocks. The surface or coating can include a density of building blocks sufficient to provide interactions of more than one building block with a ligand. The building blocks can be in proximity to one another. Evidence of proximity of different building blocks is provided by altered (e.g., tighter or looser) binding of a ligand to a surface with a plurality of building blocks compared to a surface with only one of the building blocks.

A set of building blocks can be employed in combinations of 2, 3, 4, or more building blocks on an individual tube or well. For this embodiment, with each combination using a bulky tube or well, a manageable set of building blocks preferably provides fewer than several hundred or several thousand combinations of building blocks. For example, in this context, a set of 3, 4, 5, or 6 building blocks provides a manageable number of combinations of 2, 3, or 4 building blocks.

In an embodiment, immobilized combinations of building blocks can include a plurality of tubes each tube having immobilized on its surface a heterogeneous combination of building blocks. The building blocks can be immobilized on the surface of the tube through amide links between each building block and a support matrix. The immobilized building blocks can include combinations of 2, 3, or 4 building blocks. For convenience in limiting the number of tubes handled, in this embodiment a set includes up to 5-7 building blocks, preferably 5 or fewer, preferably 3, 4, or 5. For tubes, suitable building blocks have general Formula 2, with $RE_1$, being B1, B2, B3, B4, B5, B6, B7, B8, or B9 and with $RE_2$ being A1, A2, A3, A4, A5, A6, A7, A8, or A9. In an embodiment for tubes, $RE_1$ can be B1, B3, B6, or B8 and $RE_2$ can be A2, A4, A5, or A9. In an embodiment for tubes, $RE_1$ can be B2, B4, or B6 and $RE_2$ can be A2, A4, or A6. In an embodiment for tubes, $RE_1$, can be B2, B4, B6, or B8 and $RE_2$ can be A2, A4, A6, or A8. In an embodiment for tubes, $RE_1$, can be B1, B2, B4, B6, or B8 and $RE_2$ can be A1, A2, A4, A6, or A8. A plurality of tubes each coated with a combination of building blocks can be configured as an array of tubes.

In an embodiment, the present invention includes a solid support having on its surface a plurality of regions or spots, each region or spot including a plurality of building blocks. For example, the support can be a glass slide spotted with a plurality of spots, each spot including a plurality of building blocks. Such a spot or region can be referred to as including heterogeneous building blocks. Each region or spot can include a density of building blocks sufficient to provide interactions of more than one building block with a ligand. Although each region or spot is typically separated from the others, in the region or spot, the building blocks can be in proximity to one another. Evidence of proximity of different building blocks in a region or spot is provided by altered (e.g., tighter or looser) binding of a ligand to a surface with a plurality of building blocks compared to a region or spot with only one of the building blocks. A plurality of regions or spots of building blocks is referred to herein as an array of regions or spots.

A set of building blocks can be employed in combinations of 2, 3, 4, or more building blocks in each region or spot. In such an embodiment, up to 100,000 spots can fit on a glass slide. Therefore, a manageable set of building blocks can provide several million combinations of building blocks. For example, in this context, a set of 81 building blocks provides a manageable number of (1.66 million) combinations of 4 building blocks. Although not limiting to the present invention, it is believed that these 1.66 million combinations are sufficient to incorporate the functional groups and configurations found in natural receptors and to provide sufficient candidate artificial receptors to yield one or more artificial receptors for a specified ligand.

In an embodiment, immobilized combinations of building blocks can include one or more glass slides, each slide having on its surface a plurality of spots, each spot including an immobilized heterogeneous combination of building blocks. The building blocks can be immobilized on the surface of the slide through amide links between each building block and a support matrix. The immobilized building blocks can include, for example, combinations of 2, 3, 4, 5, or 6 building blocks.

For convenience in limiting the number of slides handled, in this embodiment a set includes up to 200 building blocks, preferably 50-100, preferably about 80 (e.g., 81) building blocks. For slides, suitable building blocks have general Formula 2, with $RE_1$, being B1, B2, B3, B4, B5, B6, B7, B8, or B9 and with $RE_2$ being A1, A2, A3, A4, A5, A6, A7, A8, or A9. This embodiment can include a group of slides with 1.7 million heterogeneous spots, each spot including 4 building blocks.

In an embodiment, the one or more slides can include heterogeneous spots of building blocks made from combinations of a subset of the total building blocks and/or smaller groups of the building blocks in each spot. That is, each spot includes only, for example, 2 or 3 building blocks, rather than 4 or 5. For example, the one or more slides can include the number of spots formed by combinations of a full set of building blocks (e.g. 81 of a set of 81) in groups of 2 and/or 3. For example, the one or more slides can include the number of spots formed by combinations of a subset of the building blocks (e.g., 25 of the set of 81) in groups of 4 or 5. For example, the one or more slides can include the number of spots formed by combinations of a subset of the building blocks (e.g., 25 of the set of 81) in groups of 2 or 3. Should a candidate artificial receptor of interest be identified from the subset and/or smaller groups, then additional subsets and groups can be made or selected incorporating the building blocks in the candidates of interest or structurally similar building blocks.

For example, FIG. 7 illustrates that a single slide with the 3,240 n=2 derived combinations can be used to define a more limited set from the 81 building blocks. This defined set of e.g. 25 (defined from a 5×5 matrix of the n=2 results) can be used to produce an additional 2,300 n=3 derived and 12,650 n=4 derived combinations which can be probed to define the optimum receptor configuration. Further optimization can be pursued using ratios of the best building blocks which deviate from 1:1 followed by specific synthesis of the identified receptor(s).

Building blocks can be coupled to supports using known methods for activating compounds of the types employed as building blocks and for coupling them to supports. For example, building blocks including activated esters can be coupled to supports including amine functional groups. A carboxyl group on a building block can be derivatized to form the activated ester. By way of further example, building blocks including amine functional groups can be coupled to supports including carboxyl groups. Pairs of functional groups that can be employed on building blocks and supports include amine and carboxyl (or activated carboxyl), thiol and maleimide, and the like.

Individual or combinations of building blocks can be coupled to the supports in spots using conventional micro spotting techniques (e.g., piezoelectric, pin, and electromagnetic printers). Such spotting yields a microarray of spots of heterogeneous combinations of building blocks, each of which can be a candidate artificial receptor. As described herein above, each spot in a microarray includes a statistically significant number of each building block.

The set of building blocks can be on any of the variety of known supports employed in combinatorial or synthetic chemistry (e.g., a microscope slide, a bead, a resin, a gel, or the like). Suitable supports include functionalized glass, such as a functionalized slide or tube, glass microscope slide, glass plate, glass coverslip, glass beads, microporous glass beads, silica gel supports, and the like. As described hereinabove, a glass support can include a support matrix of silanating agent with functional groups suitable for coupling to a building block. For use in sets of building blocks, the support matrix functional groups can be pendant from the support in groups of one (e.g., as a lawn of amines or another functional group) or in groups of, for example, 2, 3, 4, 5, 6, or 7. The groups of a plurality of functional groups pendant from the support can be visualized as scaffold molecules pendant from the support.

The surface of the support can be visualized as including a floor and the building blocks (FIGS. 3A, 3B, and 4). Thus, the floor can be considered a feature of the candidate artificial receptor. In an embodiment, the candidate artificial receptor can include building blocks and unmodified amines of the floor. Such a candidate artificial receptor has an amine/ammonium floor. In an embodiment, the candidate artificial receptor can include building blocks and modified amines of the floor (e.g., the acetamide).

Sets on Scaffolds

In an embodiment, the present invention includes a scaffold molecule having coupled to it a plurality of building blocks. For example, the scaffold can be a polyamine, for example, a cyclic molecule with a plurality of primary amine groups around the ring. Such a scaffold can include a plurality of building blocks coupled to the amines. Such a scaffold can be referred to as including heterogeneous building blocks. The scaffold can provide a density of building blocks sufficient to provide interactions of more than one building block with a ligand. The building blocks can be in proximity to one another. Evidence of proximity of different building blocks on a scaffold is provided by altered (e.g., tighter or looser) binding of a ligand to a scaffold with a plurality of building blocks compared to the scaffold with only one of the building blocks. The scaffold can be coupled to a support. Scaffolds can include functional groups for coupling to, for example, 2, 3, 4, 5, 6, or 7 building blocks.

A scaffold can be the support for an artificial receptor including a combination of 3, 4, or more building blocks occupying distinct positions relative to one another on the scaffold. For example, building block 1 can be adjacent to any of building blocks 2, 3, or 4. This can be illustrated by considering the building blocks coupled to different functional groups on a scaffold. For example, FIG. 8 illustrates positional isomers of 4 different building blocks at the vertices of a quadrilateral shaped scaffold. Scaffold positional isomer artificial receptors can be made, for example, on a scaffold with multiple functional groups that can be protected and deprotected by orthogonal chemistries.

Such a scaffold positional isomer artificial receptor can provide a lead or working receptor with utility distinct from a solid support based receptor. For example, such a scaffold positional isomer can be evaluated and selected for optimal binding, then employed where an optimal receptor is required. The scaffold artificial receptor can be immobilized, for example, on a light fiber to provide a detectable signal or for any of the other applications described herein for working artificial receptors.

A scaffold artificial receptor that has not been immobilized can be used in applications in which an antibody can be used, as a specific anticancer agent, to bind and immobilize/neutralize bloodstream components like cholesterol, cocaine or DDT, to bind and neutralize hazardous wastes, in the development of free solution analysis methods, e.g. fluorescence polarization immunoassay or molecular beacon based assays. Such free (not immobilized) scaffold artificial receptors can also be used for development of pharmaceuticals based on binding, e.g. application of scaffold receptors to block protein-protein interactions which are involved in cancer, the progression of AIDS, the development of tuberculoses and malaria, the toxic effects produced by exposure to industrial chlorinated aromatics, and the like.

In an embodiment, the scaffold artificial receptor is introduced into a subject (e.g., mouse, rat, dog, cat, horse, monkey, human, or the like) through, for example, injection, ingestion, gavage, suppository, inhalation, or the like. Once introduced, the scaffold artificial receptor can bind a compound of interest, such as cocaine, cholesterol, lead, DDT. Binding of the scaffold artificial receptor binding can target the bound material for detection, destruction, excretion, therapy, or the like.

In an embodiment, the scaffold artificial receptor is contacted with an environmental matrix (e.g., water, soil, sediment) through, for example, mixing, spraying, injection, or the like. In the matrix, the scaffold artificial receptor binds a ligand of interest. For a ligand of interest that is a hazardous waste component, a hazardous waste mixture, a pollution component, a pollution mixture, or the like, binding to the scaffold artificial receptor can target the bound material for detection, destruction, or immobilization.

In an embodiment, the scaffold artificial receptor is to a conjugated biological effector. Such a biological effector can be a toxin, a radioisotope chelate, or the like. The conjugate can be introduced into a subject. After introduction, the scaffold artificial receptor conjugate can interact with a ligand of interest that is associated with, for example, a disease causing microbe or a cancer cell. This interaction targets the conjugated toxin or radioisotope chelate to the disease causing microbe or cancer cell for the detection, therapy, destruction of the infectious agent or cancerous cell.

In an embodiment, the scaffold artificial receptor is used in free solution analysis methods. For example a scaffold artificial receptor can include a fluorophore or molecular beacon. Binding of the scaffold artificial receptor conjugate to a ligand of interest or a sample containing a ligand of interest then produces fluorescence polarization or molecular beacon recombination which produces a signal which is related to the presence of the ligand of interest.

In an embodiment, the scaffold artificial receptor can be used as a pharmaceutical, for example, for the treatment of cancer, infection, disease, or toxic effects. As a pharmaceutical, binding of the scaffold artificial receptor to a ligand of interest (e.g., on or in a cell or microbe) can block, for example, DNA replication, gene regulation, RNA transcription, peptide synthesis. Such blocking can disrupt protein (e.g., enzyme) synthesis or modification, protein-protein interactions or the like. Such synthesis, modification, or interactions can be involved in cancer, HIV/AIDS, tuberculosis, malaria, or the toxic effects produced by exposure to industrial chlorinated aromatics or the like. Thus, the scaffold artificial receptor can treat these disorders.

The scaffold molecule can be any of the variety of known molecular scaffolds employed in combinatorial research. Suitable scaffold molecules include those illustrated in Scheme 6. The compounds illustrated in Scheme 6 are either commercially available or can be made by known methods. For example, compounds 1, 2, 4, and 5 are commercially available from Aldrich. Compound 3 can be prepared by the method of Pattarawarapan (2000) (Pattarawarapan, M and Burgess, K, "A Linker Scaffold to Present Dimers of Pharmacophores Prepared by Solid-Phase Synthesis", Angew. Chem. Int. Ed., 39, 4299-4301 (2000)). Compound 6 can be made in the o-$NH_2$ form (shown) by the method of Kimura (2001) (Kimura, M; Shiba, T; Yamazaki, M; Hanabusa, K; Shirai, H and Kobayashi, N, "Construction of Regulated Nanospace around a Porphyrin Core", J. Am. Chem. Soc., 123, 5636-5642 (2001)) and in the p-COOH (not shown) by the method of Jain (2000) (Jain, R K; Hamilton, A D (2000), "Protein Surface Recognition by Synthetic Receptors Based on a Tetraphenylporphyrin Scaffold", Org. Lett. 2, pp. 1721-1723). Compound 7 can be made in the —COOH form (shown) or in the —OH form (not shown) by the method of Hamuro (1997) (Hamuro, Y. et al., (Andrew Hamilton), "A Calixarene with four Peptide Loops: An Antibody Mimic for Recognition of Protein Surfaces", Angew. Chem. Int. Ed. Engl., 36, pp. 2680-2683). Compound 8 can be used with three functional groups in the —$NH_2$ form (shown), with four functional groups including both the —COOH and —$NH_2$ groups (as shown), or as a dimer product with 6-$NH_2$ functional groups (not shown). Each of these forms of compound 8 can be made by the method of Opatz (2001) (Opatz, T; Liskamp, R M (2001), "A Selectively Deprotectable Triazacyclophane Scaffold for the Construction of Artificial Receptors", Org. Lett., 3, pp. 3499-3502).

Scheme 6

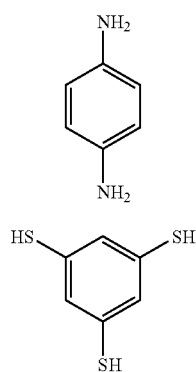

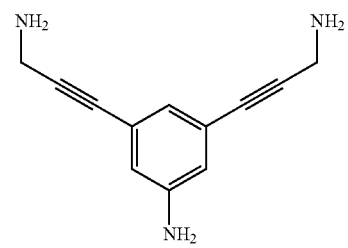

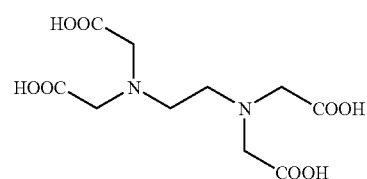

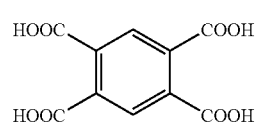

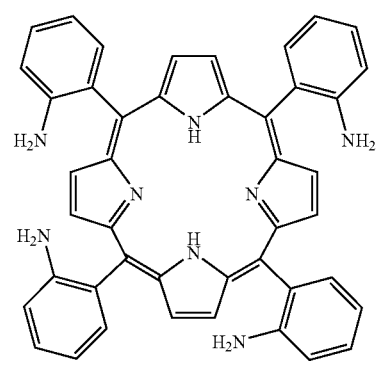

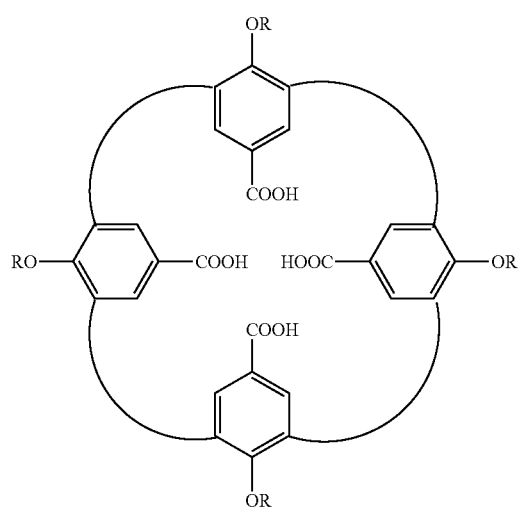

-continued

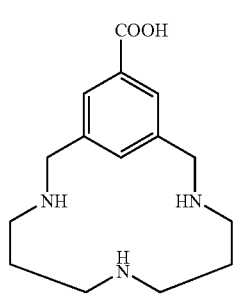

8

Molecular Configurations in Combinations of Building Blocks

Figure 11:
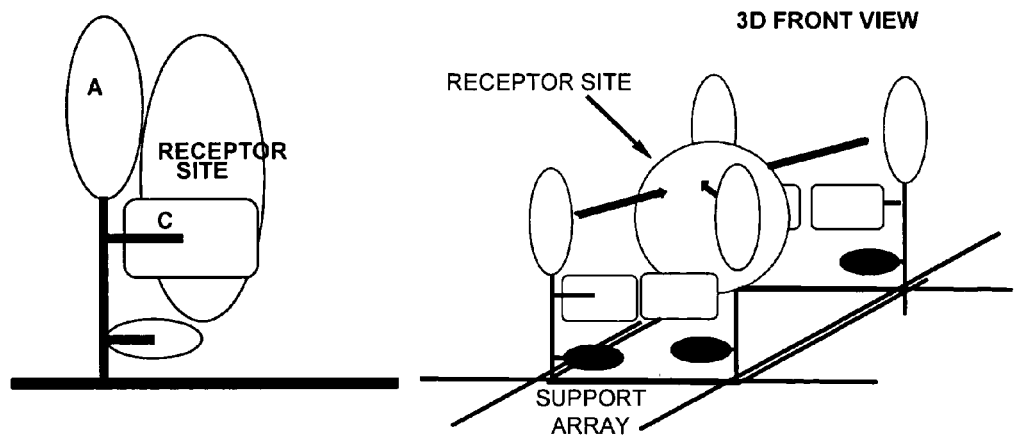
FIG. 11 schematically illustrates embodiments of the present building blocks forming a candidate artificial receptor having a region suitable for binding a test ligand.
Figure 11:
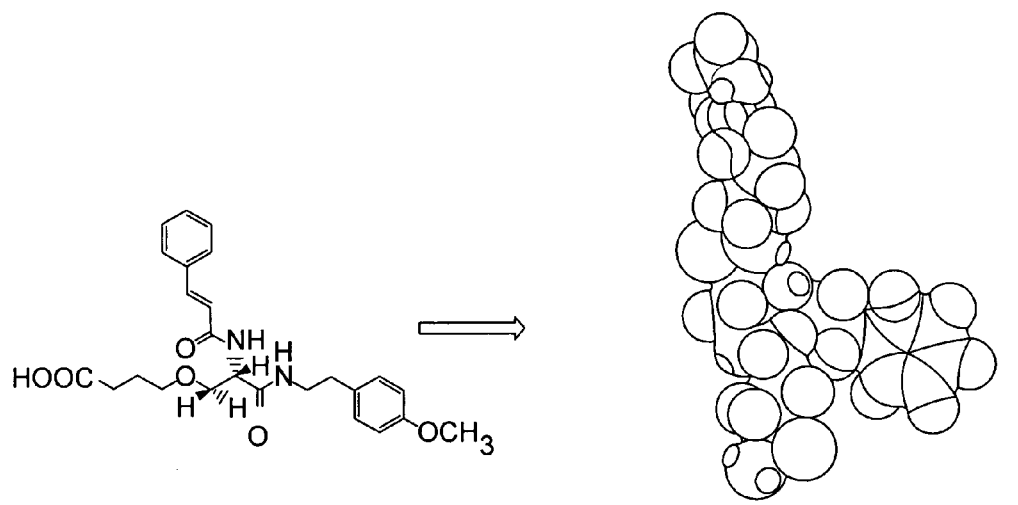
Figure 11:
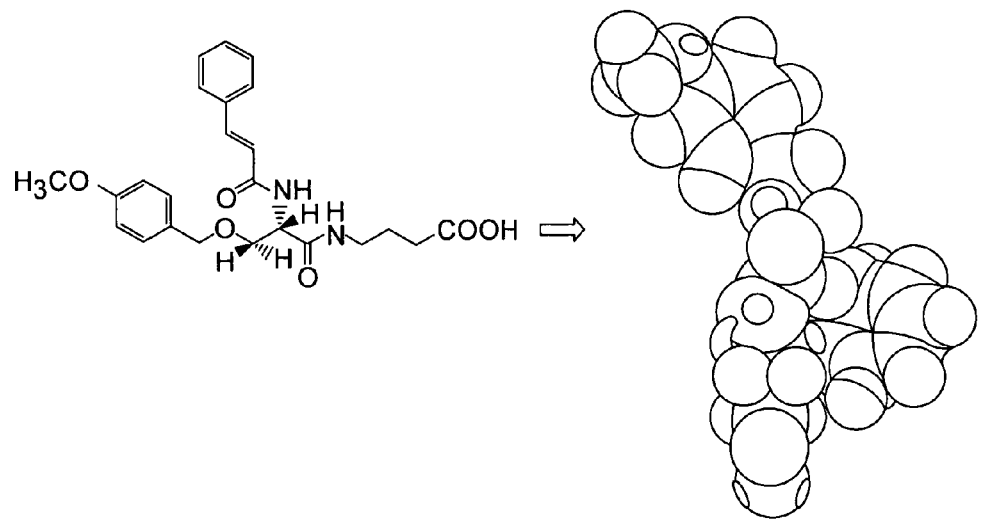

FIG. 11 schematically illustrates a molecular configuration of building blocks that can provide a region for binding for a small molecule ligand. FIG. 11 illustrates that a plurality of adjacent building blocks, each with a pendant and an equatorial recognition element, can form a cavity or other binding site. The binding site can be sized to serve as a receptor for, for example, a small molecule ligand of interest. Space filling molecular models of embodiments of building blocks can be envisioned to fit this schematic. Neighboring building blocks that are different from one another can provide diversity to the binding interactions available in the binding site.

Figure 12:
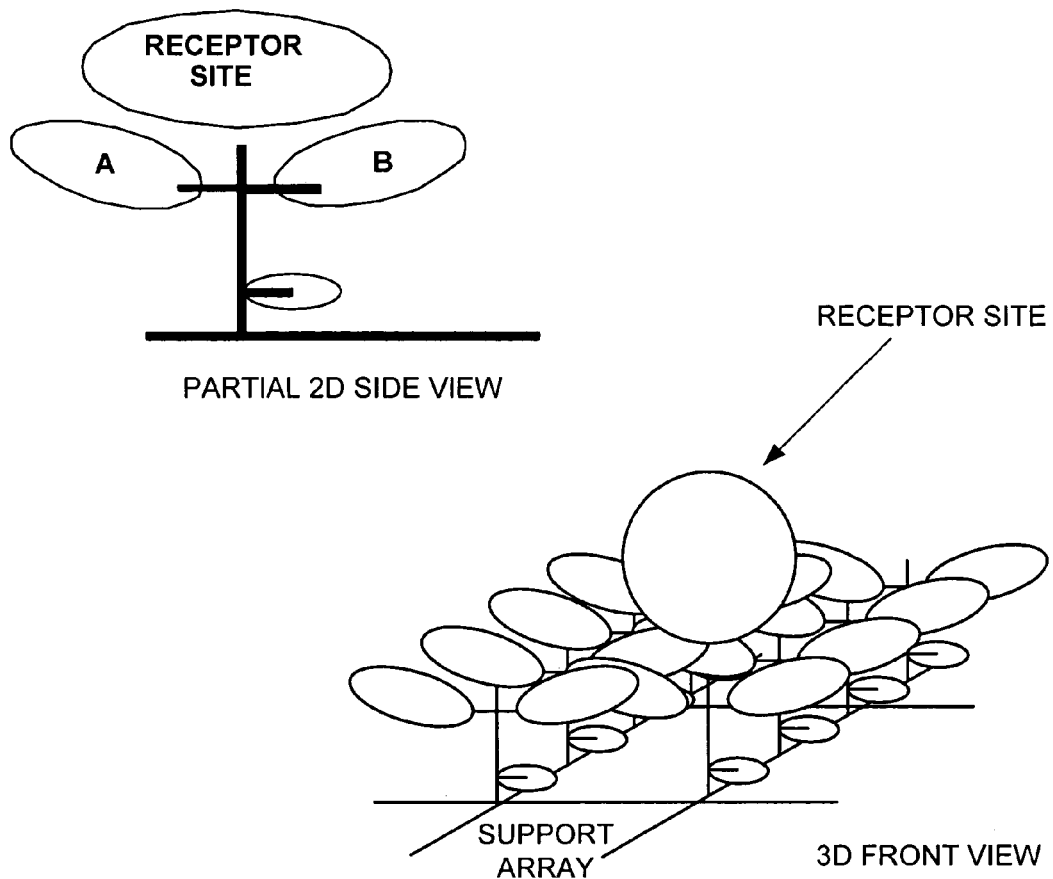
FIG. 12 schematically illustrates embodiments of the present building blocks forming a candidate artificial receptor with a larger molecular footprint.
Figure 12:
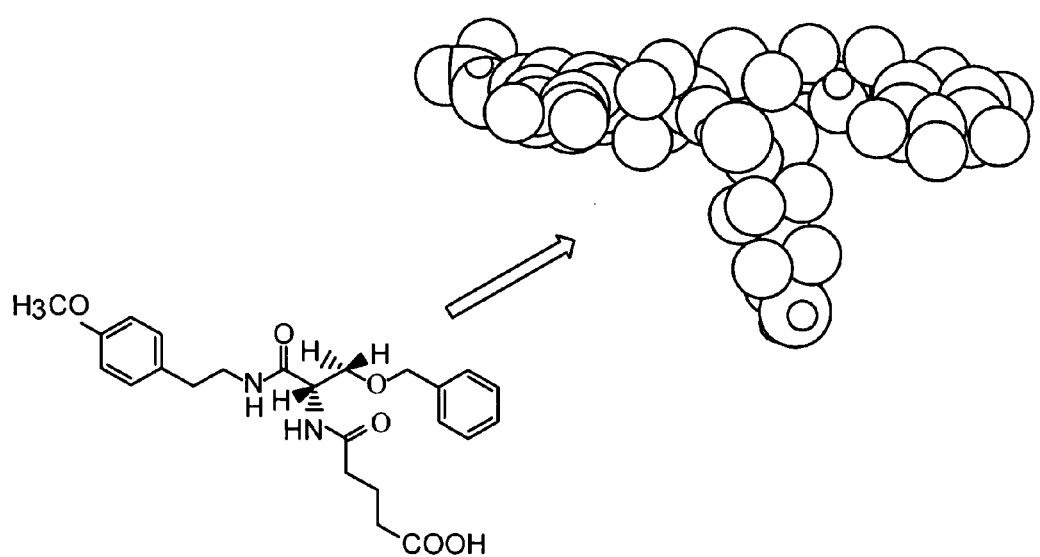

FIG. 12 schematically illustrates a molecular configuration of building blocks that can provide a broad binding site with a large surface area. FIG. 12 illustrates that a plurality of adjacent building blocks, each with two pendant lateral recognition elements, can form a broad binding site with a large molecular footprint. The broad binding site can serve as a receptor for, for example, a macromolecule ligand of interest, a cell, or a microorganism (e.g., a bacterium or a virus). Space filling molecular models of embodiments of building blocks can be envisioned to fit this schematic. Neighboring building blocks that are different from one another can provide diversity to the binding interactions available in the binding site.

Figure 13:
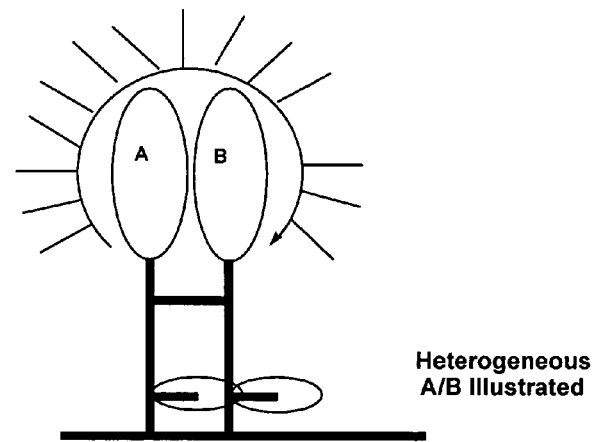
FIG. 13 schematically illustrates embodiments of the present building blocks forming a candidate artificial receptor that is shown as suitable for binding a test ligand with a cavity.
Figure 13:
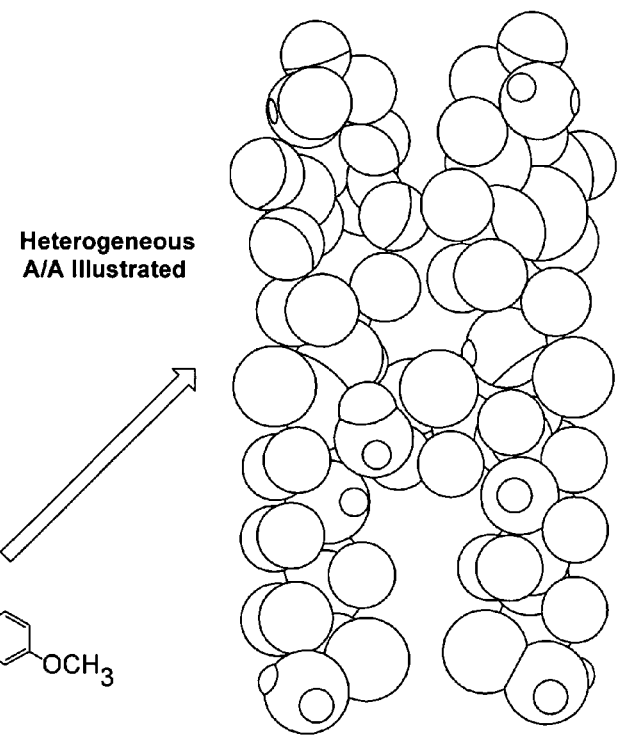

FIG. 13 schematically illustrates a molecular configuration of building blocks arranged to form a protruding binding site, which can, for example, bind a test ligand with a cavity. FIG. 13 illustrates that a plurality of adjacent building blocks, each with a pendant protruding recognition element, can form a protruding binding site. The protruding binding site can serve as a receptor for, for example, a macromolecule having an active or binding site. Space filling molecular models of embodiments of building blocks can be envisioned to fit this schematic. Neighboring building blocks that are different from one another can provide diversity to the binding interactions available in the binding site. The binding site can include recognition elements from 2 or more building blocks.

FIG. 8 illustrates that a molecular configuration of building blocks can form 6 positional isomers. This illustration places the building blocks at corners of a square, but the same is true of 4 vertices of any quadrilateral. Candidate or lead artificial receptors having the structure of the different positional isomers can be made on a scaffold.

Embodiments of Sets as Reagents

The present invention includes sets of building blocks as reagents. Reagent sets of building blocks can include individual or mixtures of building blocks. The reagent sets can be used to make immobilized building blocks and groups of building blocks, and can be sold for this purpose. In an embodiment, the set includes building blocks with recognition elements representing hydrophobic alkyl, hydrophobic aryl, hydrogen bond acceptor, basic, hydrogen bond donor, and small size as structural characteristics. For example, the set can include building blocks of general Formula 2, with $RE_1$, being B1, B2, B3, B4, B5, B6, B7, B8, or B9 and with $RE_2$ being A1, A2, A3, A4, A5, A6, A7, A8, or A9. In an embodiment of the set, $RE_1$, can be B1, B3, B6, or B8 and $RE_2$ can be A2, A4, A5, or A9. In an embodiment of the set, $RE_1$ can be B2, B4, or B6 and $RE_2$ can be A2, A4, or A6. In an embodiment of the set, $RE_1$ can be B2, B4, B6, or B8 and $RE_2$ can be A2, A4, A6, or A8. In an embodiment of the set, $RE_1$, can be B1, B2, B4, B6, or B8 and $RE_2$ can be A1, A2, A4, A6, or A8. In an embodiment of the kit, $RE_1$, can be B1, B2, B3, B4, B5, B6, B7, B8, or B9 and $RE_2$ can be A1, A2, A3, A4, A5, A6, A7, A8, or A9. The building blocks can include as L $(CH_2)_n COOH$, with n=1-16, preferably n=2-8, preferably n=4-6, preferably n=3, or an activated form of L, for example, an activated ester.

The set can be part of a kit including containers of one or mixtures of building blocks, the containers can be in a package, and the kit can include written material describing the building blocks and providing instructions for their use.

The present invention may be better understood with reference to the following examples. These examples are intended to be representative of specific embodiments of the invention, and are not intended as limiting the scope of the invention.

EXAMPLES

Example 1

Synthesis of Building Blocks

Selected building blocks representative of the alkyl-aromatic-polar span of the entire building block grid of Table 2 (above) were synthesized for demonstrating effectiveness of these building blocks for making candidate artificial receptors. These building blocks were made on a framework of general Formula 2, specifically tyrosine, and included recognition element pairs A2B2, A4B4, and A6B6. These recognition element pairs were selected along the diagonal of Table 2, and include enough of the range from alkyl, to aromatic, to polar to represent a significant degree of the interactions and functional groups of the full set of 81 such building blocks.

This selected group of building blocks (N=3) was employed to demonstrate synthesis, candidate artificial receptor array preparation, and detection of lead artificial receptors.

Synthesis

Building block synthesis employed a general procedure outlined in Scheme 7, which specifically illustrates synthesis of a building block of general Formula 2 on a tyrosine framework with recognition element pair A4B4. This general procedure was employed for synthesis of building blocks of general Formula 2, with a tyrosine framework and recognition element pairs A2B2, A4B4, and A6B6, the structures of which are shown in Scheme 8.

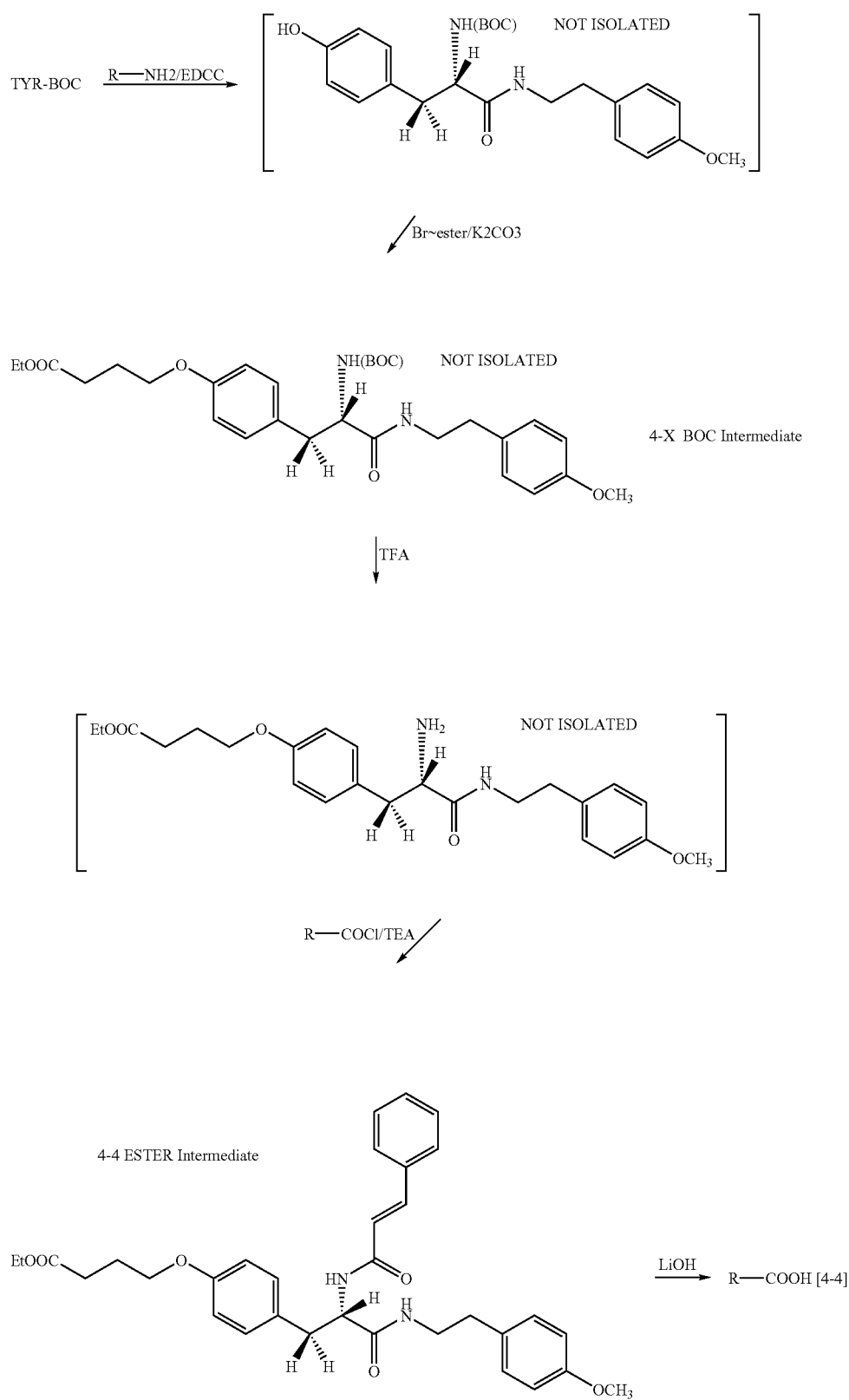

Scheme 8

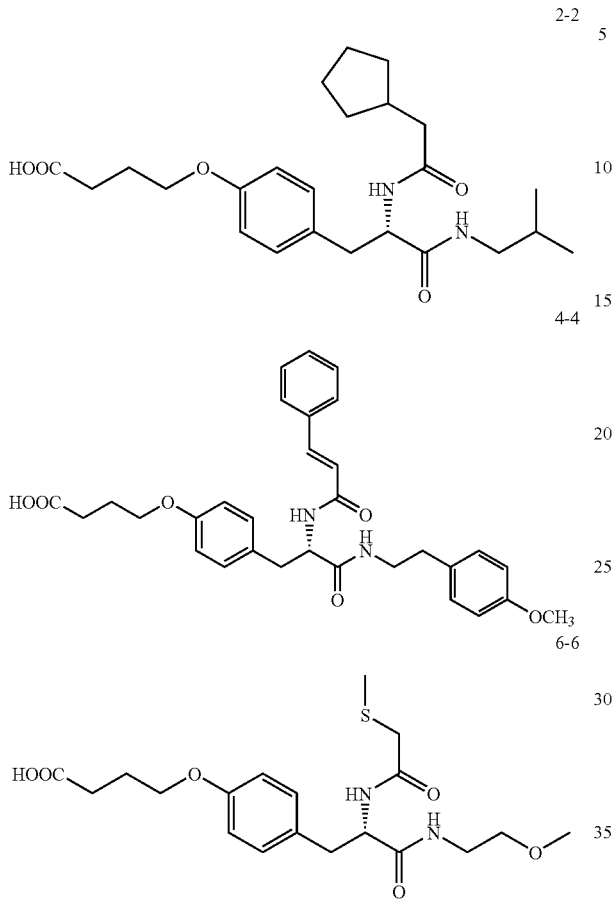

This general procedure was also employed for synthesis of building blocks of general Formula 2, with a linker, tyrosine framework, and recognition element pairs A4B2 and A4B6, the structures of which are shown in Scheme 9. These two building blocks can be referred to as TyrA4B2 and TyrA4B6, respectively. Building blocks TyrA4B2 and TyrA4B6 where readily prepared from the 4-X BOC intermediate by the method of Scheme 10.

Scheme 9

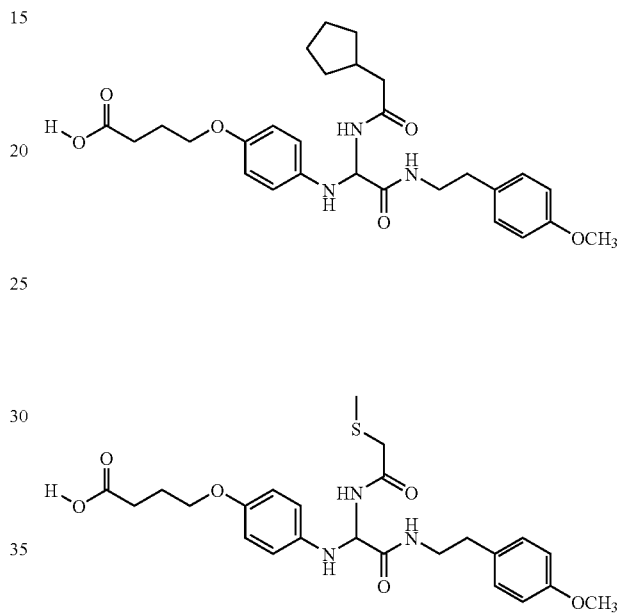

Scheme 10

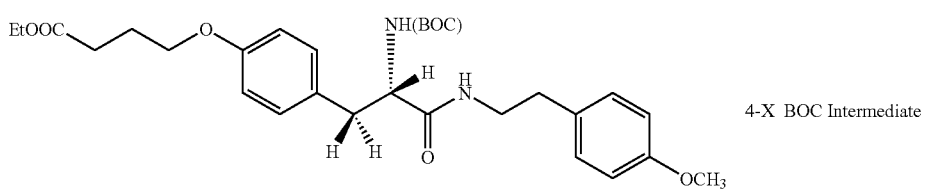

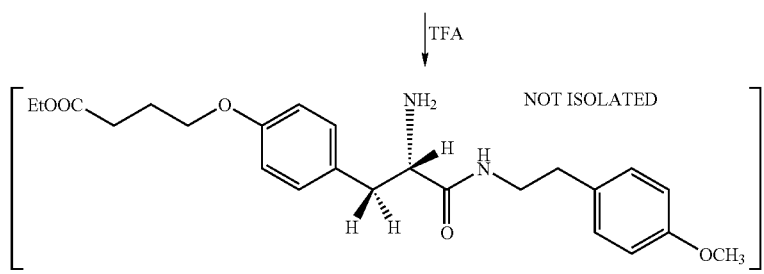

4-R ESTER Intermediate

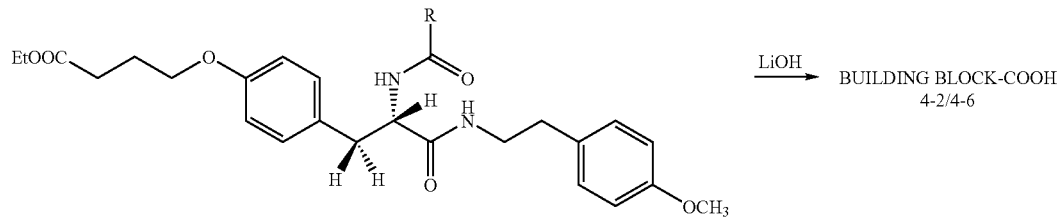

Results

Synthesis of the desired building blocks proved to be generally straightforward. These syntheses illustrate the relative simplicity of preparing the building blocks with 2 recognition elements having different structural characteristics or structures (e.g. A4B2, A6B3, etc.) once the building blocks with corresponding recognition elements (e.g. A2B2, A4B4, etc) have been prepared via their X BOC intermediate.

Synthesis of a building block of general Formula 2 on a tyrosine framework with recognition element pair A4B4 proceeded as illustrated in Scheme 7 to yield the quantities of intermediates and product listed on Table 3.

TABLE 3

Synthesis Data for Building Block TyrA4B4.

| Intermediate or Product | TARE | YIELD | |
|---|---|---|---|
| A4-X BOC | 710 mg | 74% | YIELD from TYR-BOC |
| | 8.20 g | 80% | (2 synthetic steps) |
| A4B4 ESTER | 157 mg | 56% | YIELD from A4-X BOC |
| | 1.26 g | 46% | (2 synthetic steps) |
| TyrA4B4 | 75 mg | 79% | YIELD from A4B4 ESTER |
| | 840 mg | 88% | |

Structures of the two intermediates and of building block TyrA4B4 were verified by proton NMR.

This scheme has also been used to synthesize building blocks TyrA2B2, TyrA4B4, TyrA6B6, TyrA4B2, and TyrA4B6 with the results shown in Table 4:

TABLE 4

Synthesis Data for Building Blocks TyrA2B2, TyrA4B2, TyrA4B6, and TyrA6B6.

| | Intermediate or Product | TARE | YIELD |
|---|---|---|---|
| TyrA2B2 | | | |
| | A2-X BOC | 3.04 g | 68% |
| | A2B2 ESTER | 697 mg | 88% |
| | TyrA2B2 | 163 mg | 87% |
| TyrA4B2 | | | |
| | A4B2 ESTER | 321 mg | 65% |
| | TyrA4B2 | 172 mg | 91% |
| TyrA4B6 | | | |
| | A4B6 ESTER | 173 mg | 37% |
| | TyrA4B6 | 75 mg | 80% |
| TyrA6B6 | | | |
| | A6-X BOC | 3.11 g | 71% |
| | A6B6 ESTER | 436 mg | 45% |
| | TyrA6B6 | 44 mg | 47% |

Summary NMR Data

NMR conditions were 300 MHz in a solvent mixture of deuterochloroform/d-methanol.

TyrA2B2

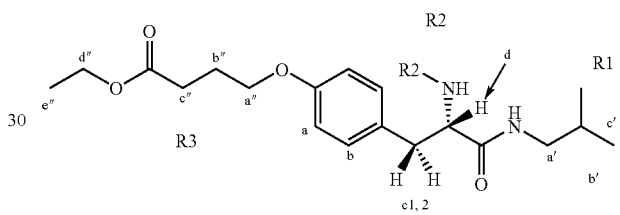

2-X t-BOC R1: -isobutyl R2: t-BOC R3: linker ester 0.82 (m, 6H, c', —CH(C$\underline{H}_3$)$_2$); 1.27 (t, 3H, e", —O—CH$_2$—C$\underline{H}_3$); 1.40 (s, 9H, t-BOC —C(C$\underline{H}_3$)$_3$); 1.68 (m, 1H, b', —C$\underline{H}$(CH$_3$)$^2$); 2.09 (m, 2H, b", —C(O)—CH$_2$—C$\underline{H}_2$—CH$_2$—O—); 2.52 (t, 2H, c", —C(O)—C$\underline{H}_2$—CH$_2$—CH$_2$—O—); 2.82-3.06 (m, 4H, a' and C1,2, AB$\underline{X}$); 4.00 (t, 2H, a", —C(O)—CH$_2$—CH$_2$—C$\underline{H}_2$—O—); 4.15 (q, 3H, d", —O—C$\underline{H}_2$—CH$_3$); 4.21 (m, 1H, d, AB$\underline{X}$); 4.26 (br S, 1H, R1 amide); 6.82 (d, 2H, J=8.6 Hz, a); 7.10 (d, 2H, J=8.6 Hz, b).

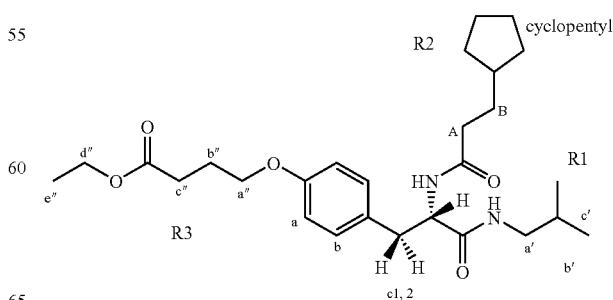

2-2 R3-ester R1: -isobutyl R2:-cyclopentyl R3: linker ester 0.82 (m, 6H, c', —CH(C$\underline{H}_3$)$_2$); 1.04-1.09 (m, 2H, cyclopentyl); 1.27 (t, 3H, e", —O—CH$_2$—C$\underline{H}_3$); 1.45-1.75 (m, 10H, B, cyclopentyl, b', —C$\underline{H}$(CH$_3$)$_2$); 2.08 (m, 2H, b", —C(O)—CH$_2$—C$\underline{H}_2$—CH$_2$—O—); 2.18 (t, 2H, A); 2.52 (t, 2H, c", —C(O)—C$\underline{H}_2$—CH$_2$—CH$_2$—O—); 2.79-3.05 (m, 4H, a' and C1,2, A$\underline{B}$X); 3.98 (t, 2H, a", —C(O)—CH$_2$—CH$_2$—C$\underline{H}_2$—O—); 4.15 (q, 3H, d", —O—C$\underline{H}_2$—CH$_3$); 4.54 (m, 1H, d, AB$\underline{X}$); 4.75 (br S, 2H, R1 and R2 amide); 6.81 (d, 2H, J=8.6 Hz, a); 7.12 (d, 2H, J=8.8 Hz, b).

[2-2] R3-COOH R1: -isobutyl R2: -cyclopentyl R3: linker —COOH 0.82 (m, 6H, c', —CH(C$\underline{H}_3$)$_2$); 1.03-1.08 (m, 2H, cyclopentyl); 1.46-1.73 (m, 10H, B, cyclopentyl, b', —C$\underline{H}$(CH$_3$)$_2$); 2.08 (m, 2H, b", —C(O)—CH$_2$—C$\underline{H}_2$—CH$_2$—O—); 2.16 (t, 2H, A); 2.51 (t, 2H, c", —C(O)—C$\underline{H}_2$—CH$_2$—CH$_2$—O—); 2.80-3.04 (m, 4H, a' and C1,2, A$\underline{B}$X); 3.99 (t, 2H, a", —C(O)—CH$_2$—CH$_2$—C$\underline{H}_2$—O—); 4.54 (m, 1H, d, AB$\underline{X}$); 4.68 (br S, 2H, R1 and R2 amide); 6.82 (d, 2H, J=8.6 Hz, a); 7.12 (d, 2H, J=8.6 Hz, b).

TyrA4B2

A); 2.52 (t, 2H, c", —C(O)—CH$_2$—CH$_2$—CH$_2$—O—); 2.61-2.68 (m, 2H, b', —CH$_2$—C$\underline{H}_2$-phenyl); 2.77-3.02 (m, 2H, C1,2A$\underline{B}$X); 3.26-3.44 (m, 2H, a',—C$\underline{H}_2$—CH$_2$-phenyl); 3.78 (s, 3H, phenyl-OC$\underline{H}_3$); 3.98 (t, 2H, a", —C(O)—CH$_2$—CH$_2$—C$\underline{H}_2$—O—); 4.14 (q, 3H, d", —O—C$\underline{H}_2$—CH$_3$); 4.50 (m, 1H, d, AB$\underline{X}$); 4.62 (br S, 2H, R1 and R2 amides); 6.81 (d, 2H, a); 6.82 (d, 2H, J=8.8 Hz, d'); 7.04 (d, 2H, J=8.6 Hz, b); 7.08 (d, 2H, J=8.6 Hz, c').

[4-2] R3-COOH R1: -methoxyphenyl R2:-cyclopentyl R3: linker —COOH 1.04-1.08 (m, 2H, cyclopentyl); 1.43-1.73 (m, 9H, B, cyclopentyl); 2.08 (m, 2H, b", —C(O)—CH$_2$—C$\underline{H}_2$—CH$_2$—O—); 2.17 (t, 2H, A); 2.50 (t, 2H, c", —C(O)—C$\underline{H}_2$—CH$_2$—CH$_2$—O—); 2.62-2.68 (m, 2H, b', —CH$_2$—C$\underline{H}_2$-phenyl); 2.77-3.02 (m, 2H, C1,2, A$\underline{B}$X); 3.24-3.44 (m, 2H, a', —C$\underline{H}_2$—CH$_2$-phenyl); 3.78 (s, 3H, phenyl-OCH$_3$); 3.99 (t, 2H, a", —C(O)—CH$_2$—CH$_2$—C$\underline{H}_2$—O—); 4.49 (m, 1H, d, AB$\underline{X}$); 6.80-6.85 (m, 4H, a and d'); 7.03-7.09 (m, 4H, b and c').

TyrA4B4

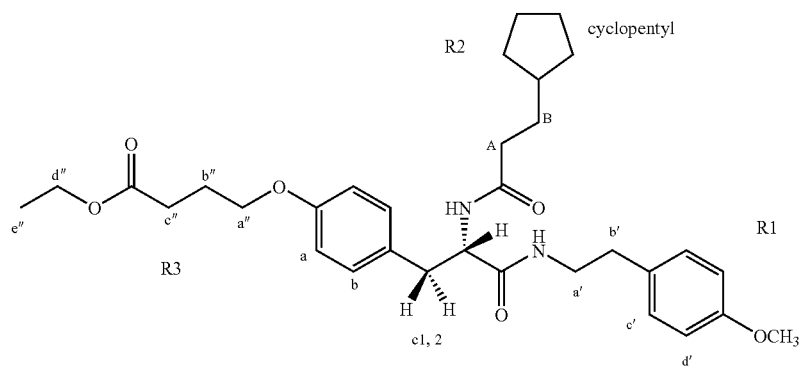

4-2 R3-ester R1: -methoxyphenyl R2:-cyclopentyl R3: linker ester 1.03-1.08 (m, 2H, cyclopentyl); 1.26 (t, 3H, e", —O—CH$_2$—C$\underline{H}_3$); 1.45-1.73 (m, 9H, B, cyclopentyl); 2.09 (m, 2H, b", —C(O)—CH$_2$—C$\underline{H}_2$—CH$_2$—O—); 2.17 (t, 2H,

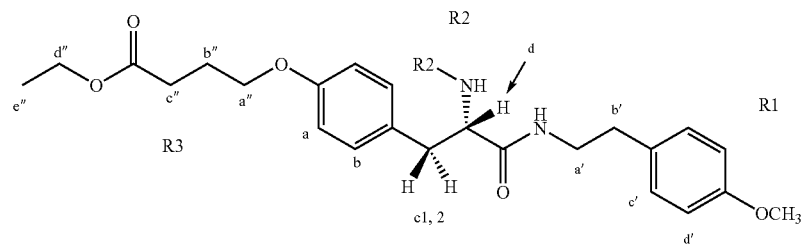

4-X t-BOC R1: -methoxyphenyl R2: t-BOC R3: linker ester 1.26 (t, 3H, e", —O—CH$_2$—CH$_3$); 1.39 (s,9H, t-BOC —C(CH$_3$)$_3$); 2.09 (m, 2H, b", —C(O)—CH$_2$—CH$_2$—CH$_2$—O—); 2.51 (t, 2H, c", —C(O)—CH$_2$—CH$_2$—CH$_2$—O—); 2.63-2.67 (m, 2H, b', —CH$_2$—CH$_2$-phenyl); 2.86-2.93 (m, 2H, C1,2, ABX); 3.24-3.47 (m, 2H, a', —CH$_2$—CH$_2$-phenyl); 3.79 (s, 3H, phenyl-OCH$_3$); 3.98 (t, 2H, a", —C(O)—CH$_2$—CH$_2$—CH$_2$—O—); 4.15 (m, 3H, d", —O—CH$_2$—CH$_3$ and d, ABX); 4.26 (br S, 1H, R1 amide); 6.80-6.83 (m,4H, a and d'); 7.03 (d, 2H, J=8.2 Hz, b); 7.08 (d, 2H, J=8.6 Hz, c').

[4-4] R3-COOH R1: -methoxyphenyl R2:-cinnamic R3: linker —COOH 2.09 (m, 2H, b", —C(O)—CH$_2$—CH$_2$—CH$_2$—O—); 2.50 (t, 2H, c", —C(O)—CH$_2$—CH$_2$—CH$_2$—O—); 2.63-2.67 (m, 2H, b', —CH$_2$—CH$_2$-phenyl); 2.95-3.01 (m, 2H, C1,2, ABX); 3.32-3.42 (m, 2H, a', —CH$_2$—CH$_2$-phenyl); 3.74 (s, 3H, phenyl-OCH$_3$); 3.98 (t, 2H, a", —C(O)—CH$_2$—CH$_2$—CH$_2$—O—); 4.46 (br S, 2H, R1 and R2 amides); 4.61 (m, 1H, d, ABX); 6.53 (d, 1H, J=15.9 Hz, A, —CH=CH-phenyl);

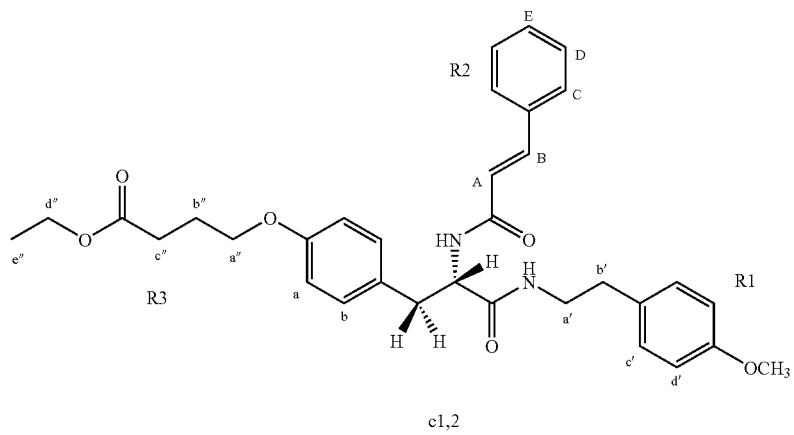

4-4 R3-ester R1: -methoxyphenyl R2:-cinnamic R3: linker ester 1.25 (t, 3H, e", —O—CH$_2$—CH$_3$); 2.08 (m, 2H, b", —C(O)—CH$_2$—CH$_2$—CH$_2$—O—); 2.51 (t, 2H, c", —C(O)—CH$_2$—CH$_2$—CH$_2$—O—); 2.63-2.67 (m, 2H, b', —CH$_2$—CH$_2$-phenyl); 2.95-3.01 (m, 2H, C1,2, ABX); 3.27-3.46 (m, 2H, a', —CH$_2$—CH$_2$-phenyl); 3.73 (s, 3H, phenyl—OCH$_3$); 3.97 (t, 2H, a", —C(O)—CH$_2$—CH$_2$—CH$_2$—O—); 4.13 (q, 3H, d", —O—CH$_2$—CH$_3$); 4.58 (br S, 2H, R1 and R2 amides); 4.62 (m, 1H, d, ABX); 6.55 (d, 1H, J=15.9 Hz, A, —CH=CH-phenyl); 6.78-6.83 (m,4H, a and d'); 7.03 (d, 2H, J=8.6 Hz, b); 7.12 (d, 2H, J=8.6 Hz, c'); 7.37-7.39 (m, 3H, C,E); 7.52-7.57 (m, 3H, B —CH=CH-phenyl and D).

6.78-6.83 (m,4H, a and d'); 7.03 (d, 2H, J=8.4 Hz, b); 7.12 (d, 2H, J=8.4 Hz, c'); 7.37-7.42 (m, 3H, C,E); 7.51-7.58 (m, 3H, B —CH=CH-phenyl and D).

Tyr A4B6

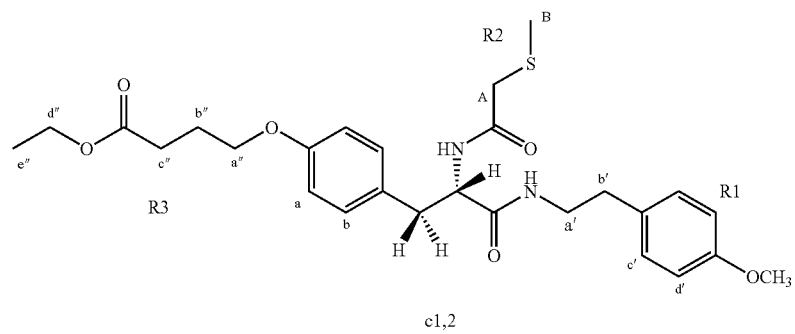

4-6 R3-ester R1:-methoxyphenyl R2:-thioether R3: linker ester 1.26 (t, 3H, e", —O—CH$_2$—CH$_3$); 1.97 (s, 3H, B, —S—CH$_3$); 2.09 (m, 2H, b", —C(O)—CH$_2$—CH$_2$—CH$_2$—O—); 2.52 (t, 2H, c", —C(O)—CH$_2$—CH$_2$—CH$_2$—O—); 2.63-2.69 (m, 2H, b', —CH$_2$—CH$_2$-phenyl); 2.83-3.06 (m, 2H, C1,2, ABX); 3.11 (d, 2H, J=3.7 Hz, A, —C(O)—CH$_2$—S—); 3.27-3.48 (m, 2H, a', —CH$_2$—CH$_2$-phenyl); 3.79 (s, 3H, phenyl-OCH$_3$); 3.98 (t, 2H, a", —C(O)—CH$_2$—CH$_2$—CH$_2$—O—); 4.14 (q, 3H, d", —O—CH$_2$—CH$_3$); 4.51 (m, 1H, d, ABX); 4.55 (br S, 2H, R1 and R2 amides); 6.80-6.84 (m, 4H, a and d'); 7.05 (d, 2H, J=8.6 Hz, b); 7.10 (d, 2H, J=8.6 Hz, c').

[4-6] R3-COOH R1: -methoxyphenyl R2:-thioether R3: linker —COOH 1.96 (s, 3H, B, —S—C$\underline{H}_3$); 2.03-2.10 (m, 2H, b", —C(O)—CH$_2$—C$\underline{H}_2$—CH$_2$—O—); 2.50 (t, 2H, c", —C(O)—C$\underline{H}_2$—CH$_2$—CH$_2$—O—); 2.64-2.70 (m, 2H, b', —CH$_2$—C$\underline{H}_2$-phenyl); 2.82-3.05 (m, 2H, C1,2, A$\underline{B}$X); 3.11 (d, 2H, J=4.2 Hz, A, —C(O)—CH$_2$—S—); 3.30-3.45 (m, 2H, a', —C$\underline{H}_2$—CH$_2$-phenyl); 3.79 (s, 3H, phenyl—OC$\underline{H}_3$); 3.99 (t, 2H, a", —C(O)—CH$_2$—CH$_2$—C$\underline{H}_2$—O—); 4.51 (m, 1H, d, AB$\underline{X}$); 6.81-6.84 (m, 4H, a and d'); 7.05-7.11 (m, 4H, b and c').

Tyr A6B6

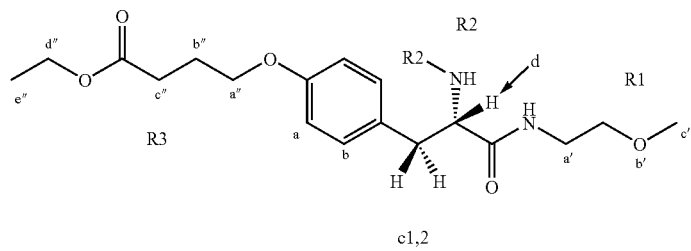

6-Xt-BOC R1: -ether R2: t-BOC R3: linker ester 1.27 (t, 3H, e", —O—CH$_2$—C$\underline{H}_3$); 1.40 (s, 9H, t-BOC —C(C$\underline{H}_3$)$_3$); 2.10 (m, 2H, b", —C(O)—CH$_2$—C$\underline{H}_2$—CH$_2$—O—); 2.52 (t, 2H, c", —C(O)—C$\underline{H}_2$—CH$_2$—CH$_2$—O—); 2.85-3.01 (m, 2H, C1,2, A$\underline{B}$X); 3.28-3.42 (m, 4H, a' and b'); 3.30 (s, 3H, c', —OC$\underline{H}_3$); 3.98 (t, 2H, a", —C(O)—CH$_2$—CH$_2$—C$\underline{H}_2$—O—); 4.08 (br S 1H, R1 amide); 4.15 (q, 3H, d", —O—C$\underline{H}_2$—CH$_3$); 4.22 (m, 1H, d, AB$\underline{X}$); 6.82 (d, 2H, J=8.6 Hz, a); 7.10 (d, 2H, J=8.6 Hz, b).

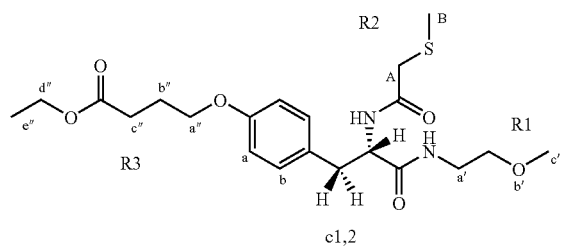

6-6 R3-ester R1: -ether R2:-thioether R3: linker ester 1.27 (t, 3H, e", —O—CH$_2$—C$\underline{H}_3$); 1.99 (s, 3H, B, —S—C$\underline{H}_3$); 2.09 (m, 2H, b", —C(O)—CH$_2$—C$\underline{H}_2$—CH$_2$—O—); 2.52 (t, 2H, c", —C(O)—C$\underline{H}_2$—CH$_2$—CH$_2$—O—); 2.87-3.10 (m, 2H, C1,2, A$\underline{B}$X); 3.13 (d, 2H, J=4.6 Hz, A, —C(O)—C$\underline{H}_2$—S—); 3.29-3.44 (m, 4H, a' and b'); 3.33 (s, 3H, c', —OC$\underline{H}_3$); 3.99 (t, 2H, a", —C(O)—CH$_2$—CH$_2$—C$\underline{H}_2$—O—); 4.15 (q, 3H, d", —O—C$\underline{H}_2$—CH$_3$); 4.55-4.60 (m, 1H, d, AB$\underline{X}$); 4.57 (br S, 2H, R1 and R2 amide); 6.82 (d, 2H, J=8.6 Hz, a); 7.13 (d, 2H, J=8.6 Hz, b).

[6-6] R3-COOH R1: -ether R2:-thioether R3: linker —COOH 1.98 (s, 3H, B, —S—C$\underline{H}_3$); 2.08 (m, 2H, b", —C(O)—CH$_2$—C$\underline{H}_2$—CH$_2$—O—); 2.51 (t, 2H, c", —C(O)—C$\underline{H}_2$—CH$_2$—CH$_2$—O—); 2.86-3.10 (m, 2H, C1,2, A$\underline{B}$X); 3.13 (d, 2H, J=4.8 Hz, A, —C(O)—C$\underline{H}_2$—S—); 3.28-3.44 (m, 4H, a' and b'); 3.33 (s, 3H, c', —OC$\underline{H}_3$); 3.99 (t, 2H, a", —C(O)—CH$_2$—CH$_2$—C$\underline{H}_2$—O—); 4.55-4.60 (m, 1H, d, AB$\underline{X}$; 6.83 (d, 2H, J=8.8 Hz, a); 7.14 (d, 2H, J=8.4 Hz, b).

Example 2

Preparation of Candidate Artificial Receptors

The comparatively small numbers of candidate artificial receptors made from combinations of 3 or 5 building blocks were prepared in 12×75 borosilicate glass test tubes. The inner surface of the tube was modified using standard glass derivatization chemistry. The modified tubes were convenient vessels for the test ligand binding experiments.

The three tyrosine framework building blocks TyrA2B2, TyrA4B4, and TyrA6B6 resulted in three receptors homogeneous in building block (A2B2, A4B4, and A6B6), three receptors heterogeneous in building block and containing two building blocks (A2B2 plus A4B4, A2B2 plus A6B6, and A4B4 plus A6B6), and one receptor heterogeneous in building block and containing three building blocks (A2B2 plus A4B4 plus A6B6).

Preparation of Amino-Glass

The first step in the tube or other glass derivatization process was to covalently immobilize a pendant functional group on the glass surface. The reaction of an aminoethyl silicon reagent with the glass was a straightforward method for the introduction of a pendant amine which was subsequently used for receptor preparation (FIG. 5). Amine modification was accomplished by the protocol of Schreiber (MacBeath et al. (1999) J. Am. Chem. Soc., 121, 7967-7968).

Briefly, tubes were soaked in water for 1-2 hr then drained for 30-60 min. The tubes are then treated overnight with "Piranha" solution: 70/30 (v/v) conc. $H_2SO_4$/30% $H_2O_2$. Each 12×75 received about 0.6 mL of this solution and was loosely covered with aluminum foil. The next day, the solution was decanted and the tubes were rinsed with water and drained. The tubes were then treated with amino silane solution. The tubes were filled with 0.5 mL of a solution of 3% amino silane in 95% ethanol, covered with foil, and allowed to stand for 60 min. The solution was decanted. The tubes were rinsed with ethanol, drained, and then heated at 125° C. for 60 min. The tubes were rinsed again with ethanol, drained, and allowed to dry overnight.

Evaluation of Amino-Glass

The load of amine on the glass surface was determined by the method provided by Pierce Chemical Co. as modified by Schreiber (MacBeath et al. (1999) supra). The method was further modified to include THF/$H_2O$ washes to remove non-covalently bound label. This method, including the additional step, gave consistent semi-quantitative results.

Briefly, the method employed in these studies included adding to the amino tubes about 2 ml of pH 8.5 NaHCO$_3$ (4.20 grams of NaHCO$_3$ per liter) and soaking for 5 min. The bicarbonate solution was decanted and the tubes drained. The tubes were then reacted with an SDTB (Pierce) labeling solution (SDTB in HPLC grade DMF and pH 8.5 NaHCO$_3$). The solution was made and immediately added to the tubes, which then were shaken for 30-45 min. The solution was decanted and the tubes were washed repeatedly with water and THF and then water. After addition of 1 mL of 30% perchloric acid, OD at 498 nm was read. A load of 2 amines per square nm gives an OD of 0.07 for 12×75 mm tubes.

Over several batches of tubes (about 1000 tubes), loading of about 2.3 amines per square nm was achieved. Such amine loads were well within the densities required for these studies.

Preparation of Candidate Artificial Receptors

Functionalization of the amine modified glass surface was accomplished by reaction with activated carboxyl derivatives to form the amide (see, e.g., FIG. 5). This reaction employed the linker carboxyl in certain embodiments of the building blocks, e.g., certain embodiments having Formula 2.

In the present example, coupling of linker carboxyl containing building blocks to the amine support matrix was conducted generally according to established methods for coupling carboxyl containing compounds to amines on supports (the Pierce method (Pierce Chemical Co.) as described by Schreiber (MacBeath et al. (1999) supra)). The building block linker carboxyl group was activated by reacting the building block with carbodiimide in the presence of sulfo N-hydroxysuccinimide in aq. DMF solution. After overnight activation of the carboxyl to the sulfoNHS activated ester, the building block was reacted directly with the amino glass. Coupling combinations of building blocks to the amino-glass was accomplished by premixing of activated building blocks prior to addition to the amino tube. Support matrix amines not reacted with building block were acetylated by the same general method.

Briefly, building block amide and other glass supports were prepared by adding to amino-glass tubes 2 mL of pH 8.5 NaHCO$_3$ for 10 min. The tubes were decanted and drained. Activated building block(s) or acetic anhydride were dissolved in DMF/ pH 8.5 NaHCO$_3$ and added to the amino-glass tubes. The tubes were shaken for 60 min, decanted, and washed with aq. THF and/or water. The tubes were used immediately and also after drying and storage. Activated carboxyl groups were typically in more than 50-fold excess over amines.

Derivatized tubes prepared by this procedure included those listed in Table 5.

TABLE 5

Summary of Amide Tubes Prepared.

| TUBE | DESCRIPTION |
|---|---|
| —NH2 | pendant amine |
| —Ac | acetamide |
| -22 | Homogeneous immobilized building block TyrA2B2 |
| -44 | Homogeneous immobilized building block TyrA4B4 |
| -66 | Homogeneous immobilized building block TyrA6B6 |
| -22/44 | Candidate artificial receptor TyrA2B2 plus TyrA4B4 (building block heterogeneous) |
| -22/66 | Candidate artificial receptor TyrA2B2 plus TyrA6B6 (building block heterogeneous) |
| -44/66 | Candidate artificial receptor TyrA4B4 plus TyrA6B6 (building block heterogeneous) |
| -22/44/66 | Candidate artificial receptor TyrA2B2, TyrA4B4, plus TyrA6B6 (building block heterogeneous) |

Building block incorporation was determined as described above for evaluation of amino-glass. This evaluation indicated that the amide forming reaction produced candidate artificial receptors including substantial amounts of building block, for example, 30 to 80% of the amines were derivatized by building block. As shown below, binding to the candidate artificial receptor was observed when 30% or more of amines were derivatized with building block.

Example 3

Screening Test Ligands Against Candidate Artificial Receptors Made From 3 Building Blocks In this example, candidate artificial receptors were tested for their ability to bind to test ligands. The test ligands were coupled horseradish peroxidase (HRP). Conjugates of test ligand with HRP were readily prepared by known methods, were stable in solution, and were detected in picogram quantities.

Materials and Methods

Preparation of Labeled Test Ligand

Conjugates of HRP and test ligand were prepared by first modifying HRP to incorporate additional pendant amine groups. Briefly, EIA grade HRP (e.g., SIGMA P-6782) was dissolved in water and oxidized with NaIO4 at about 4° C. in the dark or in subdued light. The oxidized HRP was subjected to gel filtration chromatography (e.g., SEPHADEX® G-25 equilibrated with 100 mM pH 9.4 borate buffer). The resulting solution of oxidized HRP was reacted with ethylene diamine dihydrochloride for about 30 min. at 4° C. The derivatized HRP was then reduced with NaBH$_4$ to yield amine derivatized HRP (amino-HRP). The amino-HRP was then dialyzed against the borate buffer for about 8 hours with a single change of dialysis solution.

Then, the amino-HRP was further modified to form amide links to the test ligand. Briefly, a carboxyl group containing derivative of the test ligand was converted to an activated ester using the method described above for building blocks. The activated test ligand and the amino-HRP were reacted overnight with eventual addition of 10-100 fold excess of activated test ligand to amines on the amino-HRP. The conjugate of test ligand with HRP (HRP-ligand conjugate) was purified by gel filtration chromatography and/or dialysis, as described above. These conjugates were stored at 4° C. in PBS solution with 20 µl Tween-20 added per liter of PBS. Analyte load was determined by the UV/Vis absorbance of the analyte and/or by amine loss.

FIG. 14 illustrates HRP (Formula H1), HRP derivatives (Formulas H2 and H3), and conjugates of test ligand and HRP (Formulas H4, H5, and H6) that have been made for and used in these examples. HRP has a molecular weight of 40,000 and 2 free amines in its native form. Native HRP was oxidized to form amine HRP with about 20 amino groups on its surface. Amide derivatives of amino HRP were formed by reacting the amino HRP with a anhydride or acid chloride. Preferred amide HRPs include the acetamide derivative. HRP test ligand conjugates were formed, for example, by reacting amine HRP with an activated ester form of a test ligand.

Evaluating Binding of Test Ligands to Candidate Artificial Receptors

Candidate artificial receptors were prepared as described in Example 2. Binding of test ligand to candidate artificial receptors was evaluated by the following procedure. Briefly, one or more tubes, each containing a candidate artificial receptor, were rinsed with PBS, decanted, and drained. PBS (250 µl) was added to the tube, HRP-ligand conjugate was added (20 µl), and the candidate artificial receptors were incubated at room temperature for the desired time, for example, 30 min or longer. The 20 µl aliquot of HRP conjugate typically included a concentration of 1.0 µg/ml, 0.1 µg/ml, and/or 0.01 µg/ml of the conjugate. This concentration in the aliquot is referred to as the test concentration and is shown on Figures. The tubes were decanted, rinsed twice with PBS, rinsed with water, decanted, and drained. Then color was developed with an HRP substrate, for example, the HRP chromogen (source: BioFX Corp.). Typically, 450 µl of substrate was added and the tubes were incubated for 15 min. Then, the chromogen solution was quickly transferred to a clean test tube and 600 µl of stop solution (0.1 N HCl) was added. The stopped tubes were read at 450 nm.

The receptor tubes, which were not exposed to the strongly acidic stop solution, were prepared for reuse in subsequent experiments by rinsing with water and with PBS, followed by addition of 2 ml PBS. The tubes were soaked with buffer and rinsed as needed to remove the bound HRP-ligand conjugate.

Results and Discussion

Experiment 1:

Experiment 1 demonstrated at least that:

a) the relative binding of a particular HRP-ligand conjugate was consistently reproduced over a series of tube preparations and over a period of several weeks;

b) that HRP-ligand conjugates gave differential responses to simple floor/receptor surfaces;

c) the nature of the floor played a role in binding.

The differential response to simple floor/receptor surfaces is illustrated by the data presented in Table 6. The data in the last two rows of this table demonstrate that the nature of the group derivatizing remaining amines (those not reacted with building block) affected binding to a candidate receptor. In this experiment, the test ligand bound better to the building block with free amine on the "floor" compared to building block with acetamide floor.

TABLE 6

Test Ligand Binds Better to an Immobilized Building Block than to Floor Surfaces

| Test Ligand, 1.0 µg/ml (as ligand-HRP conjugate) | Tube or Building Block | OD (std dev) |
| --- | --- | --- |
| Acetate | bare amino tube | 0.14 (0.03) |
| Acetate | acetylated amino tube | 0.05 (0.03) |
| Acetate | TyrA4B4 | >2.8 |
| TCDD | bare amino tube | 1.65 (0.39) |
| TCDD | acetylated amino tube | 0.11 (0.09) |
| TCDD | TyrA4B4 | >2.8 |
| TCDD | TyrA4B4 with acetylated floor | 0.77 |

Experiment 2:

Experiment 2 demonstrated at least that:

a) Receptor binding was sensitive to both the structure and the concentration of the HRP derivative.

b) The HRP moiety was not a significant factor in the observed binding patterns. Binding of the HRP-NH-Ac control was minimal with respect to test ligand binding c) Binding was controlled by both kinetic and thermodynamic factors.

d) Simple partition coefficient driven equilibria were not responsible for the observed test ligand binding to the inventive candidate artificial receptors.

e) An unknown sample containing a test ligand can be identified by its distinct binding pattern.

In Experiment 2, six test ligands (as ligand-HRP conjugates) were tested against 4 candidate artificial receptors, 3 homogenous immobilized building blocks, acetylated amino-glass, and amino-glass. The results of Experiment 2 are illustrated in FIGS. 15-18.

Figure 15A:
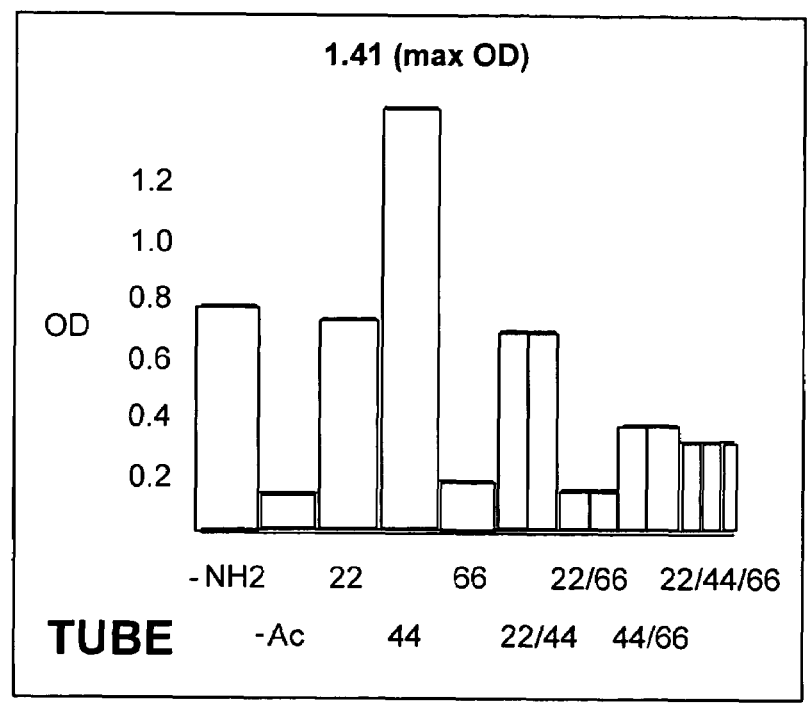
FIG. 15A illustrates a key for the bar charts of FIGS. 15B-20 and 22. This key identifies the bars for amino-glass, for acetylated amino-glass, for each of homogeneous immobilized building blocks TyrA2B2 (22), TyrA4B4 (44), and TyrA6B6 (66), and for candidate artificial receptors TyrA2B2 plus TyrA4B4 (22/44); TyrA2B2 plus TyrA6B6 (22/66); TyrA4B4 plus TyrA6B6 (44/66); and TyrA2B2, TyrA4B4, plus TyrA6B6 (22/44/66). Each bar for an artificial receptor including two building blocks is illustrated as 2 adjacent vertical stripes or segments. The bar for an artificial receptor including three building blocks is illustrated as 3 adjacent vertical stripes or segments.
Figure 15B:
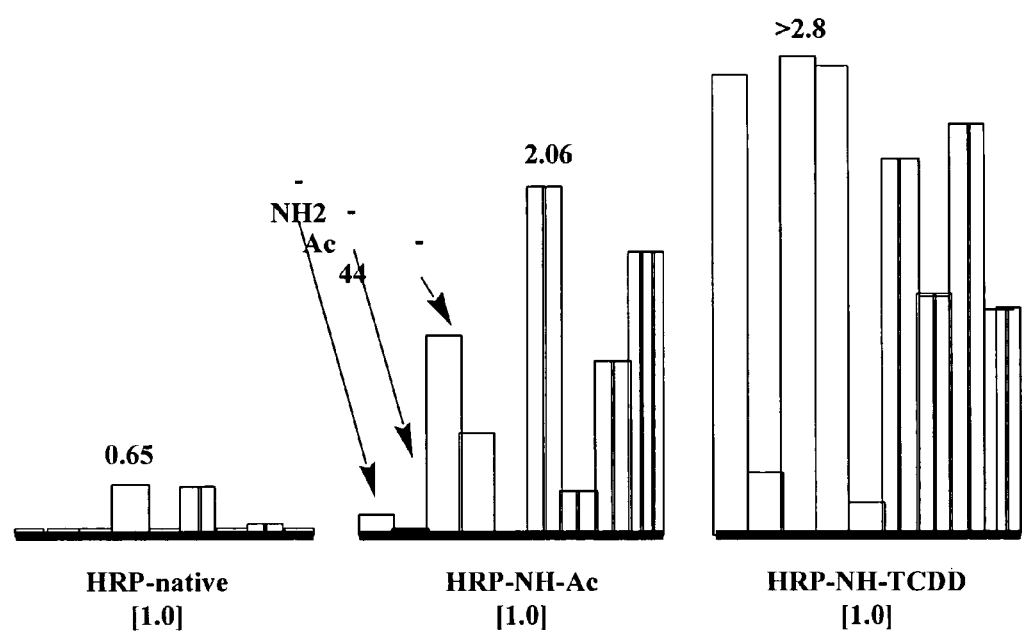
FIG. 15B illustrates bar charts of the binding pattern comparison for native HRP, acetylated amino-HRP, and the TCDD derivative of amino-HRP. This Figure illustrates binding of this test ligand and these control derivatives to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6. The abbreviation for the building block including a linker, a tyrosine framework, and recognition elements AxBy is TyrAxBy.

FIG. 15 illustrates bar charts of the binding pattern comparison for native HRP, acetylated-HRP, and the TCDD derivative of amino-HRP. The values in FIG. 15 were taken from the mean values listed in Table 6. This Figure illustrates binding of this test ligand and these control HRP derivatives to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6. The HRP derivatives were tested at 1 µg/ml (20 µL of which includes only 20 ng of HRP, or picomole amounts of the test ligand) against the suite of 9 control, building block, and receptor surfaces. In this experiment OD values were linear up to about 2.4 and then increased non-linearly.

Note that these data are consistent with the results of Experiment 1 and extend those first results to demonstrate that receptor binding was sensitive to both the structure and the concentration of the HRP derivative. The results illustrated in FIG. 15, which include the binding pattern for native HRP, also demonstrate that the HRP moiety was not a significant factor in the observed binding patterns when compared to the binding of a ligand-HRP conjugate, e.g. HRP-NH-34K, HRP-NH-ETU, or HRP-NH-TCDD.

Binding of the HRP moiety, which was used as the binding screen label, to candidate receptors would cause false positives. FIG. 15 illustrates that native HRP did not show significant non-specific binding to either the control or candidate receptor tubes at the highest concentration of HRP used for these studies.

Figure 16:
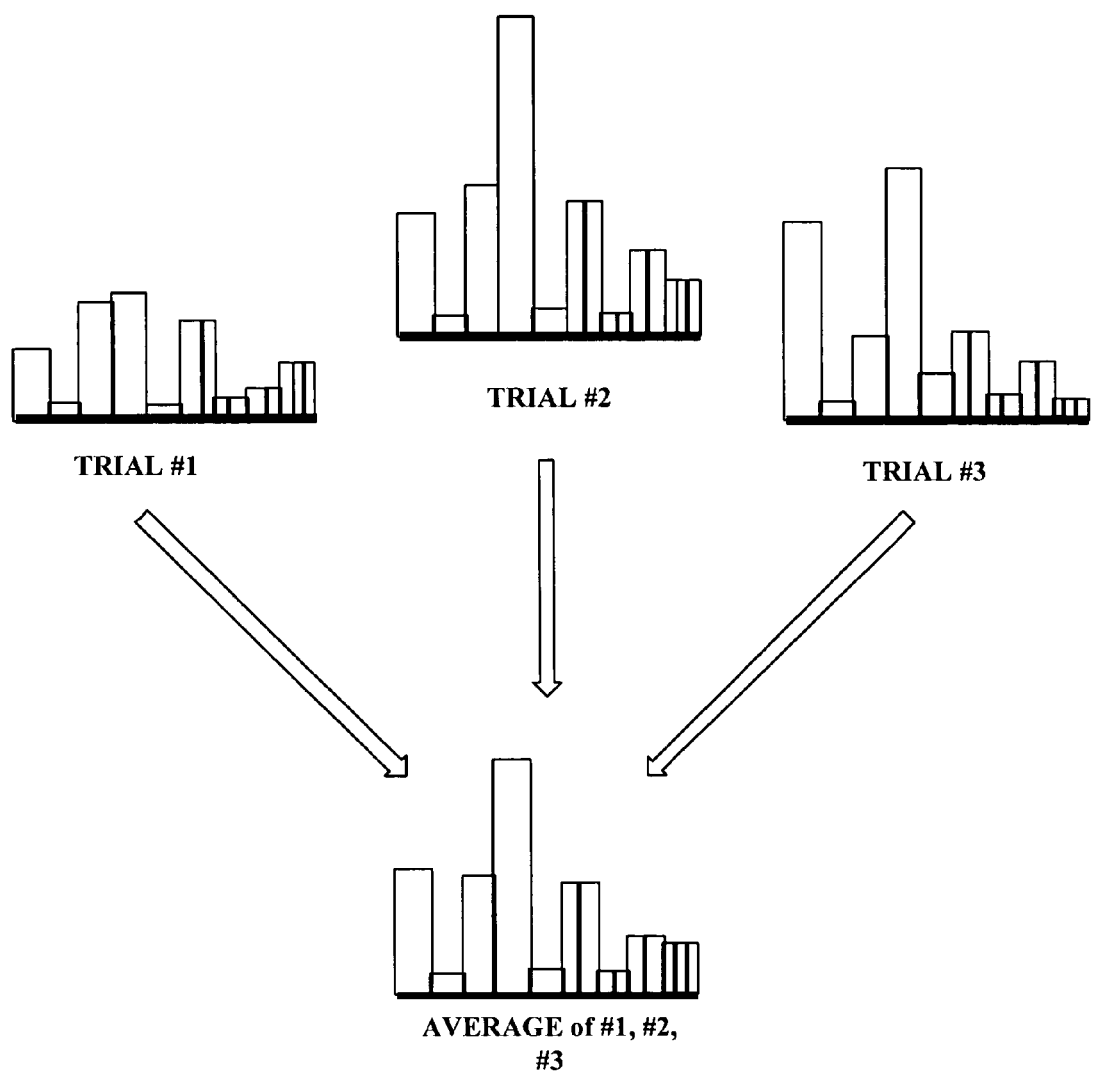
FIG. 16 illustrates bar charts showing the reproducibility of the binding pattern for amino-HRP to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6.

FIG. 16 illustrates bar charts showing the reproducibility of the binding pattern for amino-HRP to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6. FIG. 16 illustrates that both the relative binding OD and binding pattern were consistent over a triplicate screen of HRP-NH2 versus the 9 control, building block, and receptor surfaces. The data illustrated in FIG. 16 show that pattern of relative OD values for each homogeneous immobilized building block or receptor was essentially the same between the trials. The following order was observed from highest to lowest OD: 1) TyrA4B4; 2-4) amino glass TyrA2B2, and TyrA2B2 plus TyrA4B4; 5-6) TyrA4B4 plus TyrA6B6, and TyrA2B2, TyrA4B4 plus TyrA6B6; 7-9) acetylated amino glass, TyrA6B6, and TyrA2B2 plus TyrA6B6.

Figure 17:
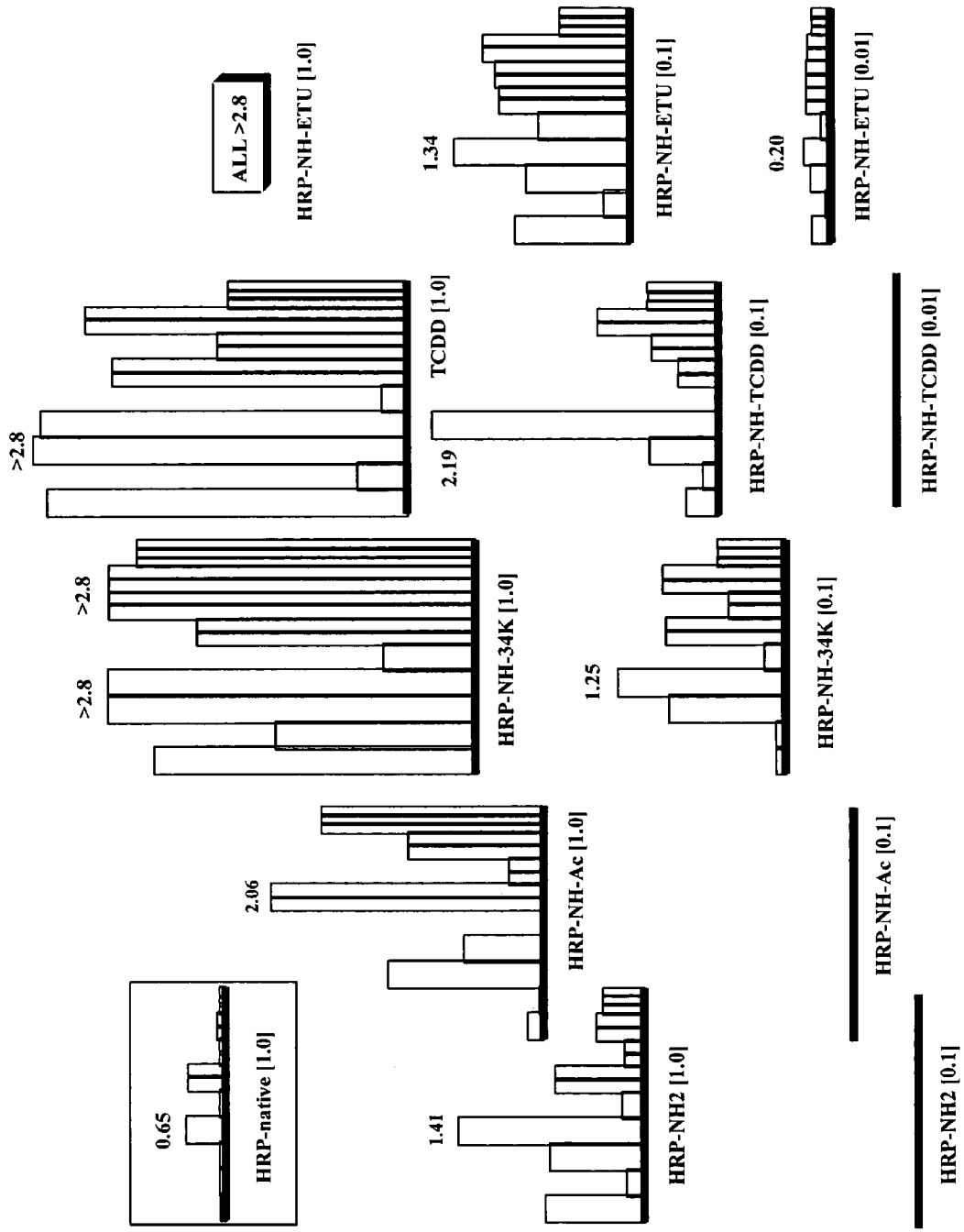
FIG. 17 illustrates bar charts of the binding pattern comparison for native HRP (Formula H1), amino-HRP (Formula H2), acetylated amino-HRP (Formula H3), the 34K derivative of amino-HRP (Formula H4), the TCDD derivative of amino-HRP (Formula H6), and the ETU derivative of amino-HRP (Formula H5). This Figure illustrates binding of these test ligand conjugates and these control derivatives to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6.

FIG. 17 illustrates bar charts of the binding pattern comparison for native HRP, amino-HRP, the 34K derivative of amino-HRP (Formula H4), the TCDD derivative of amino-HRP (Formula H6), and the ETU derivative of amino-HRP (Formula H5). These were tested at 1 µg/ml, 0.1 µg/ml, and 0.01 µg/ml. This Figure illustrates binding of this test ligand and these control derivatives to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6. The results shown in FIG. 17 demonstrate observed concentration dependent binding, which reflected the different binding affinities of the receptor surfaces for the test ligands and differential patterns of binding to the control, building block, and receptor surfaces by the test ligands.

The target screen was based on the binding of HRP labeled test ligand. Binding of the HRP-NH-Ac derivative should be minimal with respect to binding of HRP-test ligand conjugate to give the best signal for target binding. As illustrated by the data for HRP-NH-Ac (0.1X concentration) compared to the HRP-NH-34K, ETU, TCDD conjugates (FIG. 17), the binding of the HRP-NH-Ac control was minimal with respect to test ligand binding.

Figure 18:
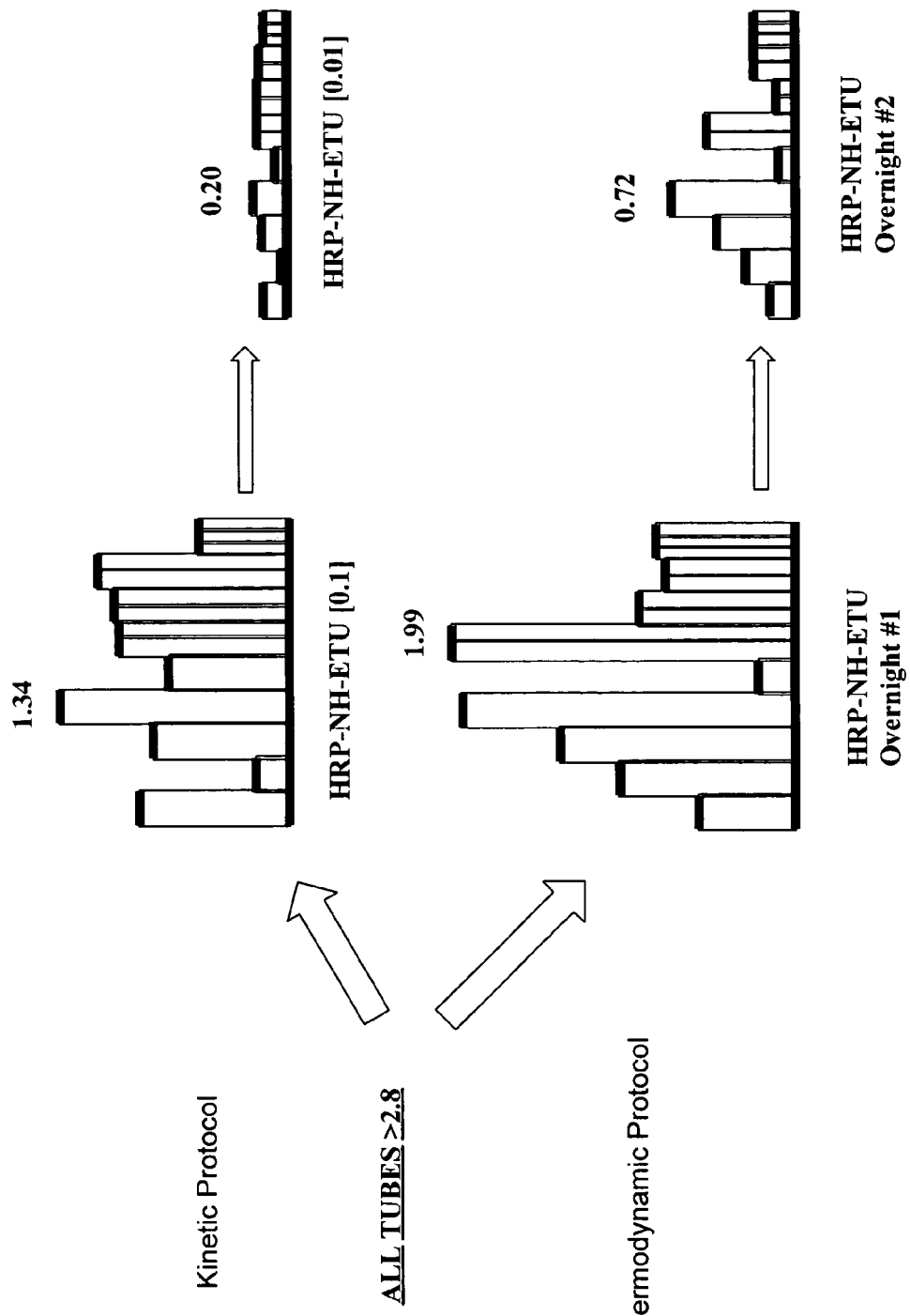
FIG. 18 illustrates bar charts of the binding pattern comparison for the ETU derivative of amino-HRP (Formula H2) using kinetic and thermodynamic protocols for determining binding. This Figure illustrates binding of this test ligand conjugate to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6.

FIG. 18 illustrates bar charts of the binding pattern comparison for the ETU derivative of amino-HRP (Formula H5) using two different protocols for determining binding. In the kinetic protocol, the HRP conjugate at 0.1 and 0.01 µg/ml was added to the tube, incubated, then decanted. The tubes were rinsed and HRP chromogen was developed within about 30 min of adding ligand to receptor. In the thermodynamic protocol, HRP conjugate at 1 µg/ml and was added to the tube and decanted after incubation. Then the tube was rinsed with buffer, more buffer was added to the tube, and it was incubated overnight (overnight #1). This rinse, adding, and incubating was repeated for overnight #2. This Figure illustrates binding of this test ligand and these control derivatives to amino-glass, to acetylated amino-glass, to each of homogeneous immobilized building blocks TyrA2B2, TyrA4B4, and TyrA6B6, and to candidate artificial receptors TyrA2B2 plus TyrA4B4; TyrA2B2 plus TyrA6B6; TyrA4B4 plus TyrA6B6; and TyrA2B2, TyrA4B4, plus TyrA6B6.

The results shown in FIG. 18 demonstrate that binding was controlled by both kinetic and thermodynamic factors. This extends the results discussed above. The kinetic assay detects those candidate artificial receptors to which the test ligand binds quickly, kinetic factors predominate. The thermodynamic assay detects those candidate artificial receptors to which the test ligand binds more slowly but more tightly, thermodynamic factors predominate. The pattern of binding to the 9 control, building block, and receptor surfaces for the kinetic protocol (addition of HRP and 30 minute incubation) was different from the thermodynamic protocol (addition of 1.0X HRP and 30 minute incubation followed by an overnight incubation in buffer), but the patterns were consistent within each series.

Figure 19:
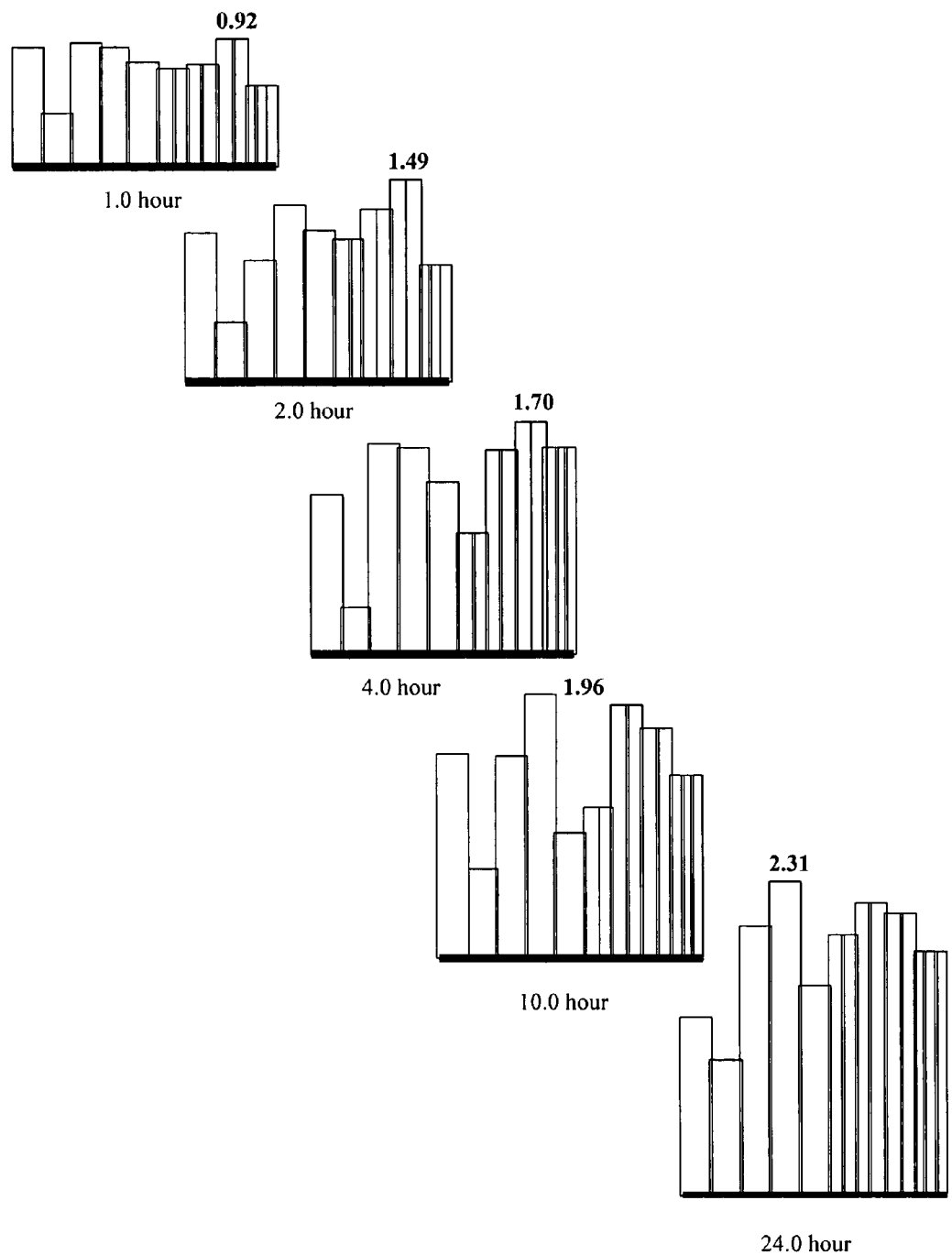
FIG. 19 illustrates bar charts of the binding pattern comparison for the ETU derivative of amino-HRP (Formula H5) using protocols similar to those used in the experiments of FIG. 18. In the present experiment, the tubes were incubated for 1, 2, 4, 10, and 24 hours of incubation.

FIG. 19 illustrates bar charts of the binding pattern comparison for the ETU derivative of amino-HRP (Formula H5) using protocols similar to those used in the experiments of FIG. 18. In the present experiment, the tubes were incubated for varying times before the buffer solution was decanted. FIG. 19 illustrates that both the extent of binding, as measured by OD value, and the pattern of binding changed as the HRP is incubated for increasing periods of time. These results reflect a kinetic response at early times and then a thermodynamic equilibrium response at later times.

Binding Evaluation: The Hydrophobic/Lipophilic Component.

Hydrophobic/lipophilic interactions can play a potentially significant role in the binding of a test ligand to a candidate receptor. However, it is relevant to demonstrate that simple partition coefficient driven equilibria were not responsible for the observed test ligand binding to the inventive candidate artificial receptors. In addition, it is relevant to define the role that simple lipophilic/hydrophobic partitioning plays in the present Examples. In fact, the present binding results were not simply the result of lipophilic/hydrophobic interactions.

Test Ligand LogP Versus Binding

The LogP values for the —NH2, —NH—Ac, —NH-34K, —NH-ETU and —NH-TCDD test ligands which were used for this study were calculated using the ACD/LogD Suite program (Advanced Chemistry Development Inc., Toronto, Canada). The values obtained were:

| TARGET | LogP |
| --- | --- |
| —NH2 | −1.74 |
| —NH-Ac | −1.05 |
| —NH-ETU | +0.26 |
| —NH-34K | +2.28 |
| —NH-TCDD | +3.84 |

Figure 20:
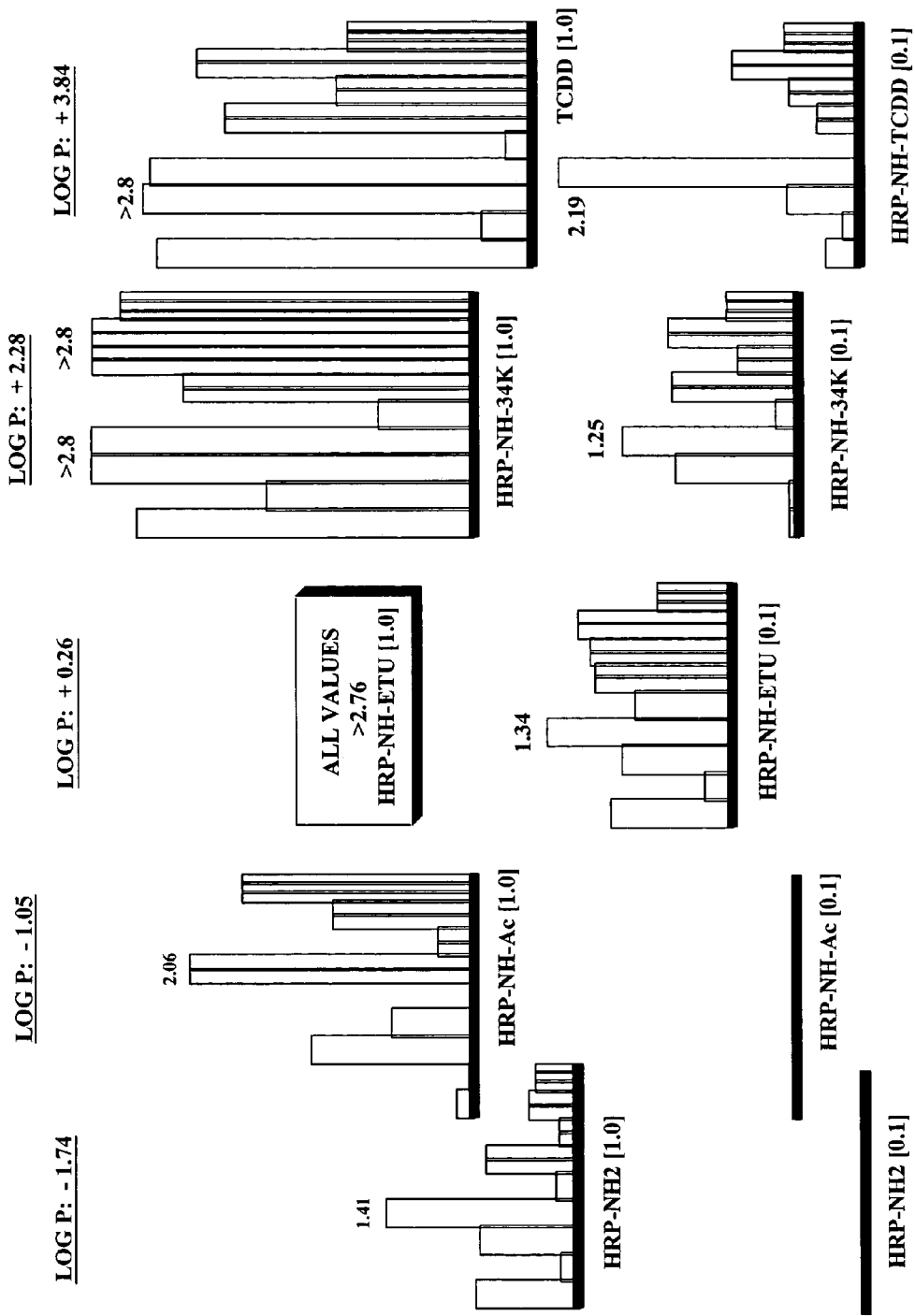
FIG. 20 illustrates the 3 bar charts (based on data presented in FIG. 16) along with LogP data for the test ligand.

FIG. 20 presents the 3 bar graphs (based on data presented in FIG. 16) along with LogP data. Pairwise comparison of individual results indicate that simple partitioning does not explain the observed results. For example, the binding (OD) values for HRP—NH-34K, -ETU and -TCDD on the homogeneous, single building block TyrA4B4 tubes spanned a range which was less than a factor of two while LogP spanned several orders of magnitude.

Figure 21:
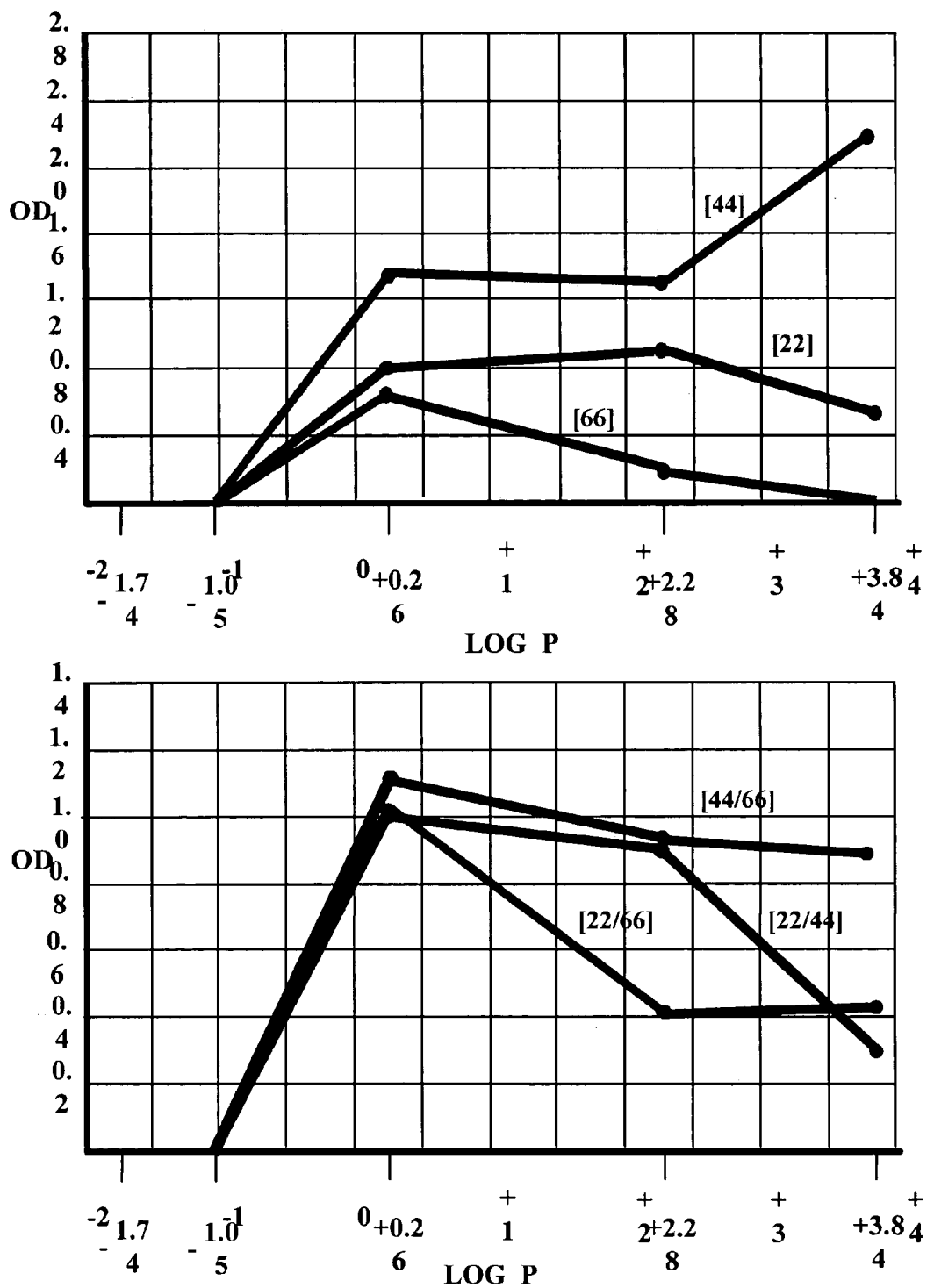
FIG. 21 illustrates graphs of OD data for 0.1 µg/ml HRP-test ligand conjugate versus LogP for the test ligand conjugate. The upper graph in FIG. 21 plots the values for the n=1, homogeneous building blocks. The lower graph plots the values for candidate receptors. In this Figure, and throughout this application, TyrAB building blocks can be further abbreviated as just the number of A and B. For example, TyrA4B4 can be abbreviated [44]. Candidate receptors including a plurality of building blocks can be similarly abbreviated. For example, a candidate receptor including TyrA4B4 plus TyrA6B6 can be abbreviated [44/66].

The binding (OD) data from the study with combinations of three building blocks in candidate receptors has been reorganized in Tables 7 and 8 to include LogP. FIG. 21 plots the OD data for the 0.1 µg/ml HRP-test ligand conjugate (Table 8) versus LogP. The upper graph in FIG. 21 plots the values for the n=1, homogeneous building blocks. The lower graph plots the values for candidate receptors.

In the upper graph in FIG. 21, the plots for the alkane substituted building block TyrA2B2 and the phenyl substituted building block TyrA4B4 generally conform to the expectation that binding increased with increasing target lipophilicity as indicated by increasing LogP. The plot for the hydrophilic building block TyrA6B6 also generally conforms to expectations as binding was strongest for the more polar/hydrophilic ETU test ligand when compared to binding of the more lipophilic 34K and TCDD test ligands. The results for 1.0 µg/ml HRP-test ligand were generally consistent (Table 7) and support the conclusion that lipophilic interactions play a role in target binding for the higher LogP targets.

TABLE 7

Binding (OD) data from combinations of three building blocks in candidate receptors including LogP.

| LOG P -> | HRP-NH2 −1.74 | —NH—Ac −1.05 | —NH-ETU +0.26 | —NH-34K +2.28 | —NH-TCDD +3.84 |
| --- | --- | --- | --- | --- | --- |
| TUBE | | | | | |
| 1. —NH2 | 0.77 | 0.19 | >2.8 | 2.45 | 2.67 |
| 2. —NH—Ac | 0.11 | 0.06 | >2.8 | 1.52 | 0.34 |

TABLE 7-continued

Binding (OD) data from combinations of three
building blocks in candidate receptors including LogP.

| LOG P -> | HRP-NH2 −1.74 | —NH—Ac −1.05 | —NH-ETU +0.26 | —NH-34K +2.28 | —NH-TCDD +3.84 |
|---|---|---|---|---|---|
| 3. −22 | 0.69 | 1.14 | >2.8 | >2.8 | >2.8 |
| 4. −44 | 1.41 | 0.56 | >2.8 | >2.8 | 2.75 |
| 5. −66 | 0.17 | 0.04 | 2.78 | 0.68 | 0.12 |
| 6. −22/44 | 0.66 | 2.06 | >2.8 | 2.15 | 2.18 |
| 7. −22/66 | 0.14 | 0.23 | >2.8 | >2.8 | 1.39 |
| 8. −44/66 | 0.36 | 0.99 | >2.8 | >2.8 | 2.38 |
| 9. −22/44/66 | 0.28 | 1.68 | >2.8 | 2.59 | 1.31 |

TABLE 8

Binding (OD) data from combinations of three building blocks
in candidate receptors including LogP.

| LOG P -> | HRP-NH2 −1.74 | —NH—Ac −1.05 | —NH-ETU +0.26 | —NH-34K +2.28 | —NH-TCDD +3.84 |
|---|---|---|---|---|---|
| TUBE | | | | | |
| 1. —NH2 | <0.04 | <0.04 | 0.86 | 0.05 | 0.22 |
| 2. —NH—Ac | <0.04 | <0.04 | 0.20 | 0.05 | 0.08 |
| 3. −22 | <0.04 | <0.04 | 0.80 | 0.86 | 0.51 |
| 4. −44 | <0.04 | <0.04 | 1.34 | 1.25 | 2.19 |
| 5. −66 | <0.04 | <0.04 | 0.68 | 0.17 | 0.04 |
| 6. −22/44 | <0.04 | <0.04 | 1.00 | 0.90 | 0.27 |
| 7. −22/66 | <0.04 | <0.04 | 1.02 | 0.42 | 0.44 |
| 8. −44/66 | <0.04 | <0.04 | 1.10 | 0.93 | 0.87 |
| 9. −2/44/66 | <0.04 | <0.04 | 0.55 | 0.51 | 0.50 |

The plots obtained for the combinations of two and three building blocks in candidate receptors provide an extended perspective on the role of lipophilic interaction (FIG. 21, lower graph). The conclusion from these plots is that although lipophilic driven partitioning may have played a role, it was not the dominant factor. For example, the plot for the candidate receptor made from the combination of TyrA2B2 plus TyrA4B4, which was the most lipophilic combination of building blocks, significantly decreased as LogP increased above the ETU value of 0.26. The OD values for ETU, 34K and TCDD binding to the candidate receptor made from the combination of TyrA4B4 plus TyrA6B6 were similar (1.10, 0.93 and 0.87 OD respectively) even though their LogP values span more than 3 orders of magnitude (0.26 to 3.84). Clearly, lipophilic binding was not the major factor in test ligand binding by these candidate receptors.

Binding Evaluation: Test Ligand Binding Patterns

Binding Pattern Interpretation

Figure 22:
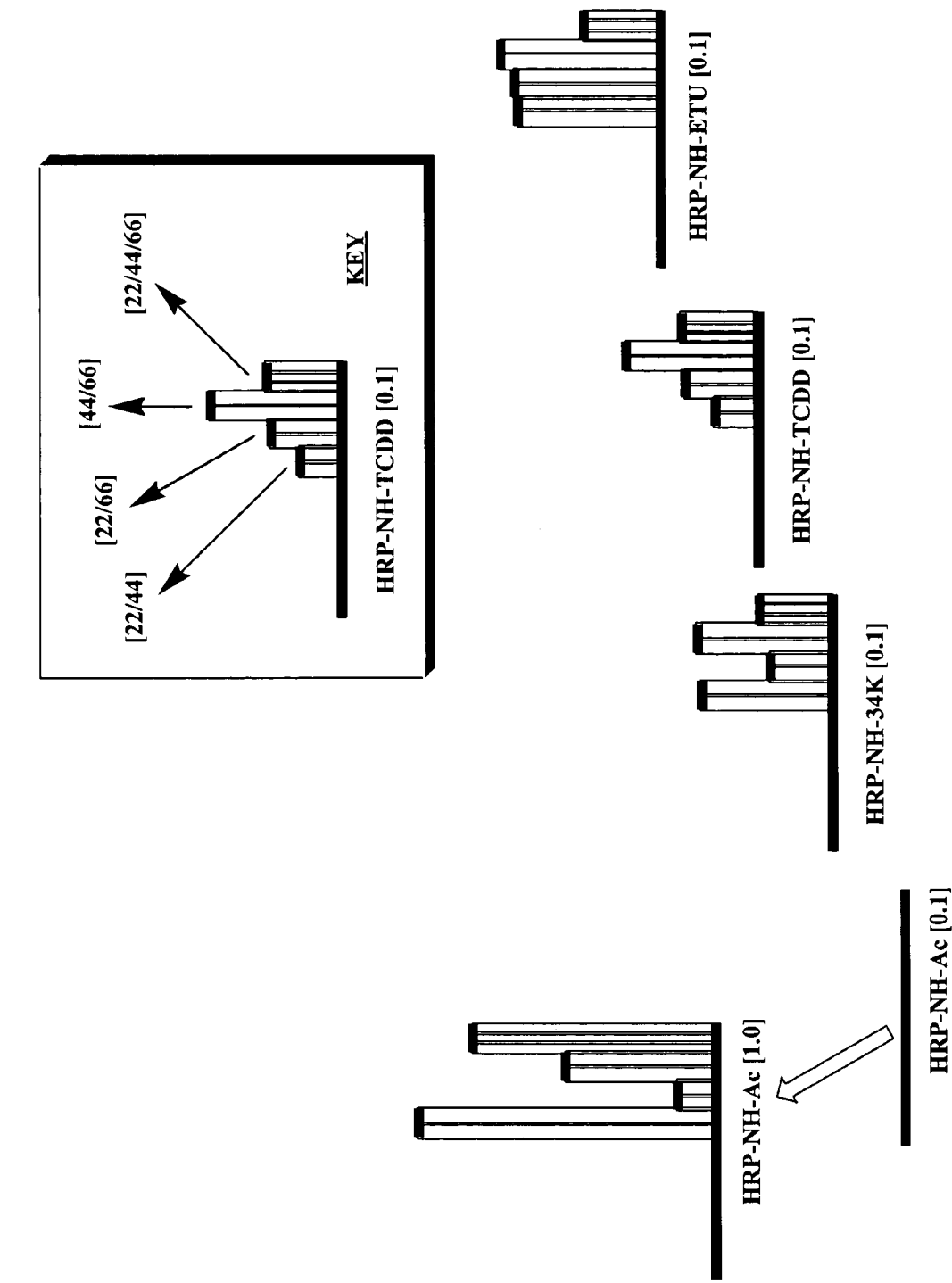
FIG. 22 illustrates bar charts comparing data for the candidate receptors with combinations of 2 and 3 building blocks binding the acetylated amino HRP control and the three 34K, TCDD and ETU test ligand conjugates.

FIG. 22 presents the data from this example for the candidate receptors with combinations of 2 and 3 building blocks versus the Ac control target and the three 34K, TCDD and ETU test ligands. It is clear from FIG. 22 that the test ligands bound to the candidate receptors with different binding patterns. An unknown sample that contained one of these four HRP conjugates could be readily identified by its distinct pattern.

Binding Affinity

It is significant to note that the observed binding affinities, even after testing a suite of only 4 candidate artificial receptors and 3 building block surfaces, spanned several orders of magnitude (FIG. 17). An estimate of binding affinity for the best receptor (TyrA2B2 plus TyrA4B4) for the ETU conjugate gives a range of $K_{Binding}$ of $2\times10^4$ to $6\times10^5$ L/M.

Reproducibility

Binding of ETU to the suite of 9 control, building block, and receptor surfaces gave OD readings from replicate experiments that were reproducible to within 5-20% (CV) for the different tubes. Certain of the tubes used in these experiments have produced good results through repeated use over a period of several months.

Conclusions

Identification of an optimum (specific, sensitive) working artificial receptor from the limited pool of 9 control, building block, and receptor surfaces was not expected and not likely. Rather, the goal of these two experiments was to demonstrate that candidate artificial receptors could be assembled and tested to provide one or more lead artificial receptors. This has been successfully demonstrated. Plus, a working artificial receptor complex was identified.

Example 4

Screening Test Ligands Against Candidate Artificial Receptors Made from 5 Building Blocks In this example, test ligands were evaluated against a broader range of candidate artificial receptors including combinations of up to 4 building blocks and made from a total of 5 building blocks.

Materials and Methods

Building Blocks

Building blocks were made as described in Example 1.

Candidate Artificial Receptors

Tubes with modified amino groups, homogeneous immobilized building blocks, and candidate artificial receptors including combinations of 2, 3 and 4 building blocks were prepared as described in Example 2. This resulted in a set of 34 control, building block, and receptor tubes (Table 9). The tubes with modified amino groups are designated as Floor tubes in Table 9. The tubes with homogeneous immobilized building blocks are designated as n=1 (number of building blocks immobilized in tube equals 1) tubes in Table 9. The tubes with candidate artificial receptors are designated as n=2, n=3, and n=4 tubes in Table 9. Table 9 lists the order in which results for the floor tubes, immobilized building blocks, candidate receptors with combinations of 2 building blocks, candidate receptors with combinations of 3 building blocks, and candidate receptors with combinations of 4 building blocks appear in FIGS. 23 and 24.

TABLE 9

Figure 23:
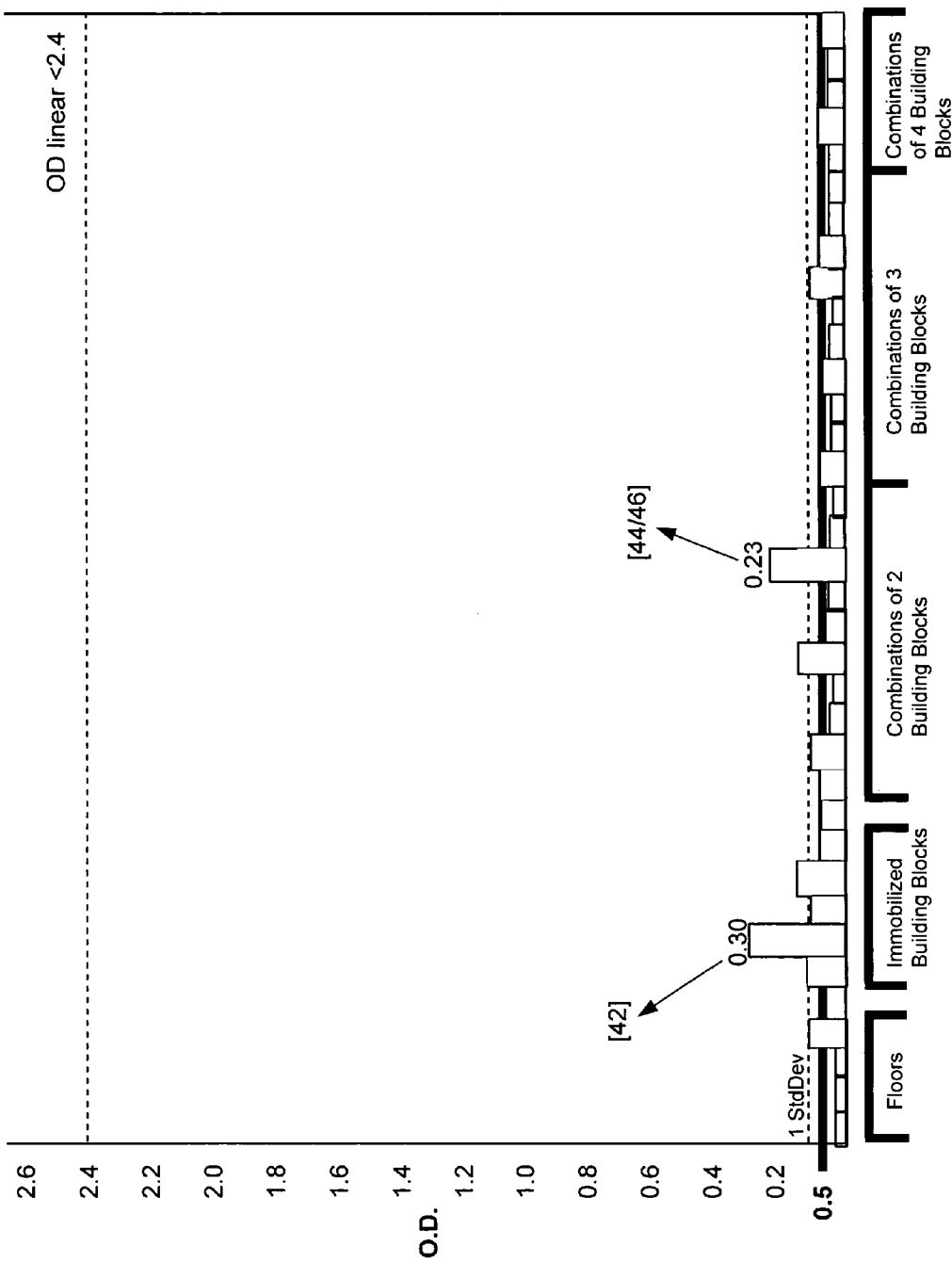
FIG. 23 schematically illustrates binding of acetylated amino HRP to derivatized-glass, to homogeneous immobilized building blocks, and to candidate receptors. The candidate receptors include 5 building blocks in combinations of 2, 3, and 4. Table 9 lists the order in which results appear in FIGS. 23 and 24 for the floor tubes, immobilized building blocks, candidate receptors with combinations of 2 building blocks, candidate receptors with combinations of 3 building blocks, and candidate receptors with combinations of 4 building blocks.
Figure 24:
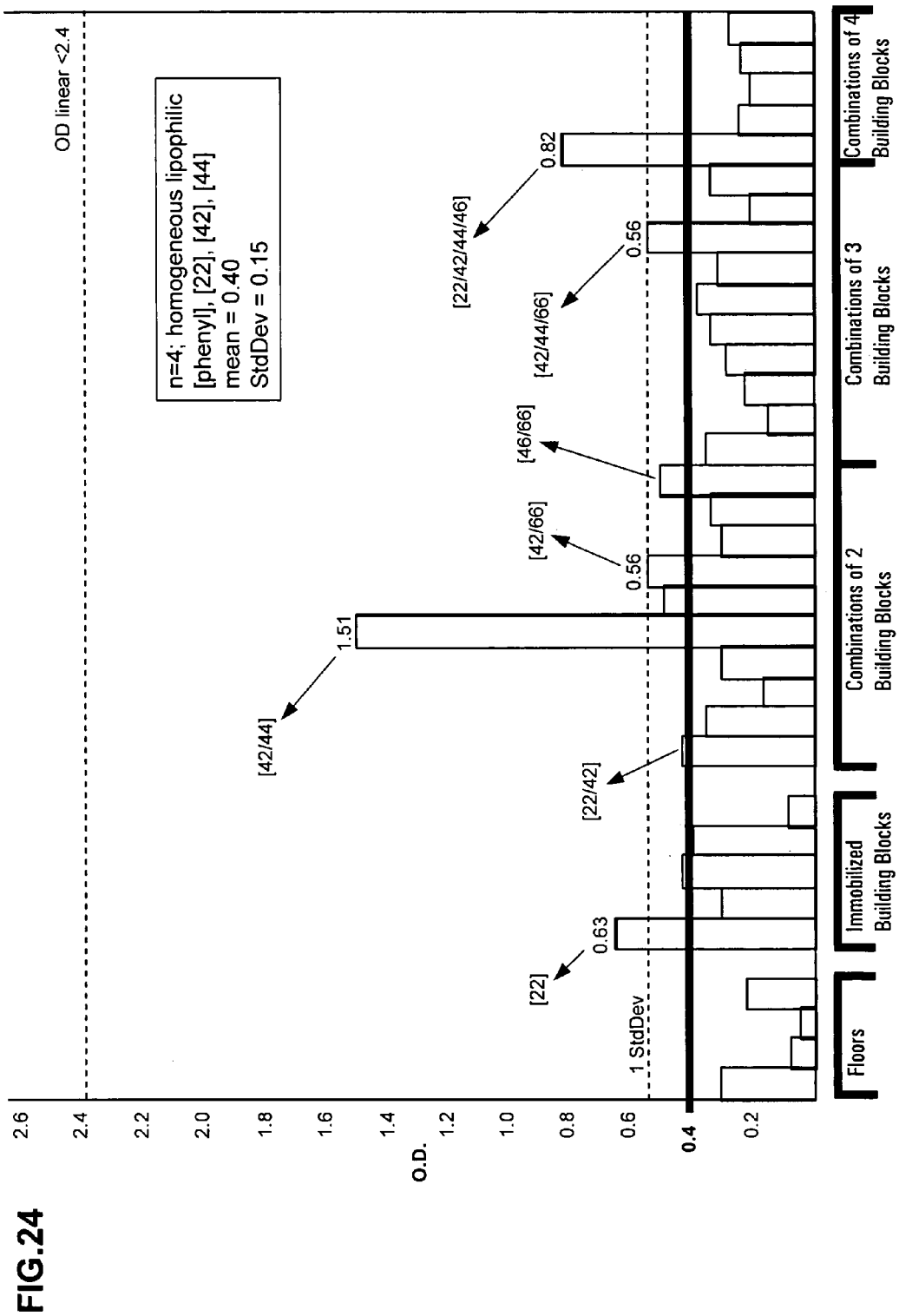
FIG. 24 schematically illustrates binding of amino-HRP-34K test ligand conjugate (Formula H4) to derivatized-glass, to homogeneous immobilized building blocks, and to candidate receptors identified in Table 9. The candidate receptors include 5 building blocks in combinations of 2, 3, and 4.

Identification grid for artificial receptors made from a set of 5 building blocks in combinations of 2, 3, and 4. Results are shown in FIGS. 23 and 24.

FLOOR f1. —NH2
f2. —Ac [—NH—C(O)—CH3]
f3. —SA [—NH—C(O)—CH$_2$CH$_2$—COOH]
f4. -phenyl [—NH—C(O)-phenyl]

Immobilized Building Blocks n1.1 - 22
n1.2 - 42
n1.3 - 44
n1.4 - 46
n1.5 - 66

Candidate Receptors with Combinations of 2 Building Blocks n2.1 - 22/42
n2.2 - 22/44
n2.3 - 22/46
n2.4 - 22/66
n2.5 - 42/44
n2.6 - 42/46
n2.7 - 42/66
n2.8 - 44/46
n2.9 - 44/46
n2.10 - 46/66

Candidate Receptors with Combinations of 3 Building Blocks n3.1 - 22/42/44
n3.2 - 22/42/46
n3.3 - 22/42/66
n3.4 - 22/44/46
n3.5 - 22/44/66
n3.6 - 22/46/66
n3.7 - 42/44/46
n3.8 - 42/44/66
n3.9 - 42/46/66
n3.10 - 44/46/66

Candidate Receptors with Combinations of 4 Building Blocks n4.1 - 22/42/44/46
n4.2 - 22/42/44/66
n4.3 - 22/42/46/66
n4.4 - 22/44/46/66
n4.5 - 42/44/46/66

Results and Discussion

Example 4 demonstrated at least that:

a) Test ligands displayed distinctive binding to a larger group of artificial receptors.

b) Various features within the receptor site cooperate to produce test ligand binding which is greater than the sum of the individual interactions.

The set of 34 tubes was screened versus several of the ligand-HRP conjugates and control HRP derivatives. FIGS. 23 and 24 illustrate that the control HRP derivative (0.1 µg/ml acetylated amino-HRP) exhibited minimal binding with this expanded set of candidate receptors, while the ligand-HRP conjugate 34K-HRP at 0.1 µg/ml displayed distinctive binding.

The target screen was based on the binding of HRP labeled test ligand. The results of Example 3 demonstrated that the binding of the HRP-NH-Ac control was minimal with respect to test ligand conjugate binding. This conclusion is further substantiated by comparing the more comprehensive data set from the N=5, 34 tube experiments. FIGS. 23 and 24 demonstrate the minimal binding of HRP-NH-Ac (0.1X) when compared to HRP-NH-34K (0.1X). For example, only two tubes showed an OD of greater than 0.2 for the HRP-NH-Ac. Considering the 32 tubes for HRP-NH-Ac that showed OD<0.2, the mean OD was 0.05 with a standard deviation of 0.04. The data in FIG. 24 show 5 tubes that had OD greater than 0.5. The 27 tubes with OD<0.5 showed a mean OD of 0.28 with a standard deviation of 0.12.

Binding Evaluation: The Hydrophobic/Lipophilic Component, Continued

Comparison to the Lipophilic Mean

The data from this example for HRP-NH-34K also provides information on the role of lipophilic interactions in the observed binding (FIG. 24). For example, if it is assumed, for the sake of an hypothesis, that the binding OD observed for the single building block, homogeneous/lipophilic building block tubes is predominantly a result of lipophilic partitioning (note that aromatic recognition elements can also exhibit pi bonding, etc.), then the mean binding observed for the [f-phenyl], TyrA2B2, TyrA4B2, and TyrA4B4 tubes (each of which includes building blocks with similar recognition elements) should be equivalent to the 'lipophilic component'. The mean for these four tubes was: mean 0.40 OD, StdDev 0.15. Clearly, examination of the binding data in FIG. 24 indicate that the lipophilic component of binding was not the only factor which contributes to the observed binding. For example, the candidate receptor made from the combination of TyrA4B2 plus TyrA4B4 produced an OD 1.51 and the candidate receptor made from the combination of TyrA2B2, TyrA4B2, TyrA4B4, plus TyrA4B6 produced OD 0.82. These receptors include lipophilic/hydrophobic recognition elements like TyrA4B2 and TyrA4B4, but produced greater binding than the lipophilic mean.

Binding Evaluation: Test Ligand Binding Patterns, Continued

Demonstration of Recognition Element Cooperative Binding

An essential feature of selective and sensitive binding by a receptor is that the various binding elements within the receptor site cooperate to produce test ligand binding which is greater than the sum of the individual interactions. Table 10 compares expected binding (OD), if binding was simply an average effect produced by the interactions of the separate building blocks, with the observed binding (OD) for several of the more prominent values illustrated in FIG. 24. The premise of this comparison is that binding could be simply the result of the average of the interactions of the separate building blocks if a simple partitioning mechanism is dominant. Alternatively, binding is more likely to be a cooperative sum of the individual interactions. The data in Table 10 demonstrate that there was a significant (2 to 4-fold) enhancement of binding for the heterogeneous candidate receptors including combinations of 2, 3 or 4 building blocks when compared to their homogeneous counterparts including only a single building block. The data was from HRP-NH-34K versus the set of building blocks (FIG. 24). The Component Average (Expected) value was calculated from the observed OD for the appropriate single building block components, e.g. for TyrA2B2 plus TyrA4B2 the component expected was the average of 0.63 OD for TyrA2B2 and 0.32 OD for TyrA4B2 which was 0.48 OD.

TABLE 10

Comparison of average versus observed binding.

Building Blocks With Similar Recognition Elements (n = 1)

| | ID | OD |
|---|---|---|
| n1.1 | TyrA2B2 | 0.63 |
| n1.2 | TyrA4B2 | 0.32 |
| n1.3 | TyrA4B4 | 0.42 |
| n1.4 | TyrA4B6 | 0.40 |
| n1.5 | TyrA6B6 | 0.06 |

Selected Building Block Distinct Recognition Elements (n = 2, 3, 4)

| RECEPTOR ID | OBSERVED OD | COMPONENT AVERAGE (EXPECTED) | OBSERVED/ EXPECTED |
|---|---|---|---|
| n2.1 TyrA2B2 plus TyrA4B2 | 0.42 | 0.48 | 0.88 |
| n2.5 TyrA4B2 plus TyrA4B4 | 1.51 | 0.37 | 4.1 |
| n2.7 TyrA4B2 plus TyrA6B6 | 0.56 | 0.19 | 2.9 |
| n2.10 TyrA4B6 plus TyrA6B6 | 0.51 | 0.23 | 2.2 |
| n3.8 TyrA4B2 plus TyrA4B4/66 | 0.56 | 0.27 | 2.1 |
| n4.1 TyrA2B2, TyrA4B2, TyrA4B4 plus TyrA4B6 | 0.82 | 0.44 | 1.9 |

Heterogeneous Binding Elements: Significance

The building blocks had two recognition elements. Building blocks that had recognition elements which are similar in structure and properties, e.g. building blocks TyrA2B2, TyrA4B4 and TyrA6B6, are described as having similar recognition elements. Building blocks which that had recognition elements with structures that are different in structure and properties, e.g. building blocks TyrA4B2 and TyrA4B6, are described as having distinct recognition elements. The binding pattern shown in FIG. 24 has 6 peaks which indicate binding was above the mean for the data set. Table 11 lists the building block composition of these candidate receptors

TABLE 11

The building block composition of candidate receptors of FIG. 24

| | BUILDING BLOCKS | | | | |
|---|---|---|---|---|---|
| TUBE | 2-2 | 4-2 | 4-4 | 4-6 | 6-6 |
| n2.1 | 2-2 | 4-2 | | | |
| n2.5 | | 4-2 | 4-4 | | |
| n2.7 | | 4-2 | | | 6-6 |
| n2.10 | | | | 4-6 | 6-6 |
| n3.8 | | 4-2 | 4-4 | | 6-6 |
| n4.1 | 2-2 | 4-2 | 4-4 | 4-6 | |
| OCCURRENCE RATIO | 2/6 | 5/6 | 3/6 | 2/6 | 3/6 |

Clearly, the 4-2 Building Block played a significant role in the binding of the HRP-NH-34K test ligand. This observation confirms that the building blocks which were prepared from heterogeneous recognition elements played a key role in artificial receptor development.

Conclusions

These results demonstrate that there was a significant enhancement of binding for the heterogeneous (n=2,3,4) candidate receptors when compared to their homogeneous (n=1) counterparts. When combined with binding pattern recognition and the demonstrated importance of both heterogeneous recognition elements and heterogeneous building blocks, these results clearly demonstrate that the present artificial receptors performed and will perform as expected to achieve the goal of target specific and sensitive artificial receptor development.

Example 5

Preparation of Microarrays of Candidate Artificial Receptors

Ultimately, the candidate artificial receptors will be presented in a microarray format on, for example, glass slides. The preparation of microarrays will employ known procedures for evaluation and optimization of robotic plate preparation and microarray high throughput screening systems. Studies with microarrays will extend the current results to evaluation of an array made from 10 building blocks, an array made from 18 building blocks, and an array made from 81 building blocks. Microarrays will be made from a 10 building block set including TyrA2B2, TyrA2B4, TyrA4B2, TyrA4B4, TyrA4B6, TyrA6B4, TyrA6B6, TyrA6B8, TyrA8B6, and TyrA8B8. A set of 10 building blocks will be combined to provide 10 spots of homogeneous immobilized building block, 45 spots of candidate artificial receptors with two building blocks, 120 spots of candidate artificial receptors with three building blocks, and 210 spots of candidate artificial receptors with four building blocks. Microarrays will be made from an 18 building block set including TyrA2B2, TyrA2B4, TyrA4B2, TyrA4B4, TyrA4B6, TyrA6B4, TyrA6B6, TyrA6B8, TyrA8B6, and TyrA8B8. A set of 18 building blocks will be combined to provide 18 spots of homogeneous immobilized building block, 153 spots of candidate artificial receptors with two building blocks, 816 spots of candidate artificial receptors with three building blocks, and 3,060 spots of candidate artificial receptors with four building blocks. The large numbers of spots from sets of 10 and 18 building blocks are sufficient to provide a thorough test of microspotting to form candidate artificial receptors and control spots.

It should be noted that, as used in this specification and the appended claims, the singular forms "a," "an," and "the"

include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "adapted and configured" describes a system, apparatus, or other structure that is constructed or configured to perform a particular task or adopt a particular configuration to. The phrase "adapted and configured" can be used interchangeably with other similar phrases such as arranged and configured, constructed and arranged, adapted, constructed, manufactured and arranged, and the like.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

What is claimed is:

1. A method of making an array, the method comprising: applying building block molecules to a solid support in a plurality of regions, each region:
   comprising 2, 3, 4, 5, or 6 different building block molecules;
   being a contiguous portion of the surface of the solid support with the different building block molecules distributed randomly and evenly throughout the contiguous region;
   and having the shape of a spot;
   independently covalently coupling the different building block molecules to the solid support in the regions;
   producing an array comprising a candidate artificial receptor, a lead artificial receptor, a working artificial receptor, or a combination thereof, in which a plurality of adjacent building block molecules form a binding site;
   wherein a first region comprises a first combination of building block molecules and a second region comprises a second combination of building block molecules;
   wherein each building block molecule comprises a framework and n recognition elements and is independently of the formula:

framework-(recognition element)$_n$ in which:
   n=1, 2, or 3; each recognition element is independently covalently coupled to the framework; and the framework comprises a functional group effective for covalent coupling to a support or a linker;
   the framework is alkyl, substituted alkyl, cycloalkyl, heterocyclic, substituted heterocyclic, aryl alkyl, aryl, heteroaryl, or heteroaryl alkyl; substituted with 1 to 4 functional groups;
   the functional groups independently being carboxyl, amine, hydroxyl, phenol, carbonyl, or thiol;
   each recognition element is independently a 1-12 carbon alkyl, substituted alkyl, cycloalkyl, heterocyclic, substituted heterocyclic, aryl alkyl, aryl, heteroaryl, or heteroaryl alkyl moiety; substituted with a group with a property of positive charge, negative charge, acid, base, electron acceptor, electron donor, hydrogen bond donor, hydrogen bond acceptor, bee electron pair, π electrons, charge polarization, hydrophilicity, or hydrophobicity; and
   when the building block molecule comprises an amino acid derivative, wherein amino acid derivatives are defined as a core feature having the chemical structure —NH—C—C(O)—, the building block molecule comprises a single amino acid derivative and the framework is the amino acid derivative.

2. The method of claim 1, wherein each recognition element is independently unsubstituted or substituted with a moiety selected from the group consisting of amine, quaternary ammonium, carboxylate, phenol, phosphate, phosphonate, phosphinate, sulphate, sulphonate, thiocarboxylate, hydroxamic acid, sulfoxide, betaine, amine oxide, amide, carboxyl, alcohol, ether, thiol, thioether, ester, thio ester, borane, borate, metal complex, alkyl, alkene, alkyne, aromatic moiety, and plurality thereof.

3. The method of claim 1, wherein the framework has the formula:

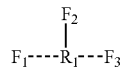

in which:
   $R_1$ is 1-12 carbon alkyl, substituted alkyl, cycloalkyl, heterocyclic, substituted heterocyclic, aryl alkyl, aryl, heteroaryl, or heteroaryl alkyl;
   $F_1$ and $F_2$ are independently carboxyl, amine, hydroxyl, phenol, carbonyl, or thiol group; or are independently 1-12 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group;
   $F_3$ and $F_4$ are independently absent, carboxyl, amine, hydroxyl, phenol, carbonyl, or thiol group; or are independently absent, or 1-12 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group.

4. The method of claim 1, further comprising:
   mixing 2, 3, 4, 5, or 6 different activated building block molecules;
   wherein applying comprises applying the mixture of building block molecules to the solid support in at least one of the regions.

5. The method of claim 1, wherein applying comprises applying individual activated building block molecules to the support in at least one of the regions.

6. The method of claim 1, further comprising:
   providing a set of building block molecules; and
   selecting from the set of building block molecules 2, 3, 4, 5, or 6 different building block molecules;
   wherein applying comprises applying the selected building block molecules to the support in at least one of the regions.

7. The method of claim 1, further comprising:
   selecting a structurally diverse set of building block molecules, the set of structurally diverse building block molecules comprising at least six of the structural characteristics of: positive charge, negative charge, acid, base, electron acceptor, electron donor, hydrogen bond donor, hydrogen bond acceptor, free electron pair, π electrons, charge polarization, hydrophilicity, or hydrophobicity.

8. The method of claim 7, comprising selecting the set of building block molecules comprising:
one or more building block molecules comprising a positively charged recognition element;
one or more building block molecules comprising a negatively charged recognition element;
one or more building block molecules comprising an acidic recognition element;
one or more building block molecules comprising a basic recognition element;
one or more building block molecules comprising an electron donating recognition element;
one or more building block molecules comprising an electron accepting recognition element;
one or more building block molecules comprising a hydrogen bond donor recognition element;
one or more building block molecules comprising a hydrogen bond acceptor recognition element;
one or more building block molecules comprising a polar recognition element;
one or more building block molecules comprising a recognition element with free electron pair(s);
one or more building block molecules comprising a recognition element with π electrons;
one or more building block molecules comprising a hydrophilic recognition element; or
one or more building block molecules comprising a hydrophobic recognition element.

9. The method of claim 1, wherein the building block molecules coupled to the support are in proximity to one another.

10. The method of claim 1, further comprising:
applying a single building block molecule to the solid support in at least one control region;
coupling the building block molecule to the solid support in the control region;
wherein a first control region comprises a first building block molecule but no other building block molecules and a second control region comprises a second building block molecule but no other building block molecules.

11. The method of claim 1, wherein one or more of the combinations of building block molecules is replicated in a plurality of regions.

12. The method of claim 1, further comprising:
providing a support comprising a functionalized lawn;
wherein coupling comprises coupling the different building block molecules to the lawn in regions.

13. The method of claim 1, wherein the building block molecules further comprise a linker and independently have the formula:

linker-framework-(first recognition element)(second recognition element)

in which the linker, first recognition element, and second recognition element are independently covalently coupled to the framework.

14. The method of claim 13, wherein the framework is of the formula of an amino acid.

15. The method of claim 14, wherein the amino acid is serine, threonine, or tyrosine.

16. The method of claim 15, wherein the amino acid is tyrosine.

17. The method of claim 13, wherein the linker is of the formula $(CH_2)_nC(O)-$, with n=1-16.

18. The method of claim 1, wherein the building block molecules further comprise a linker and independently are of formula:

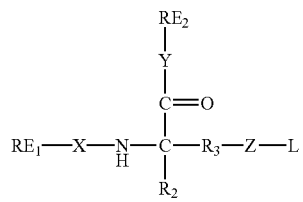

in which:
X is absent or C=O;
Y is absent, NH, or O; Z is O;
$R_2$ is H or $CH_3$;
$R_3$ is $CH_2$ or $CH_2$-phenyl;
$RE_1$ is B1, B2, B3, B4, B5, B6, B7, B8, B9, A1, A2, A3, A4, A5, A6, A7, A8, or A9;
$RE_2$ is A1, A2, A3, A4, A5, A6, A7, A8, A9, B1, B2, B3, B4, B5, B6, B7, B8, or B9;
L is $(CH_2)_n COOH$, with n=1-16;

A1 is $CH_2CH_3$;

A2 is $CH_2CH(CH_3)_2$;

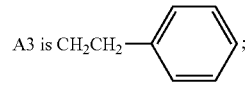

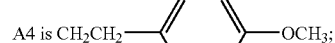

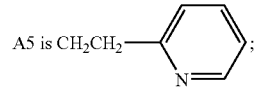

A6 is $CH_2CH_2-O-CH_3$;

A7 is $CH_2CH_2-OH$;

A8 is $CH_2CH_2-NH-C(O)CH_3$;

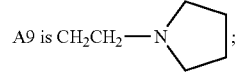

B1 is $CH_3$;

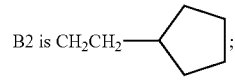

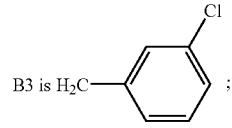

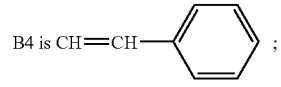

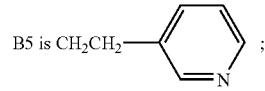

B6 is $CH_2-S-CH_3$;

B7 is $CH_2CH(OH)CH_3$;

B8 is $CH_2CH_2C(O)-NH_2$; and

B9 is $CH_2CH_2CH_2-N-(CH_3)_2$.

19. The method of claim 1, wherein applying comprises piezoelectric spotting, pin spotting, or electromagnetic spotting.

20. The method of claim 1, wherein the solid support comprises a glass plate or microscope slide.

21. The method of claim 1, wherein:
a third region comprises a third combination of building block molecules;
a fourth region comprises a fourth combination of building block molecules;
wherein the series continues through region n (an $n^{th}$ region) comprising combination n (an $n^{th}$ combination) of building block molecules and n is a positive integer less than about 1.66 million.

22. The method of claim 21, wherein n is less than or equal to 816, 2300, 3,060 3,240, 12,650, 14,950, 85,320, 88,560, 100,000, 1.66 million, or 1,663,740.

23. The method of claim 1, wherein a recognition element is substituted with or to form:
protonated phosphate, protonated phosphonate, protonated phosphinate, protonated sulphate, or protonated sulphinate;
alkyl amine, alkyl diamine, heteroalkyl amine, aryl amine, heteroaryl amine, aryl alkyl amine, heterocyclic amine, amidine, hydrazine, urea, trimethyl alkyl quaternary ammonium, dimethyl ethyl alkyl quaternary ammonium, dimethyl alkyl quaternary ammonium, aryl alkyl quaternary ammonium, or pyridinium quaternary ammonium;
alkyl carboxylate, aryl carboxylate, aryl alkyl carboxylate, or thiocarboxylate;
phosphonate or phosphinate;
primary alcohol, secondary alcohol, tertiary alcohol, or aromatic alcohol;
lower alkyl, substituted alkyl, cycloalkyl, aryl alkyl, heteroaryl alkyl, lower alkene, aryl alkene, unsubstituted aryl, heteroaryl, substituted aryl, aryl alkyl, heteroaryl alkyl, alkyl substituted aryl, or polyaromatic hydrocarbon; or
a plurality thereof.

24. The method of claim 3, wherein:
$R_1$ is 1-6 carbon alkyl, substituted alkyl, cycloalkyl, heterocyclic, substituted heterocyclic, aryl alkyl, aryl, heteroaryl, or heteroaryl alkyl;
$F_1$, $F_2$, $F_3$, or $F_4$ are independently 1-6 carbon alkyl, substituted alkyl, cycloalkyl, heterocyclic, substituted heterocyclic, aryl alkyl, aryl, heteroaryl, heteroaryl alkyl, or inorganic group substituted with carboxyl, amine, hydroxyl, phenol, carbonyl, or thiol group.
$F_3$ is absent; or
$F_3$ and $F_4$ are absent.

25. The method of claim 1, wherein the framework is:
a natural or synthetic amino acid, an α-hydroxy acid, or a thioic acid; or
a β-amino acid or homo or β analog of a natural amino acid.

26. The method of claim 1, wherein the framework is an amino acid with an amine, hydroxyl, phenol, carboxyl, thiol, thioether, or amidino group on its side chain.

27. The method of claim 1, wherein the framework is a serine, threonine, tyrosine, aspartic acid, glutamic acid, asparagine, glutamine, cysteine, lysine, arginine, or histidine moiety.

28. The method of claim 1, wherein the building block molecule further comprises a linker, and
the linker is a alkyl, substituted alkyl, cycloalkyl, heterocyclic, substituted heterocyclic, aryl alkyl, aryl, heteroaryl, heteroaryl alkyl, ethoxy or propoxy oligomer, or glycoside moiety;
substituted with a carboxyl, alcohol, phenol, thiol, amine, carbonyl, or maleimide group.

29. The method of claim 1, wherein the building block molecules comprise building block molecules independently of the formula:

framework-(first recognition element);

framework-(first recognition element)(second recognition element); or (third recognition element) framework-(first recognition element)(second recognition element);

in which the first recognition element, second recognition element, and third recognition element are independently covalently coupled to the framework.

30. The method of claim 1, wherein the building block molecules further comprise a linker and the building block molecules comprise building block molecules independently of the formula:

linker-framework-(recognition element)$_n$;

linker-framework-(first recognition element);

linker-framework-(first recognition element)(second recognition element); or (third recognition element)

linker-framework-(first recognition element)(second recognition element);

in which the linker, first recognition element, and second recognition element are independently covalently coupled to the framework.

* * * * *

UNITED STATES PATENT AND TRADEMARK OFFICE
CERTIFICATE OF CORRECTION

PATENT NO. : 7,504,364 B2  Page 1 of 2
APPLICATION NO. : 10/244727
DATED : March 17, 2009
INVENTOR(S) : Carlson It is certified that error appears in the above-identified patent and that said Letters Patent is hereby corrected as shown below:

Col. 12, line 50: "from Coming, building" should read --from Corning, building--

Col. 17, line 66: "detectable calorimetric, fluorometric," should read --detectable colorimetric, fluorometric,--

Col. 18, line 28: "detectable calorimetric, fluorometric," should read --detectable colorimetric, fluorometric,--

Col. 18, line 31: "inherent calorimetric or fluorogenic" should read --inherent colorimetric or fluorogenic--

Col. 28, line 9: "proponylamino)" should read --propionylamino)--

Col. 28, line 21: "proponylamino)" should read --propionylamino)--

Col. 68, line 26, claim 3:

"

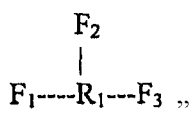

,, should read

--

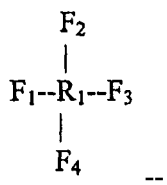

--

Col. 72, lines 25-29, claim 29:

"framework-(first recognition element) (second recognition element); or (third recognition element) framework-(first recognition element) (second recognition element);"

CERTIFICATE OF CORRECTION (continued)
U.S. Pat. No. 7,504,364 B2 should read

-- framework-(first recognition element)
                |
(second recognition element); or (third recognition element)
        |
        framework-(first recognition element)
                |
(second recognition element);

--

Col. 72, lines 41-47, claim 30:

"linker-framework-(first recognition element)(second recognition element); or (third recognition element)

linker-framework-(first recognition element)(second recognition element);"

should read

-- linker-framework-(first recognition element)
                |
(second recognition element); or (third recognition element)
        |
linker-framework-(first recognition element)
        |
(second recognition element);

--

Signed and Sealed this

Twenty-third Day of February, 2010

David J. Kappos
*Director of the United States Patent and Trademark Office*